(12) United States Patent
Labrijn et al.

(10) Patent No.: US 10,590,206 B2
(45) Date of Patent: Mar. 17, 2020

(54) INERT FORMAT

(71) Applicant: GENMAB A/S, Copenhagen V (DK)

(72) Inventors: Aran Frank Labrijn, Nigtevecht (NL);
Joyce Meesters, Utrecht (NL); Joost J. Neijssen, Werkhoven (NL); Edward Norbert Van Den Brink, Halfweg (NL); Janine Schuurman, Diemen (NL); Paul Parren, Odijk (NL)

(73) Assignee: GENMAB A/S, Copenhagen V (DK)

( * ) Notice: Subject to any disclaimer, the term of this patent is extended or adjusted under 35 U.S.C. 154(b) by 80 days.

(21) Appl. No.: 14/760,157

(22) PCT Filed: Jan. 9, 2014

(86) PCT No.: PCT/EP2014/050340
§ 371 (c)(1),
(2) Date: Jul. 9, 2015

(87) PCT Pub. No.: WO2014/108483
PCT Pub. Date: Jul. 17, 2014

(65) Prior Publication Data
US 2015/0337049 A1 Nov. 26, 2015

Related U.S. Application Data

(60) Provisional application No. 61/751,045, filed on Jan. 10, 2013.

(30) Foreign Application Priority Data

Jan. 10, 2013 (DK) ............... 2013 00019
Jul. 5, 2013 (WO) ........... PCT/EP2013/064330

(51) Int. Cl.
| | | |
|---|---|---|
| C07K 16/40 | (2006.01) | |
| C07K 16/28 | (2006.01) | |
| C07K 16/10 | (2006.01) | |
| C07K 16/36 | (2006.01) | |
| C07K 16/00 | (2006.01) | |
| C07K 16/32 | (2006.01) | |
| C07K 16/12 | (2006.01) | |
| A61K 39/00 | (2006.01) | |

(52) U.S. Cl.
CPC ............ *C07K 16/40* (2013.01); *C07K 16/00* (2013.01); *C07K 16/1063* (2013.01); *C07K 16/1271* (2013.01); *C07K 16/2809* (2013.01); *C07K 16/2863* (2013.01); *C07K 16/2887* (2013.01); *C07K 16/2896* (2013.01); *C07K 16/32* (2013.01); *C07K 16/36* (2013.01); *A61K 2039/505* (2013.01); *C07K 2317/24* (2013.01); *C07K 2317/31* (2013.01); *C07K 2317/41* (2013.01); *C07K 2317/51* (2013.01); *C07K 2317/515* (2013.01); *C07K 2317/524* (2013.01); *C07K 2317/526* (2013.01); *C07K 2317/53* (2013.01); *C07K 2317/71* (2013.01); *C07K 2317/732* (2013.01); *C07K 2317/734* (2013.01); *C07K 2317/74* (2013.01); *C07K 2317/75* (2013.01); *C07K 2317/77* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | |
|---|---|---|
| 2010/0015135 A1 | 1/2010 | Wu et al. |
| 2016/0168247 A1 | 6/2016 | Van Den Brink et al. |
| 2016/0333095 A1 | 11/2016 | Van Den Brink et al. |
| 2017/0355767 A1 | 12/2017 | Engelberts et al. |

FOREIGN PATENT DOCUMENTS

| | | | | |
|---|---|---|---|---|
| EP | 2067789 A1 | * | 6/2009 | ......... C07K 16/2854 |
| EP | 2067789 A1 | | 6/2009 | |
| WO | 2012/113813 A1 | | 8/2012 | |
| WO | WO2012/143524 | * | 10/2012 | |
| WO | WO-2012143524 A2 | * | 10/2012 | ......... C07K 16/1063 |
| WO | WO2012162067 | * | 11/2012 | |

OTHER PUBLICATIONS

Alegre M.-L., et al., "Effect of a single amino acid mutation on the activating and immunosuppressive properties of a "humanized" OKT3 monoclonal antibody ," J. Immunol., vol. 148(11): 3461-3468 (1992).

Armour K. et al., "Differential binding to human FcgammaRIIa and FcgammaRIIb receptors by human IgG wildtype and mutant antibodies," Molecular Immunology, vol. 40:585-593 (2003).

Canfield, S.M. et al., "The binding affinity of human IgG for its high affinity Fc receptor is determined by multiple amino acids in the CH2 domain and is modulated by the hinge region," J Exp Med., vol. 173(6):1483-1491 (1991).

Chu S.Y., et al., "Reduction of total IgE by targeted coengagement of IgE B-cell receptor and FcgammaRIIb with Fc-engineered antibody," J Allergy Clin Immunol., vol. 129(4):1102-1115 (2012).

Hezareh M. et al.,"Effector function activities of a panel of mutants of a broadly neutralizing antibody against human immunodeficiency virus type I," Journal of Virology, The American Society for Microbiology, US, vol. 75 (24):12161-12168 (2001).

Hinojosa, L.E. et al., "Construction of a Recombinant Non-Mitogenic Anti-Human CD3 Antibody," HYBRIDOMA, vol. 29(2): 115-124 (2010).

(Continued)

*Primary Examiner* — Meera Natarajan
(74) *Attorney, Agent, or Firm* — Nelson Mullins Riley & Scarborough LLP; Jane E. Remillard, Esq.; Christopher L. Frank

(57) ABSTRACT

Described herein are, proteins comprising amino acid substitutions in at least one of a first and a second polypeptide chain. Furthermore, is described the uses and methods related to said proteins.

20 Claims, 26 Drawing Sheets

Specification includes a Sequence Listing.

(56) References Cited

OTHER PUBLICATIONS

Horton H.M., et al., "Antibody-mediated coengagement of FcgammaRIIb and B cell receptor complex suppresses humoral immunity in systemic lupus erythematosus," J Immunol., vol. 186 (7): 4223-4233 (2011).

Idusogie E. et al., "Mapping of the C1q binding site on rituxan, a chimeric antibody with a human IgG1 Fc," Journal of Immunology, vol. 164:4178-4184 (2000).

Li, B. et al., "Construction and characterization of a humanized anti-human CD3 monoclonal antibody 12F6 with effective immunoregulation functions," Immunology, Blackwell Publishing, Oxford, GB, vol. 116(4): 487-498 (2005).

Li, J. et al., "Phase I trial of a humanized, Fc receptor nonbinding anti-CD3 antibody, hu12F6mu in patients receiving renal allografts," MABS, vol. 2 (4):449-456 (2010).

Lund J. et al., "Multiple binding sites on the CH2 domain of IgG for mouse Fc gamma R11," Mol Immunol., vol. 29 (1): 53-59 (1992).

Oganesyan, V et al., "Structural characterization of a human Fc fragment engineered for lack of effector functions," Acta. Cryst., D64, 700-704 (2008).

Shields R.L. et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., vol. 276 (9): 6591-6604 (2001).

Duncan, "The binding site for C1q on IgG," Nature, vol. 332: 738-740 (1988).

Tamm A., et al., "IgG binding sites on human Fc gamma receptors," Int Rev Immunol., vol. 16(1-2): 57-85 (1997).

Tao M.H. et al., "Studies of aglycosylated chimeric mouse-human IgG. Role of carbohydrate in the structure and effector functions mediated by the human IgG constant region," J Immunol., vol. 143(8): 2595-2601 (1989).

Woodle, E.S., et al., "Phase I Trial of a Humanized, Fc Receptor nonbinding OKT3 antibody, huOKT3gamma1 (Ala-Ala) in the Treatment of Acute Renal Allograft Rejection," Transplantation, Williams and Wilkins, Baltimore, US, vol. 68(5): 606-618 (1999).

Xu D., et al., "In vitro characterization of five humanized OKT3 effector function variant antibodies," Cellular Immunology, vol. 200(1):16-26 (2000).

U.S. Appl. No. 14/902,757, dated Jun. 26, 2019.
U.S. Appl. No. 14/902,757, dated Mar. 14, 2019.
U.S. Appl. No. 14/902,757, dated Jul. 30, 2018.
U.S. Appl. No. 15/110,414, dated May 1, 2019.
U.S. Appl. No. 15/110,414, dated Nov. 27, 2018.
U.S. Appl. No. 15/541,594, dated Jul. 18, 2019.
U.S. Appl. No. 15/541,594, dated Nov. 27, 2018.

* cited by examiner

| Antibody | EC50 (µg/mL) |
|---|---|
| bsIgG1 CD3xHER2-LFLEDA | 4.46 |
| bsIgG1 huCD3-H3L1xHER2-LFLEDA | 3.54 |
| IgG1-CD3-LFLEDA | 0.47 |
| IgG1-huCD3-H3L1-LFLEDA | 0.30 |

```
                        SEQUENCE LISTING

<160> NUMBER OF SEQ ID NOS: 21

<210> SEQ ID NO 1
<211> LENGTH: 8
<212> TYPE: PRT
<213> ORGANISM: homo sapiens

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: homo sapiens

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: homo sapiens

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: homo sapiens

<400> SEQUENCE: 4

Thr Gly Ala Val Thr Thr Ser Asn Tyr
1               5

<210> SEQ ID NO 5
<211> LENGTH: 9
<212> TYPE: PRT
<213> ORGANISM: homo sapiens

<400> SEQUENCE: 5
```

```
Ala Leu Trp Tyr Ser Asn Leu Trp Val
 1               5
```

<210> SEQ ID NO 6
<211> LENGTH: 125
<212> TYPE: PRT
<213> ORGANISM: homo sapiens

<400> SEQUENCE: 6

```
Glu Val Lys Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 7
<211> LENGTH: 125
<212> TYPE: PRT
<213> ORGANISM: homo sapiens

<400> SEQUENCE: 7

```
Glu Val Lys Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 8
<211> LENGTH: 125
<212> TYPE: PRT
<213> ORGANISM: homo sapiens

<400> SEQUENCE: 8

```
Glu Val Lys Leu Val Glu Ser Gly Gly Gly Leu Val Lys Pro Gly Arg
 1               5                  10                  15

Ser Leu Arg Leu Ser Cys Ala Ala Ser Gly Phe Thr Phe Asn Thr Tyr
```

```
                20                  25                  30
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 9
<211> LENGTH: 125
<212> TYPE: PRT
<213> ORGANISM: homo sapiens

<400> SEQUENCE: 9

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser
            115                 120                 125

<210> SEQ ID NO 10
<211> LENGTH: 109
<212> TYPE: PRT
<213> ORGANISM: homo sapiens

<400> SEQUENCE: 10

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
```

-continued

<210> SEQ ID NO 11
<211> LENGTH: 109
<212> TYPE: PRT
<213> ORGANISM: homo sapiens

<400> SEQUENCE: 11

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 12
<211> LENGTH: 109
<212> TYPE: PRT
<213> ORGANISM: homo sapiens

<400> SEQUENCE: 12

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 13
<211> LENGTH: 330
<212> TYPE: PRT
<213> ORGANISM: homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
             85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 186
<212> TYPE: PRT
<213> ORGANISM: homo sapiens

<400> SEQUENCE: 14

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
```

```
            100                 105                 110
Val Ile Val Asp Ile Cys Ile Thr Gly Gly Leu Leu Leu Val Tyr
            115                 120                 125

Tyr Trp Ser Lys Asn Arg Lys Ala Lys Ala Lys Pro Val Thr Arg Gly
            130                 135             140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                    165                 170                 175

Leu Tyr Ser Gly Leu Asn Gln Arg Arg Ile
                180                 185
```

<210> SEQ ID NO 15
<211> LENGTH: 171
<212> TYPE: PRT
<213> ORGANISM: homo sapiens

<400> SEQUENCE: 15

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 16
<211> LENGTH: 119
<212> TYPE: PRT
<213> ORGANISM: homo sapiens

<400> SEQUENCE: 16

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Gly Met Phe Trp Val Arg Gln Ala Pro Gly Lys Gly Leu Glu Trp Val
            35                  40                  45

Ala Thr Ile Ser Arg Tyr Ser Arg Tyr Ile Tyr Tyr Pro Asp Ser Val
        50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Arg Arg Pro Leu Tyr Gly Ser Ser Pro Asp Tyr Trp Gly Gln Gly
                100                 105                 110

Thr Leu Val Thr Val Ser Ser
            115
```

<210> SEQ ID NO 17
<211> LENGTH: 106
<212> TYPE: PRT
<213> ORGANISM: homo sapiens

<400> SEQUENCE: 17

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Val
                20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105
```

<210> SEQ ID NO 18
<211> LENGTH: 121
<212> TYPE: PRT
<213> ORGANISM: homo sapiens

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Leu Ser Ala Tyr Ser Gly Asn Thr Ile Tyr Ala Gln Lys Leu
50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Tyr Trp Gly
                100                 105                 110

Gln Gly Thr Leu Val Thr Val Ser Ser
            115                 120
```

<210> SEQ ID NO 19
<211> LENGTH: 107
<212> TYPE: PRT
<213> ORGANISM: homo sapiens

<400> SEQUENCE: 19

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 20
<211> LENGTH: 330
<212> TYPE: PRT
<213> ORGANISM: homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                    260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 21
<211> LENGTH: 177
<212> TYPE: PRT
<213> ORGANISM: homo sapiens

<400> SEQUENCE: 21

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
            85                  90                  95

Val Met Ala Val Ala Thr Ile Val Ile Val Asp Ile Cys Ile Thr Leu
            100                 105                 110

Gly Leu Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
            130                 135                 140

Gln Asn Lys Glu Arg Pro Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile
```

INERT FORMAT

RELATED APPLICATIONS

This application is a 35 U.S.C. 371 national stage filing of International Application No. PCT/EP2014/050340, filed Jan. 9, 2014, which claims priority to International Application No. PCT/EP2013/064330, filed Jul. 5, 2013, U.S. Patent Application No. 61/751,045, filed Jan. 10, 2013, and Danish Patent Application No. PA201300019, filed Jan. 10, 2013. The contents of the aforementioned applications are hereby incorporated by reference.

FIELD OF INVENTION

The present invention relates to proteins, such as antibodies, comprising a first polypeptide and a second polypeptide which are inert in the sense that they do not induce any Fc receptor-mediated functions leading to cell activation, resulting from three modifications in the Fc region.

BACKGROUND OF THE INVENTION

The effector functions mediated by the Fc region of an antibody allow for the destruction of foreign entities, such as the killing of pathogens and the clearance and degradation of antigens. Antibody-dependent cell-mediated cytotoxicity (ADCC) and antibody-dependent cell-mediated phagocytosis (ADCP) are initiated by binding of the Fc region to Fc receptor (FcR)-bearing cells, whereas complement-dependent cytotoxicity (CDC) is initiated by binding of the Fc region to C1q, which initiates the classical route of complement activation.

Fc-mediated effector functions, such as ADCC and complement activation, have been suggested to contribute to the therapeutic efficacy of monoclonal antibodies used for the treatment of cancer (Weiner et al. Cell 2012, 148:1081-1084).

Previous efforts have been made to reduce unwanted effects caused by binding to the Fc region, e.g. cytokine storm and associated toxic effects or platelet aggregation, by providing antibody fragments or antibodies with mutated amino acid sequences. For example, antibody fragments, such as Fab, F(ab')$_2$, or scFv molecules, intrinsically lack Fc-effector functions, but have a short in vivo half-life and may require additional modifications to extend the half-life. Tao and Morrison (1989) describes studies of aglycosylated chimeric mouse-human IgG. Bolt et al. (1993) describes generation of a humanized, non-mitogenic CD3 monoclonal antibody which retains in vitro immunosuppressive properties.

Canfield and Morrison (2003) describes the binding affinity of human IgG for its high affinity Fc receptor is determined by multiple amino acids in the CH2 domain and is modulated by the hinge region.

Hezarah et al. (2001) describes effector function activities of a panel of mutants of a broadly neutralizing antibody against human immunodeficiency virus type 1.

Armour et al. (2003) describes differential binding to human FcgammaRIIa and FcgammaRIIb receptors by human IgG wildtype and mutant antibodies.

Idusogie et al. (2000) describes mapping of the C1q binding site on rituxan, a chimeric antibody with a human IgG1 Fc.

Shields et al (2001) describes high resolution mapping of the binding site on human IgG1 for FcγRI, FcγRII, RcγRIII, and FcRn and design of IgG1 variants with improved binding to the FcγR.

Oganesyan et al. (2008) describes structural characterization of a human Fc fragment engineered for lack of effector functions.

Duncan et al. (2008) describes localization of the binding site for the human high-affinity Fc receptor on IgG.

Parren et al, (1992) describes the interaction of IgG subclasses with the low affinity Fc gamma RIIa (CD32) on human monocytes, neutrophils, and platelets.

Newman et al (2001) describes modification of the Fc region of a primatized IgG antibody to human CD4 retains its ability to modulate CD4 receptors but does not deplete CD4(+) T cells in chimpanzees.

Alternatively, the hinge region of the antibody has been reported to be of importance with respect of interactions with FcγRs and complement. Dall'Acqua et al (2006) describes modulation of the effector functions of a human IgG1 through engineering of its hinge region. However, none of the previously engineered Fc regions are completely devoid of Fc-mediated functions. Furthermore, the impact of these specific mutations on immunogenicity and in vivo half-life is often unknown.

As described above, there is a need of proteins incapable of inducing a range of specific effector functions and at the same time have conserved pharmacokinetic properties. The present invention provides such proteins.

SUMMARY OF INVENTION

The present invention provides proteins and antibodies having a non-activating Fc region as compared to a wild-type protein or antibody. Without being limited to theory, it is believed that the proteins and antibodies are incapable of inducing a range of effector functions caused by interaction between the Fc region and effector components, such as Fc receptor binding.

Thus, in one aspect, the present invention relates to a protein comprising a first polypeptide and a second polypeptide, wherein said first and second polypeptide each comprises at least a hinge region, a CH2 region and a CH3 region of an immunoglobulin heavy chain, wherein in at least one of said first and second polypeptide the amino acid in positions corresponding to positions L234, L235 and D265 in a human IgG1 heavy chain, are not L, L, and D, respectively.

In another aspect, the present invention relates to a variant of a parent protein.

In another aspect, the present invention relates to a composition comprising a protein or variant according to the invention.

In another aspect, the present invention relates to a pharmaceutical composition comprising a protein or a variant according to the invention and a pharmaceutical acceptable carrier.

The present invention also relates to the use of a protein, variant, composition, or pharmaceutical composition according to the invention for use in the treatment of a disease.

Another aspect of the invention relates to a method of treatment of cancer comprising administering a protein, variant, composition, or pharmaceutical composition according to the invention to a subject.

Figure 1A:
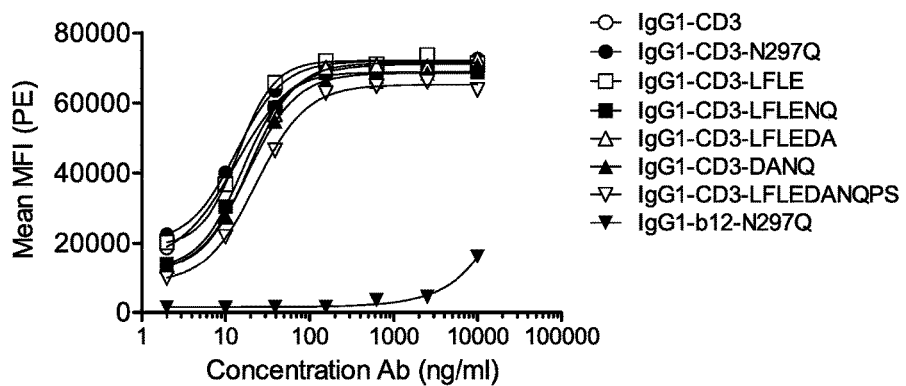
FIGS. 1A-1D: Binding curves of IgG1-CD3 (IgG1-huCLB-T3/4-F405L) or IgG1-HER2 (IgG1-HER2-169-K409R) monospecific antibody variants and bsIgG1-CD3×
Figure 1B:
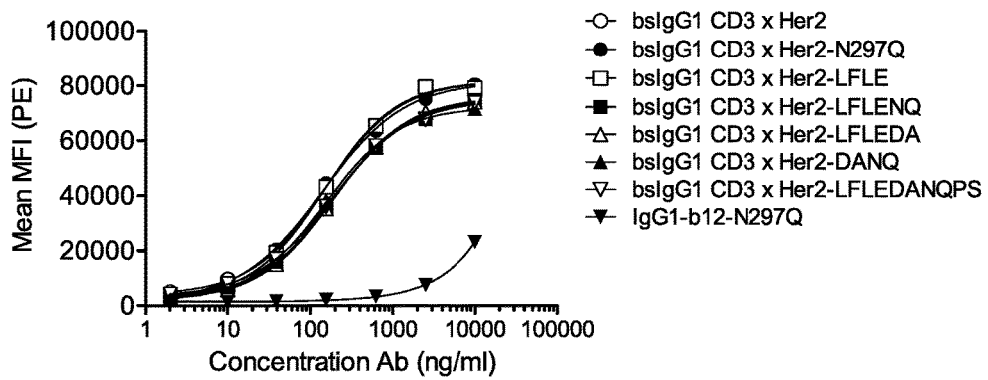
Figure 1C:
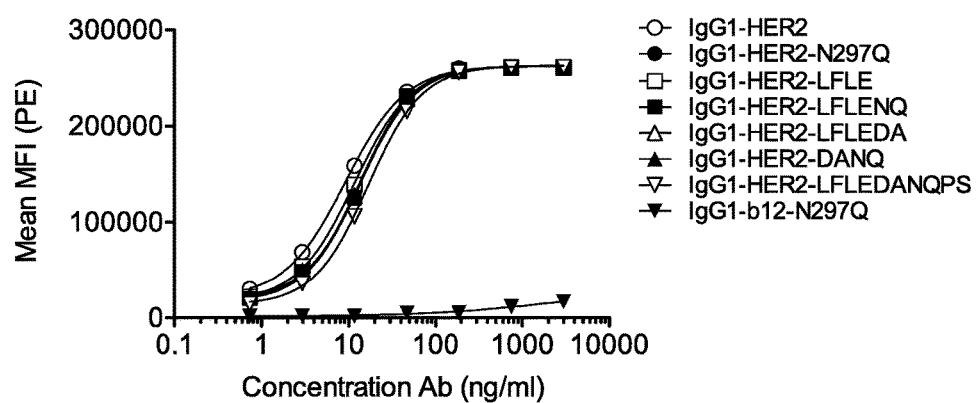
Figure 1D:
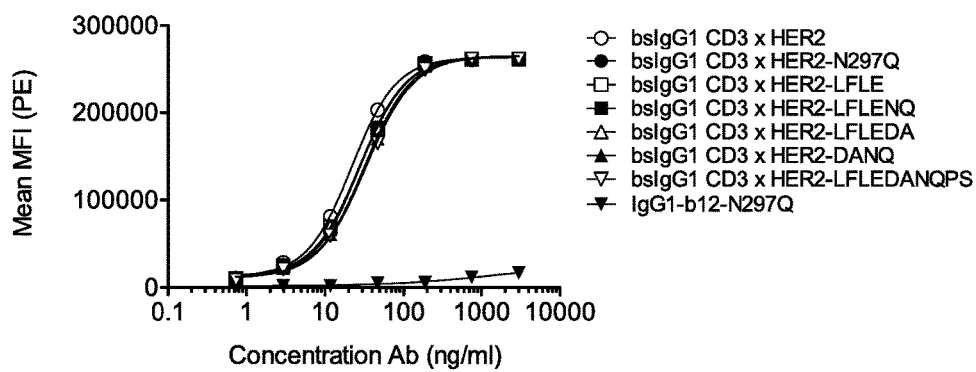

HER2 (IgG1-huCLB-T3/4×HER2-169) bispecific antibody variants to their specific target on Jurkat (FIG. 1A, FIG. 1B) or AU565 cells (FIG. 1C, FIG. 1D). Data shown are mean fluorescence intensities (MFI) of one representative experiment for each cell line, as described in Example 2.

Figure 2A:
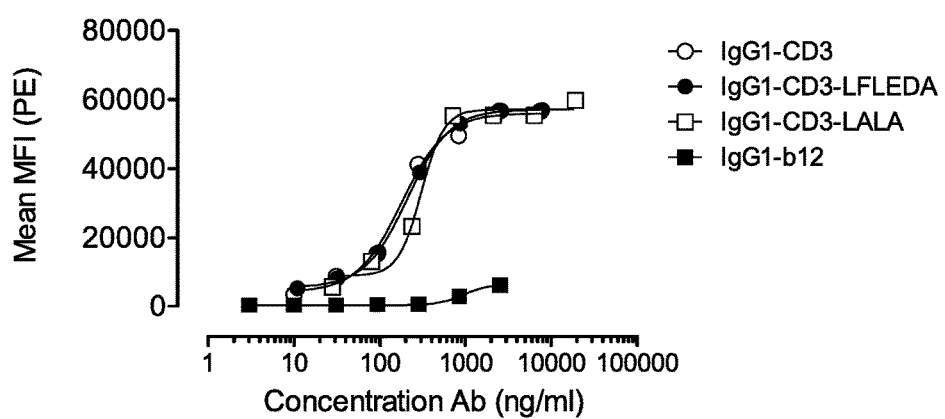
Figure 2B:
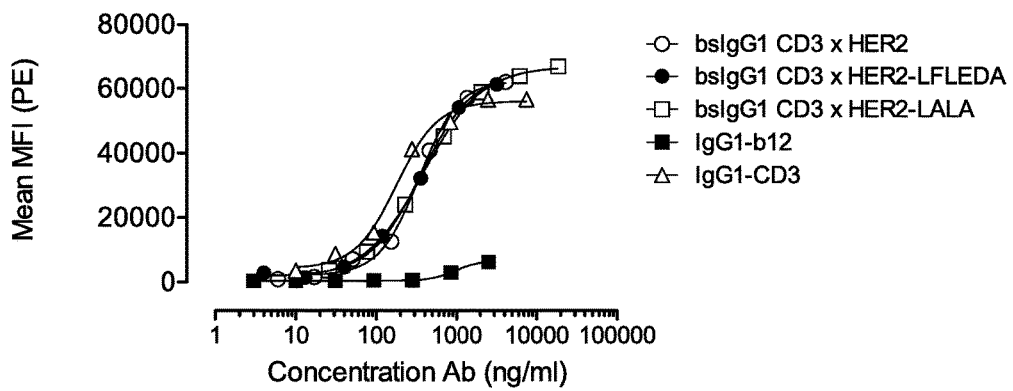
Figure 2C:
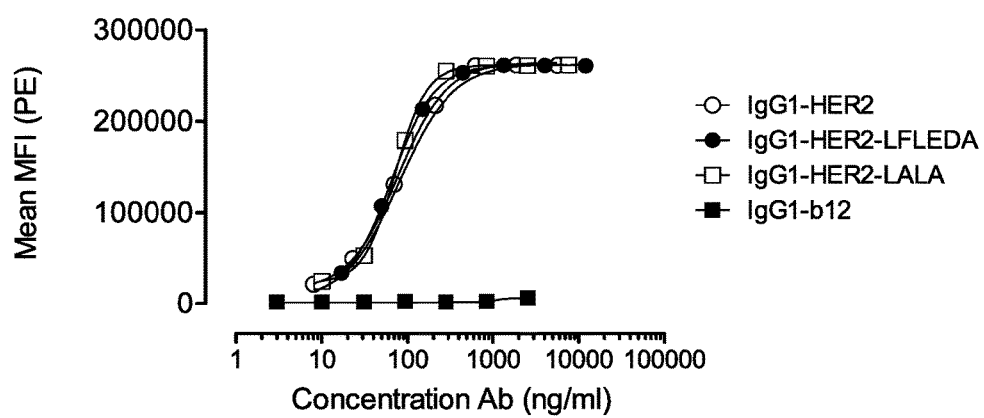
Figure 2D:
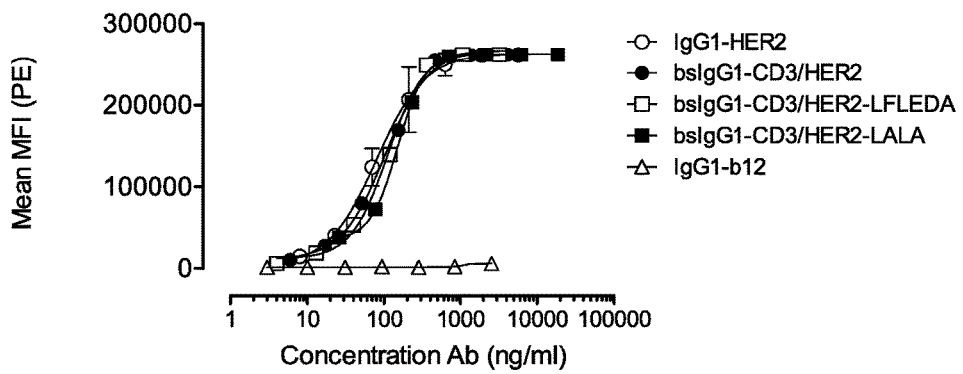

FIGS. 2A-2D: Binding curves of IgG1-CD3 (IgG1-huCLB-T3/4-F405L) or IgG1-HER2 (IgG1-HER2-169-K409R) monospecific antibody variants and bsIgG1 CD3× HER2 (IgG1-huCLB-T3/4×HER2-169) bispecific antibody variants to their specific target on Jurkat (FIGS. 2A and 2B) or AU565 cells (FIGS. 2C and 2D). Data shown are mean fluorescence intensities (MFI) of one representative experiment for each cell line, as described in Example 2.

Figure 3A:
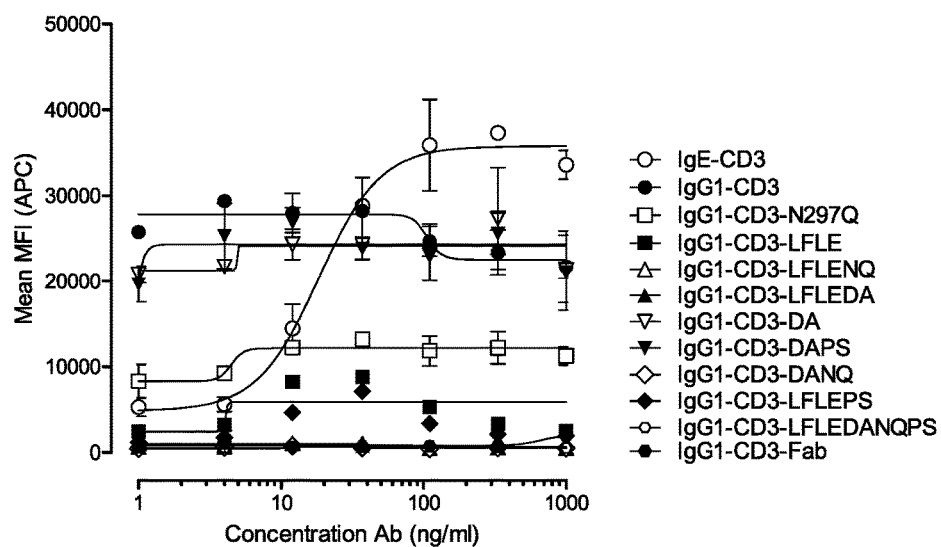
Figure 3B:
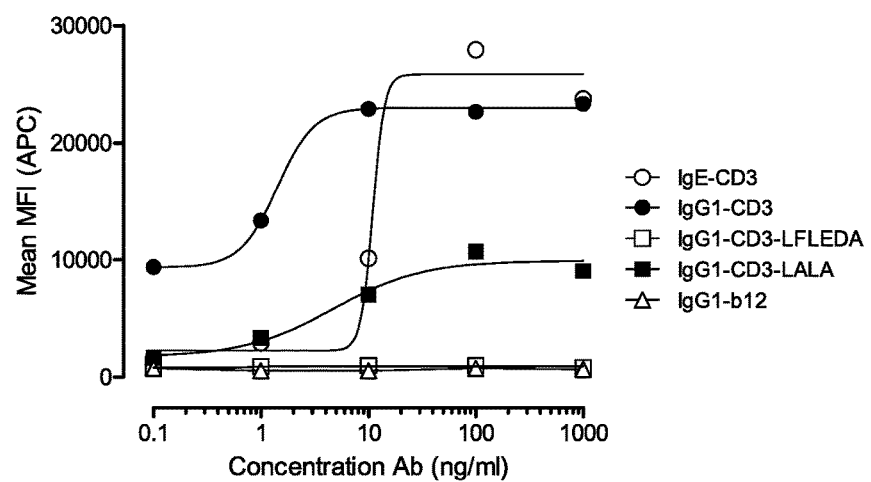

FIGS. 3A and 3B: FACS analysis of CD69 expression on T-cells in PBMC cultures as described in Example 3. The PBMC cultures were treated with titrated IgG1-CD3 (huCLB-T3/4) antibody variants. Representative examples of three experiments are shown.

Figure 4A:
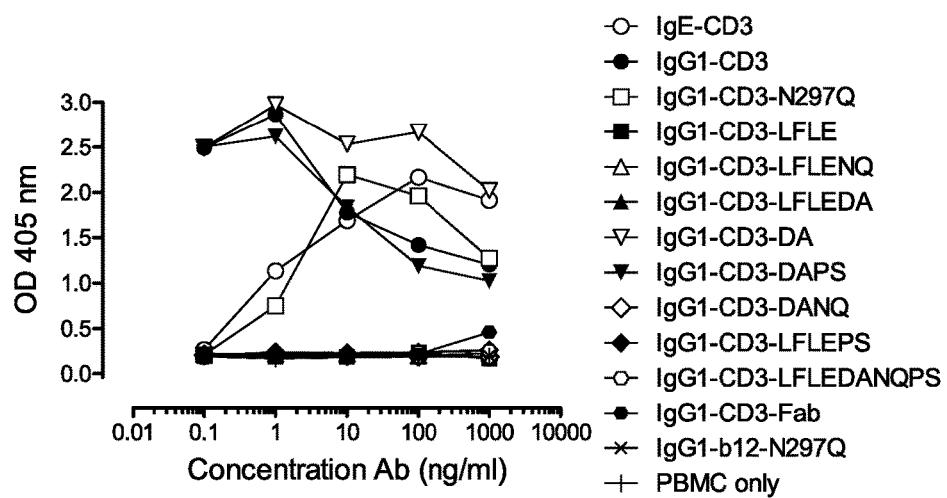
Figure 4B:
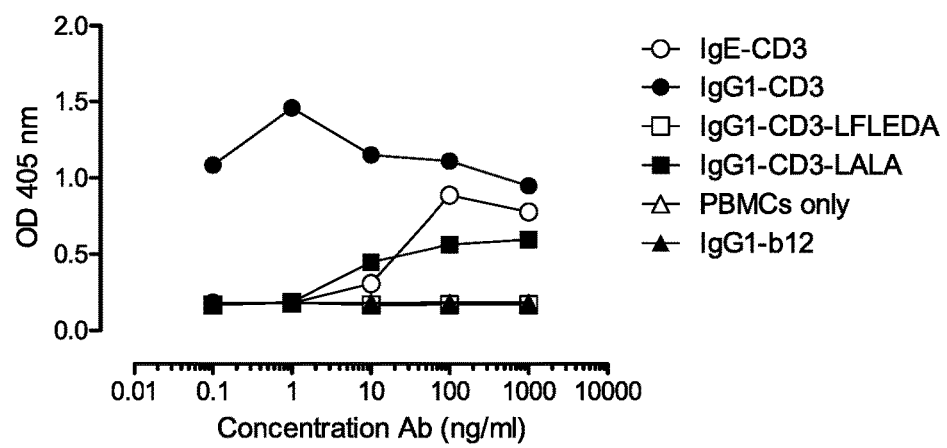
Figure 5A:
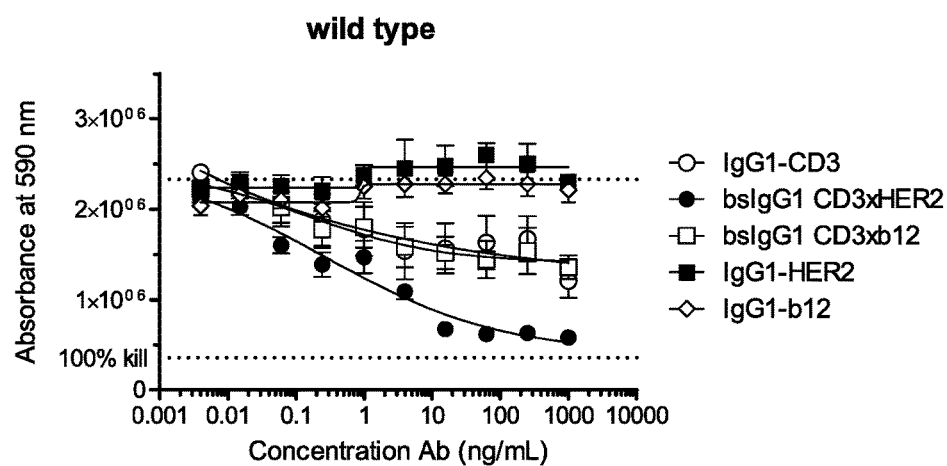
Figure 5B:
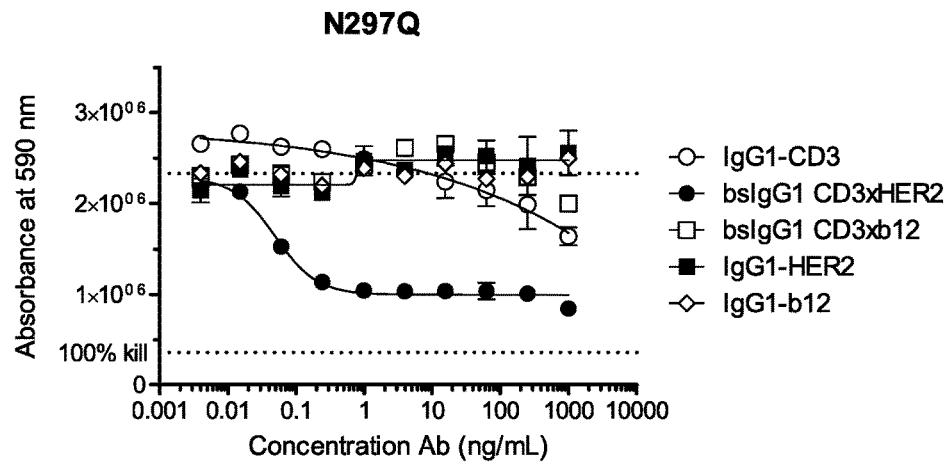
Figure 5C:
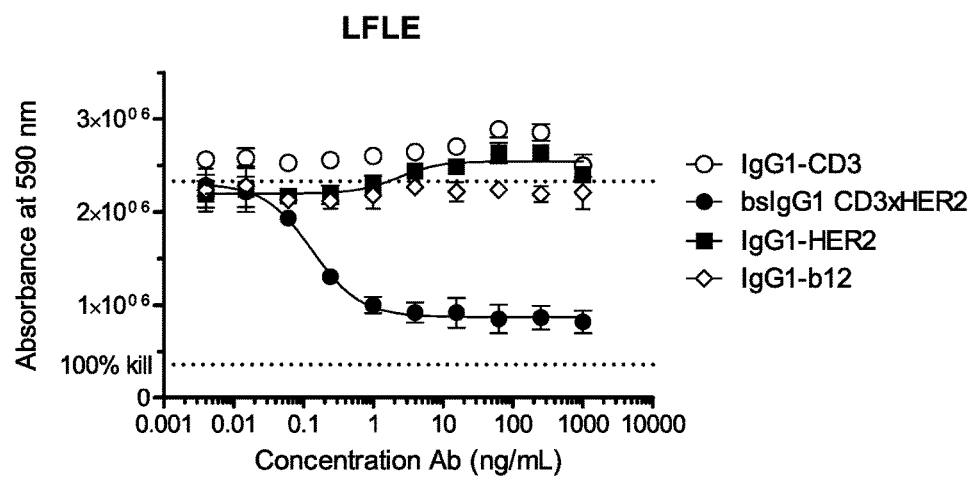
Figure 5D:
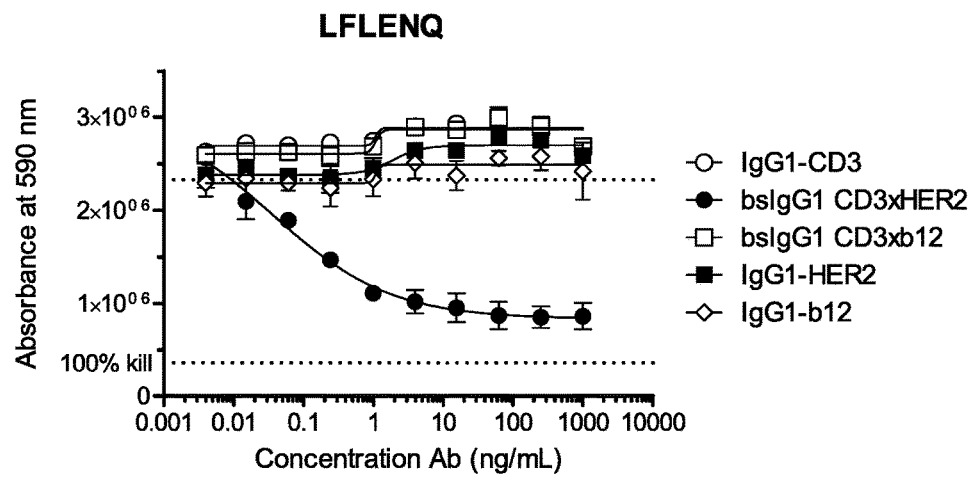
Figure 5E:
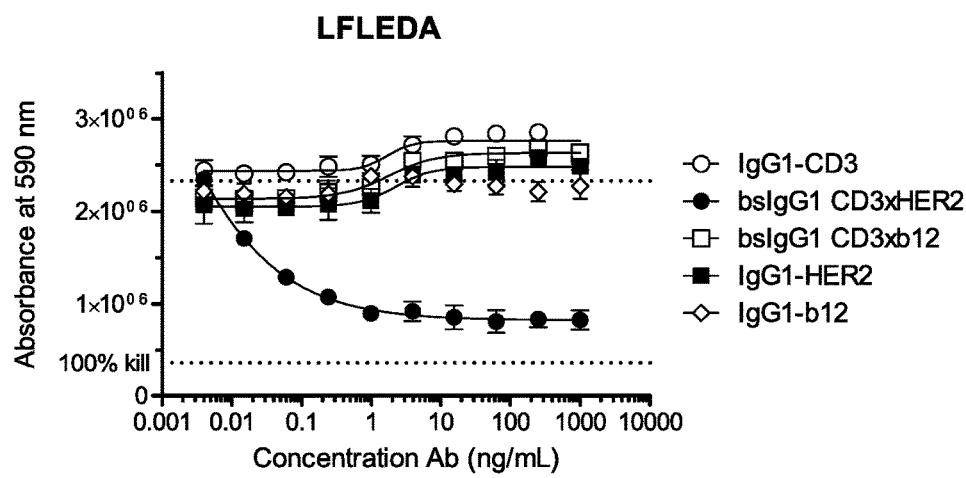
Figure 5F:
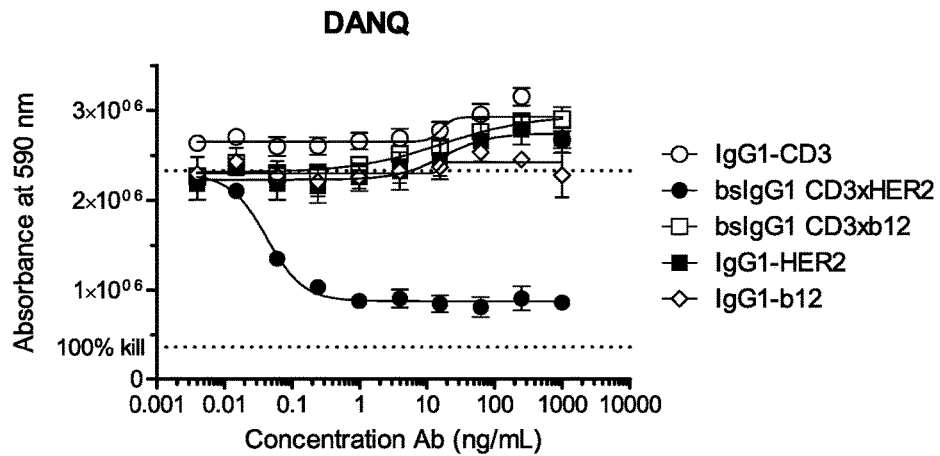
Figure 5G:
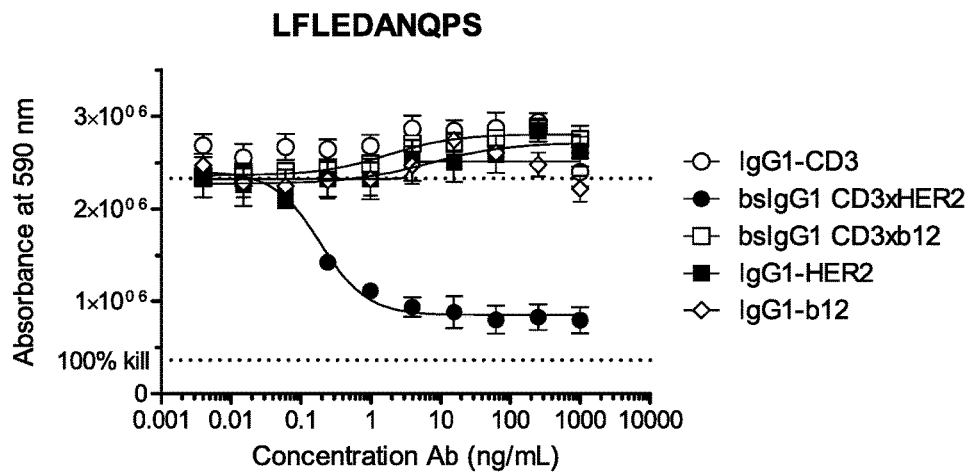

FIGS. 4A and 4B: T-cell proliferation measured in ELISA as described in Example 4. PBMCs were incubated with antibody variants for three days. Representative results from two independent experiments are shown.

FIGS. 5A-5G: Induction of T-cell mediated cytotoxicity by wild-type and antibody variants (N297Q, LFLE, LFLENQ, LFLEDA, DANQ, LFLEDANQPS [FIGS. 5A-5G]) was determined as described in Example 5. The averages from one experiment performed in duplet are shown.

Figure 6A:
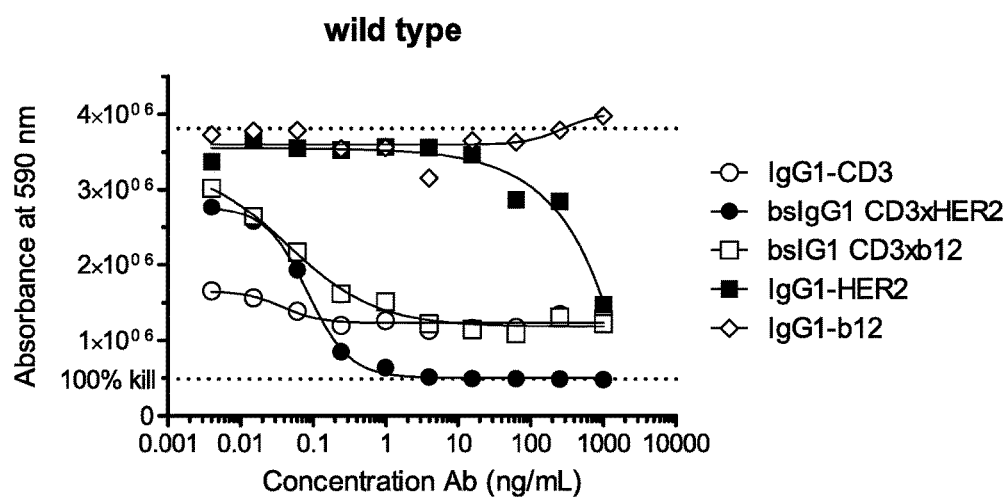
Figure 6B:
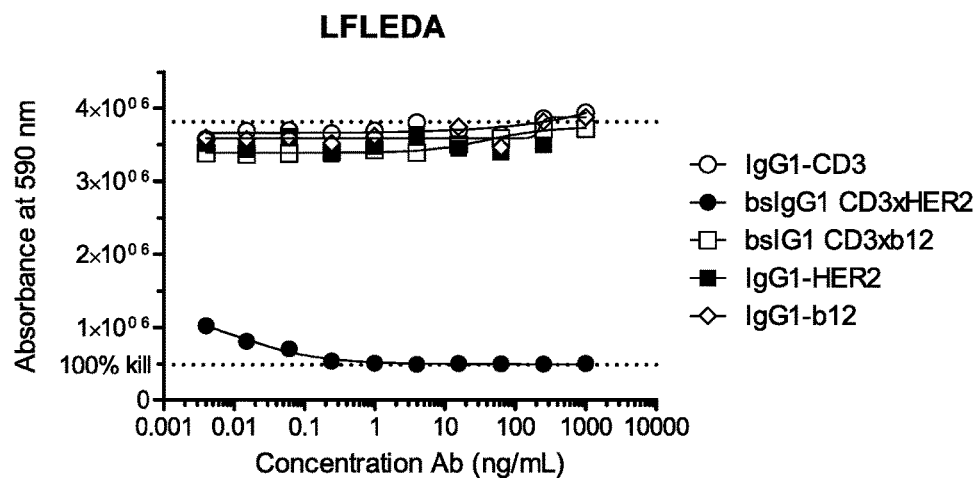
Figure 6C:
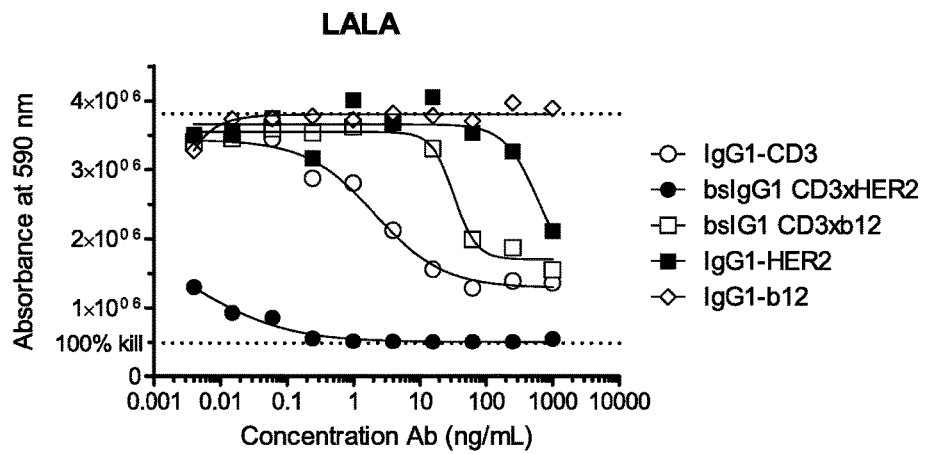
Figure 7A:
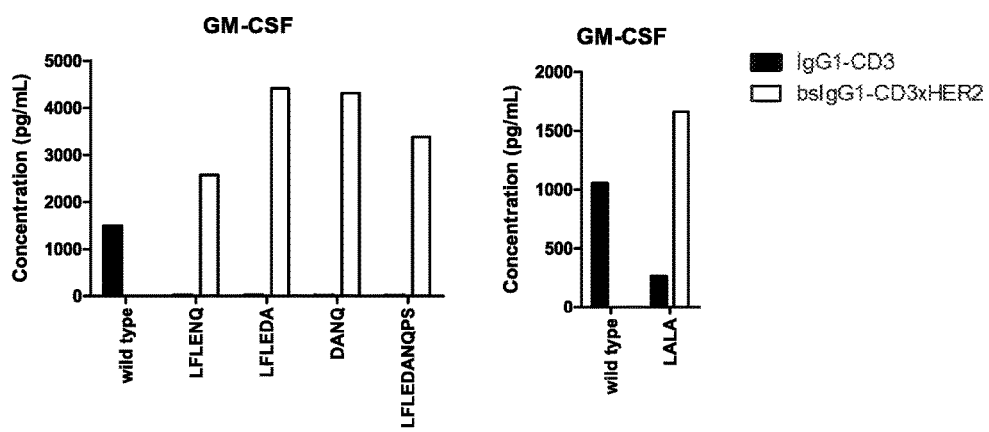
Figure 7B:
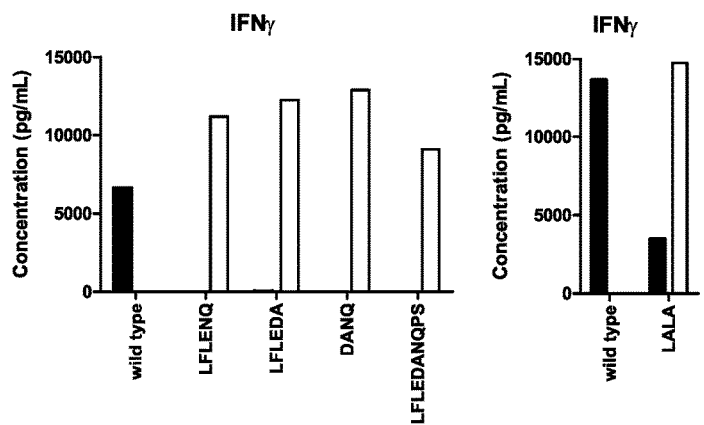
Figure 7C:
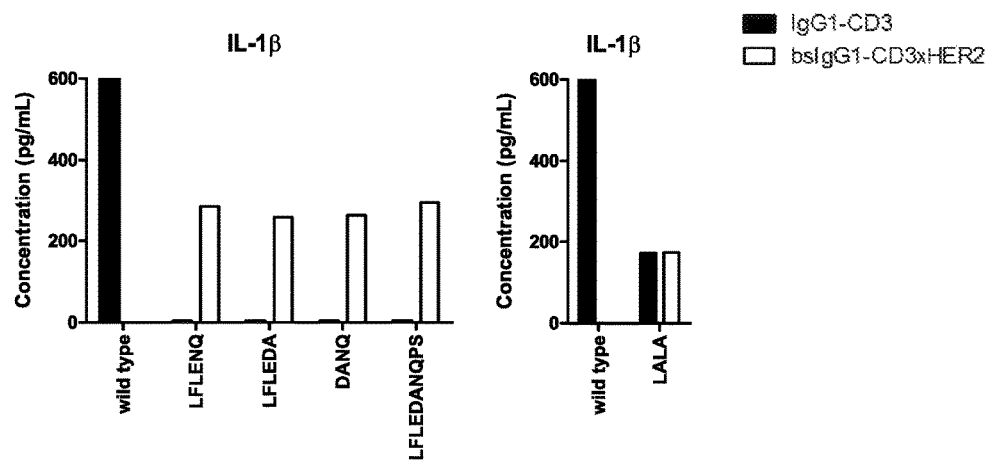
Figure 7D:
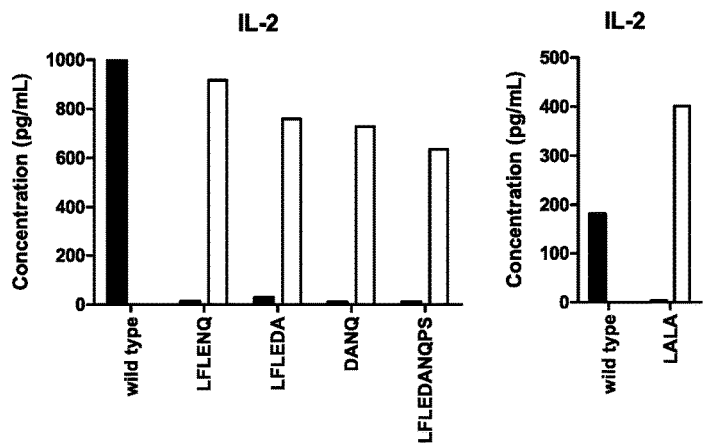
Figure 7E:
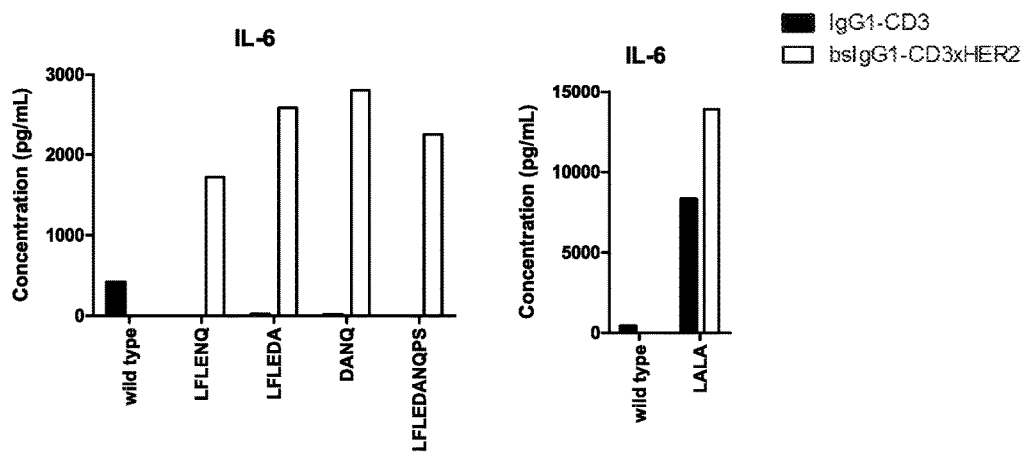
Figure 7F:
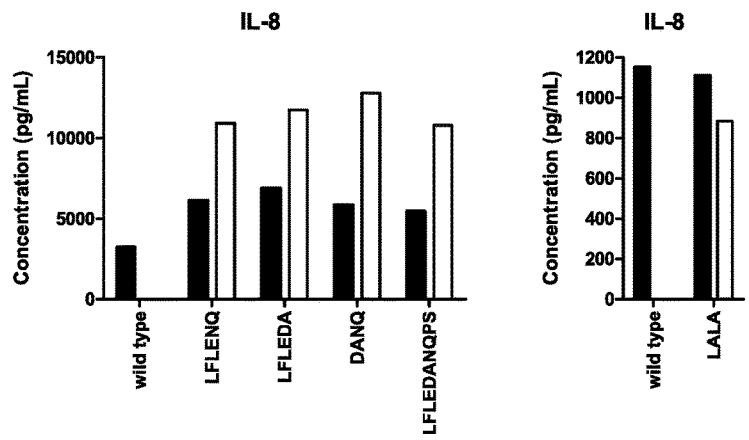
Figure 7G:
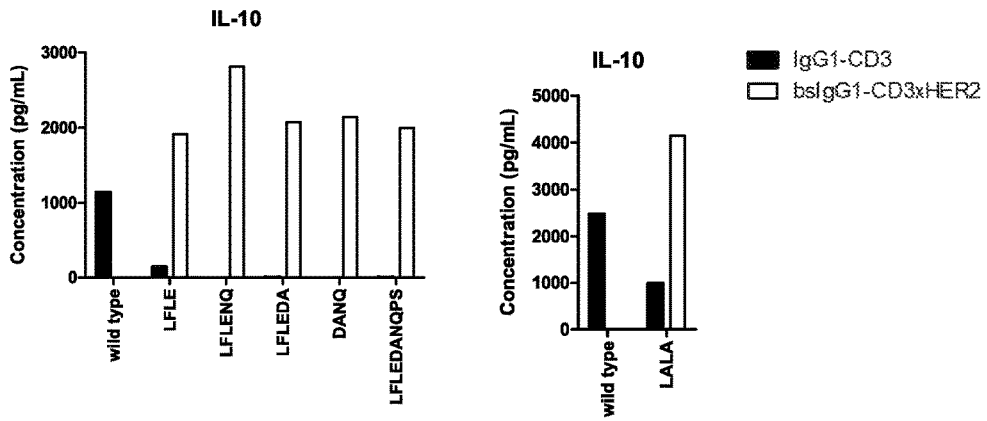
Figure 7H:
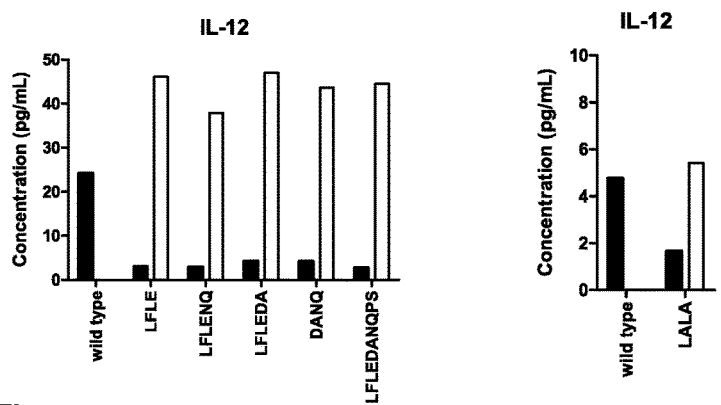
Figure 7I:
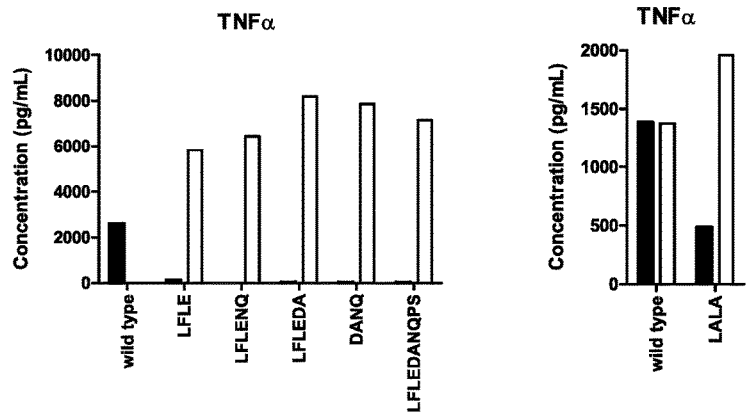
Figure 8A:
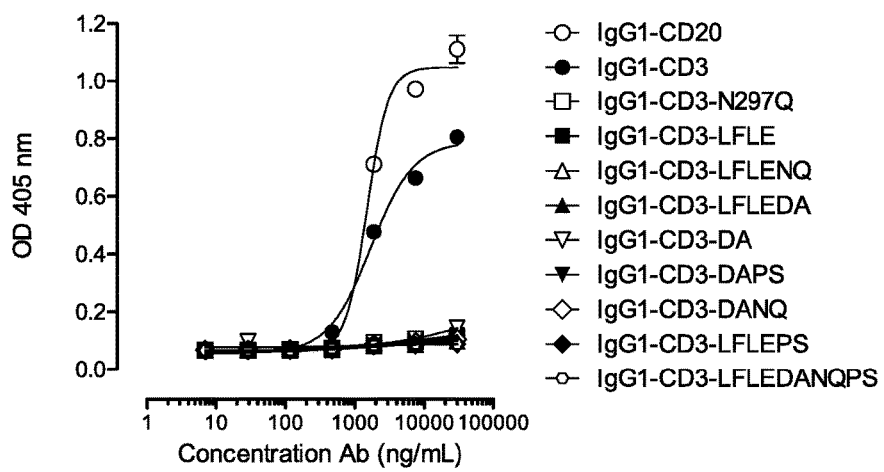
Figure 8B:
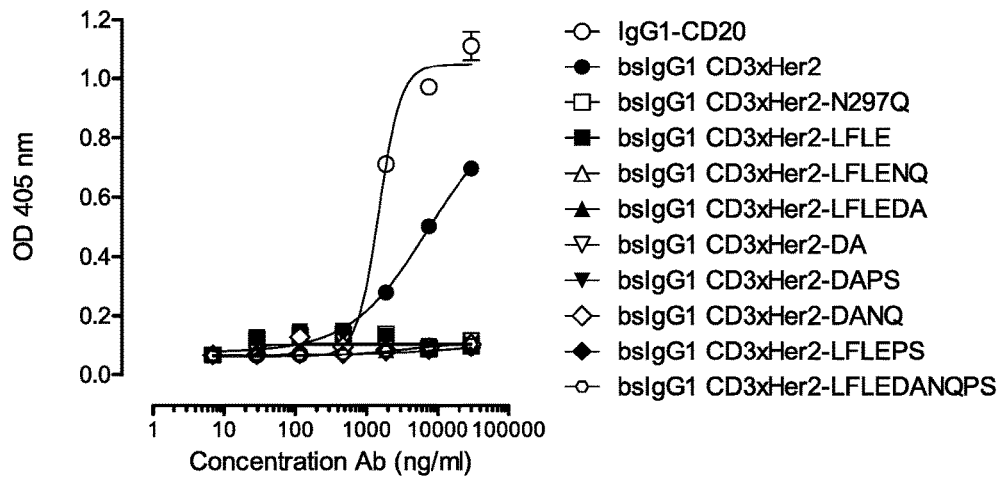
Figure 8C:
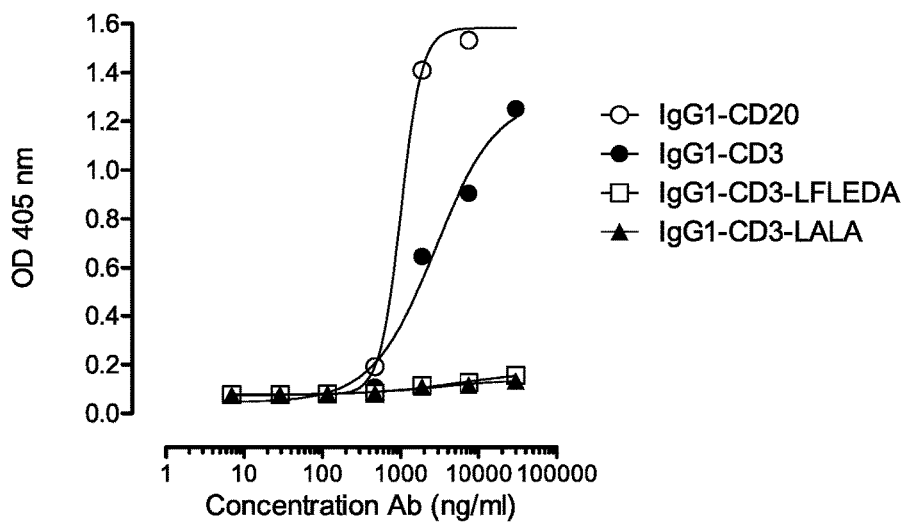
Figure 8D:
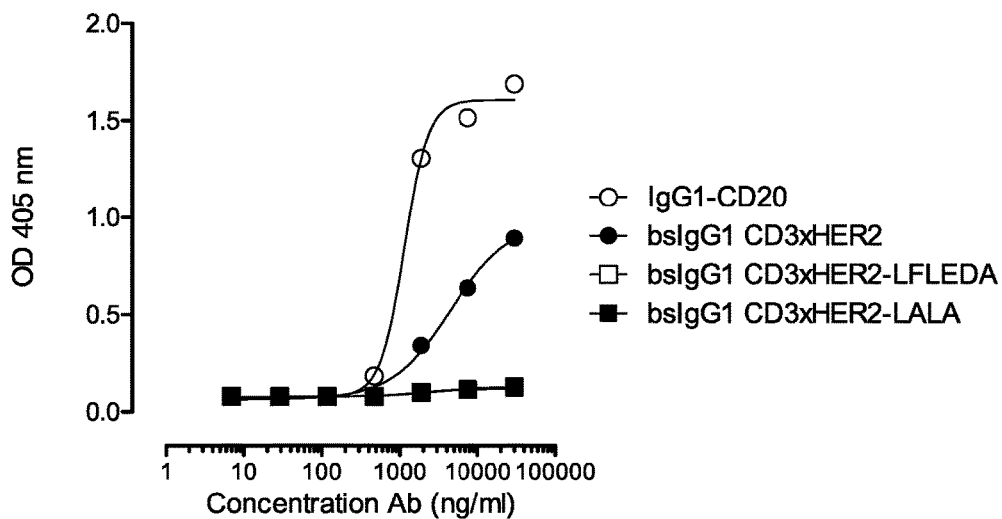

FIGS. 6A-6C: Induction of T-cell mediated cytotoxicity by wild-type and antibody variants (LFLEDA, LALA [FIGS. 6A-6C]) was determined as described in Example 5. The averages from two experiments performed in duplet are shown.

FIGS. 7A-7I: Cytokine release in supernatant upon incubation of tumor cells and PBMCs with non-activating monospecific IgG1-CD3 or bispecific IgG-CD3×HER2 antibody variants as described in Example 5 (incubation with GM-CSF (FIG. 7A), IFNγ (FIG. 7B), IL-1β (FIG. 7C), IL-2 (FIG. 7D), IL-6 (FIG. 7E), IL-8 (FIG. 7F), IL-10 (FIG. 7G), IL-12 (FIG. 7H), and TNFα (FIG. 7I)).

FIGS. 8A-8D: Binding of C1q to monospecific IgG1-CD3 (FIG. 8A, FIG. 8C) and bispecific IgG1-CD3×HER2 (FIG. 8B, FIG. 8D), and non-activating antibody variants thereof was evaluated by ELISA as described in Example 7. The results are representative for the experiments performed twice.

Figure 9A:
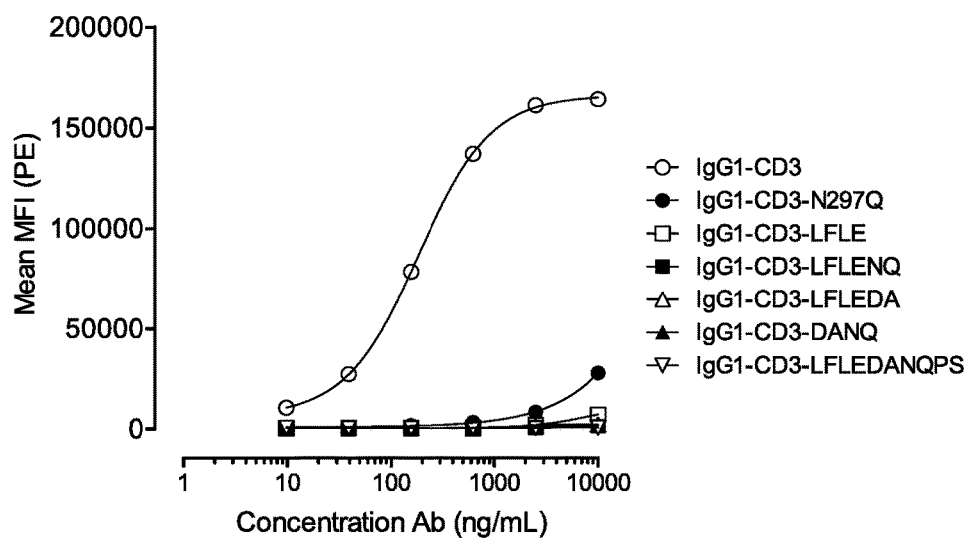
Figure 9B:
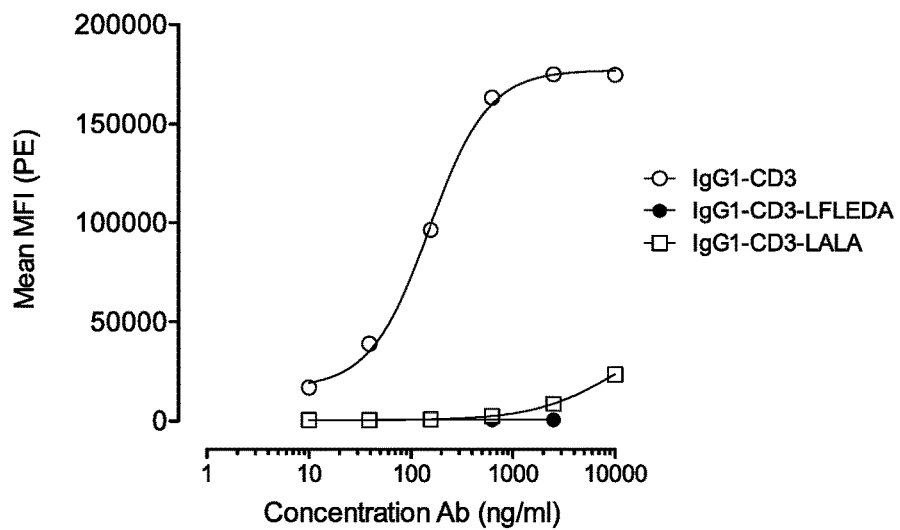

FIGS. 9A and 9B: Binding of IgG1-CD3 antibody variants (FIG. 9A) N297Q, LFLE, LFLEDA, LFLENQ, DANQ, and LFLEDANQPS and (FIG. 9B) LFLEDA and LALA to the high affinity FcγRI was evaluated by FACS analysis as described in Example 8. Averages of two experiments are shown.

Figure 10A:
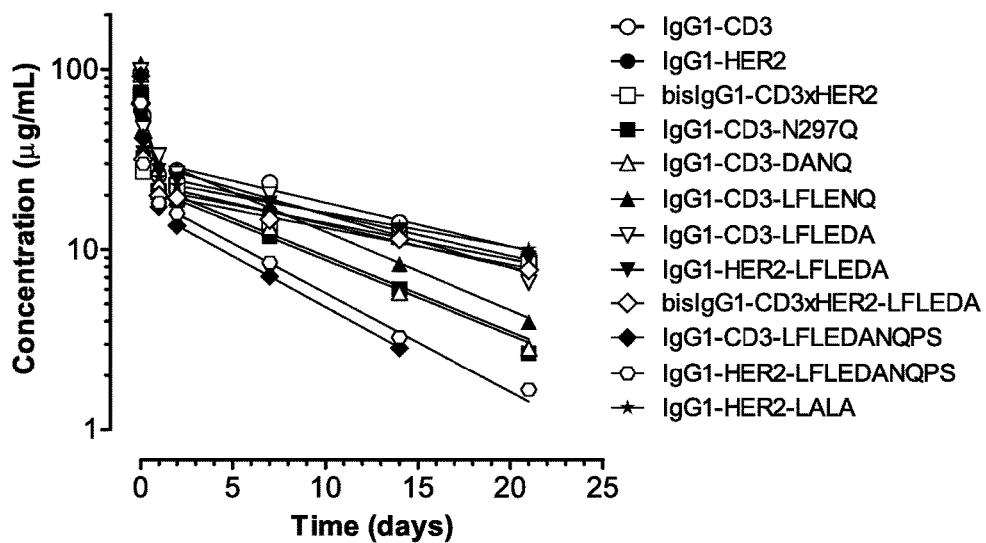
Figure 10B:
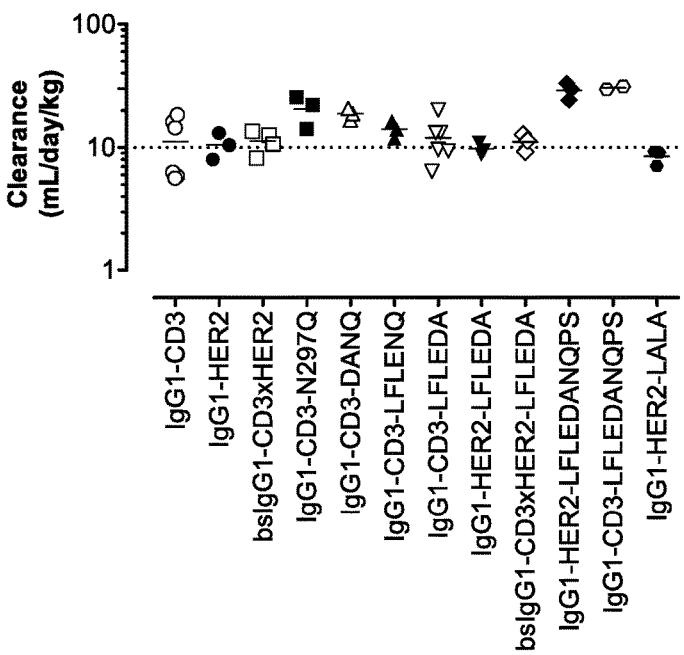

FIGS. 10A and 10B: Pharmacokinetic (PK) analysis of the non-activating antibody variants was compared to that of wild-type IgG1-CD3 antibody as described in Example 9. FIG. 10A shows the plasma concentration of human IgG1 plotted against time. FIG. 10B shows plasma clearance rate calculated as described in Example 9. The horizontal dotted line represents the average clearance rate of human IgG1 antibodies in SCID mice (10 mL/day/kg).

Figure 11A:
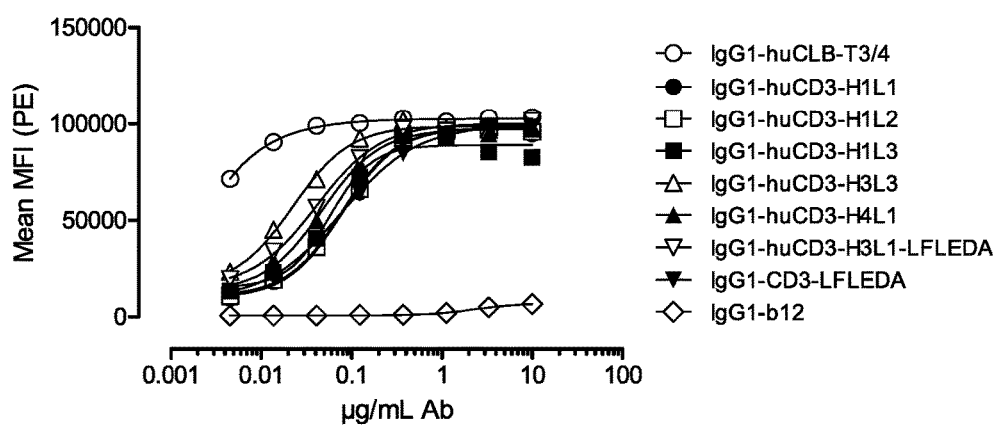
Figure 11B:
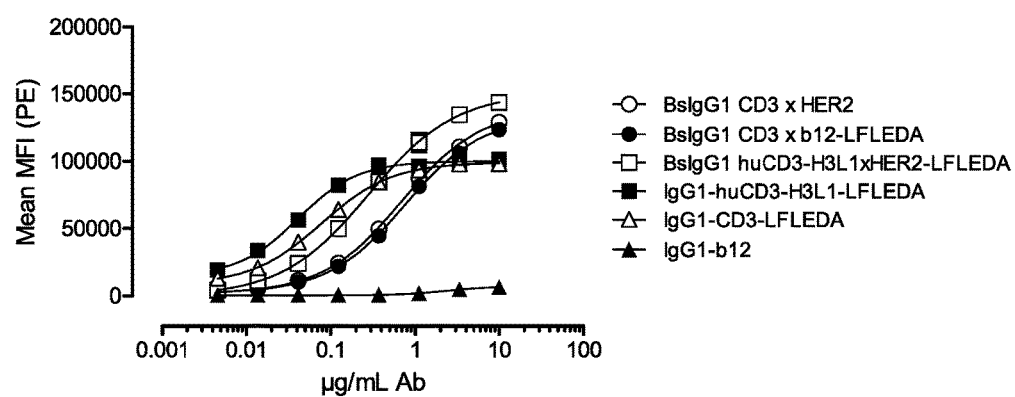

FIGS. 11A and 11B: Binding curves of (FIG. 11A) monospecific antibody variants of IgG1-huCD3 and (FIG. 11B) bispecific antibody variants bsIgG1 huCD3×HER2 to the human T-cell line Jurkat. Data shown are mean fluorescence intensities (MFI) of one representative experiment, as described in Example 10. The tables show the antibody concentrations (μg/mL) that result in half-maximal binding (EC50).

Figure 12A:
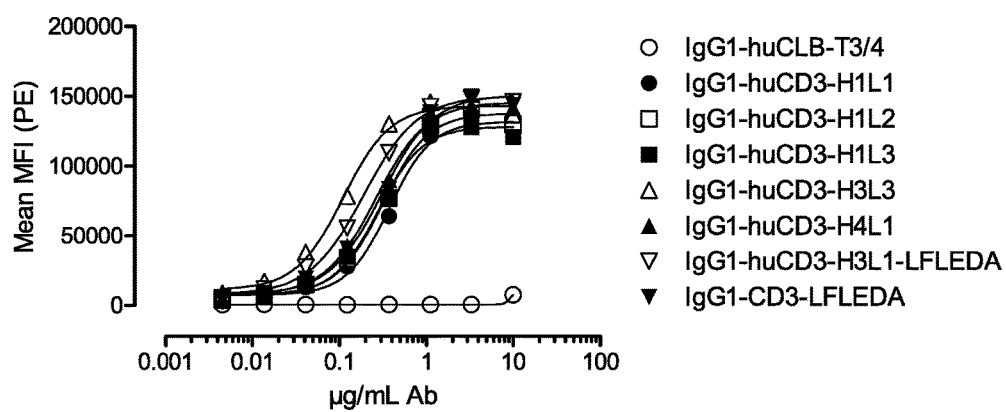
Figure 12B:
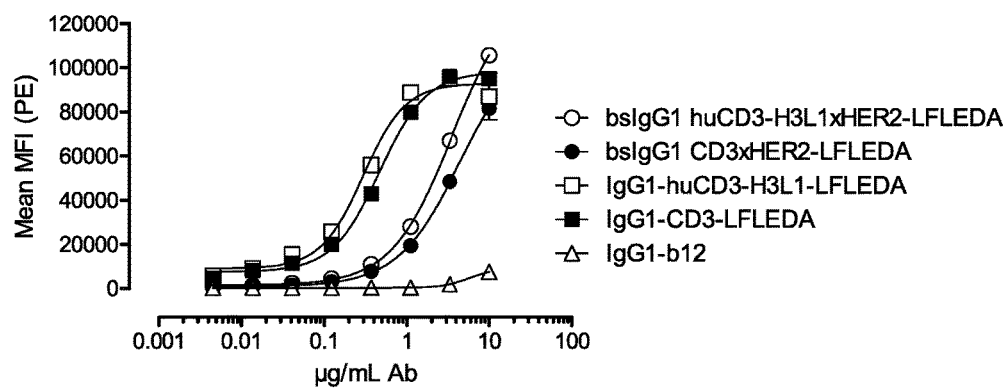

FIGS. 12A and 12B: Binding curves of (FIG. 12A) monospecific antibody variants of IgG1-huCD3 and (FIG. 12B) bispecific antibody variants bsIgG1 huCD3×HER2 to the cynomolgus T-cell line HCS-F. Data shown are mean fluorescence intensities (MFI) of one representative experiment, as described in Example 10.

Figure 13A:
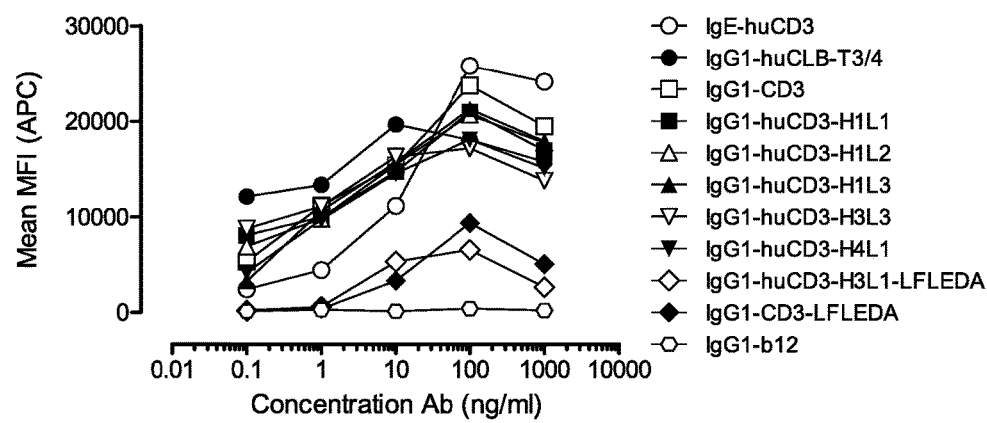
Figure 13B:
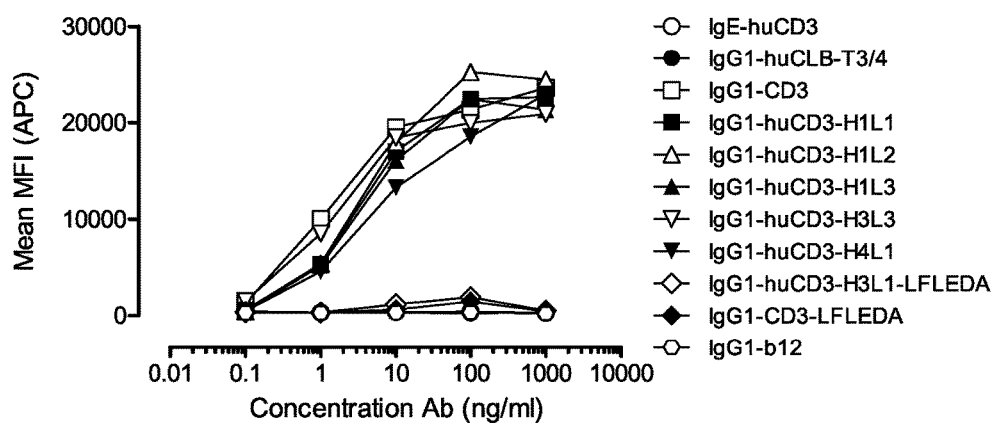

FIGS. 13A and 13B: IgG1-huCD3 antibody variants were titrated on PBMCs. Expression of CD69 on T-cells in PBMC culture was measured by FACS analysis, as described in Example 11. These experiments were performed twice and representative results from one experiment are shown.

Figure 14A:
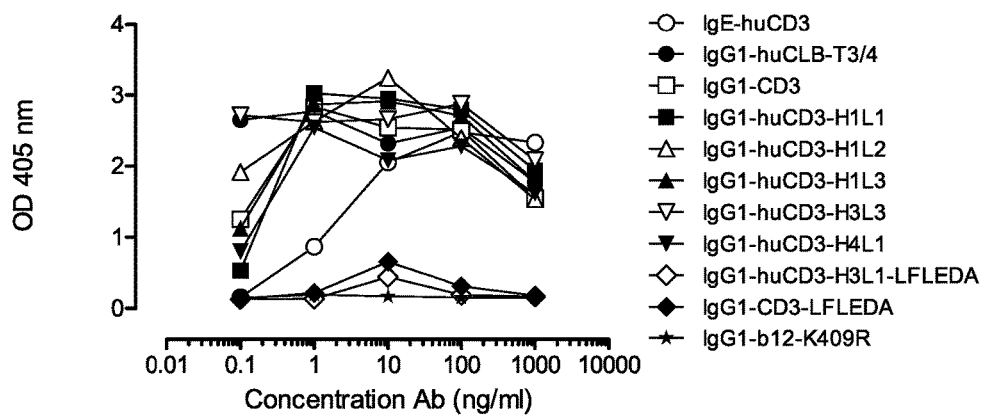
Figure 14B:
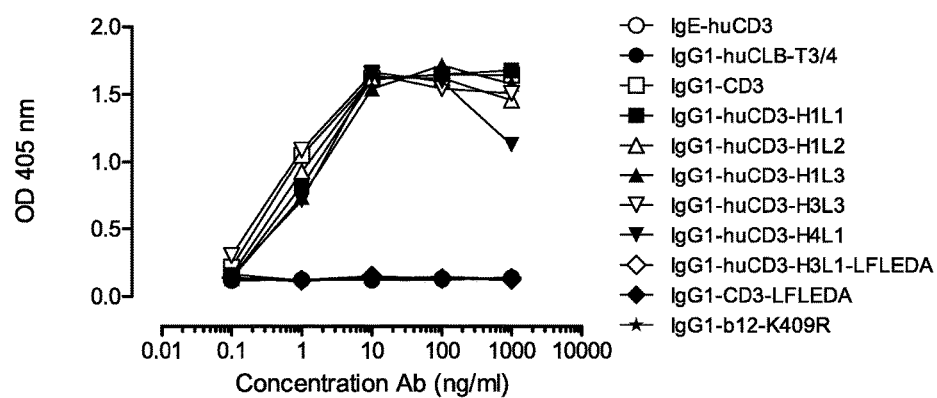

FIGS. 14A and 14B: Human (FIG. 14A) or cynomolgous (FIG. 14B) PBMCs were incubated with IgG1-huCD3 antibody variants for three days, after which proliferation was measured by a cell proliferation ELISA, as described in Example 12. Representative results from two independent experiments are shown.

Figure 15A:
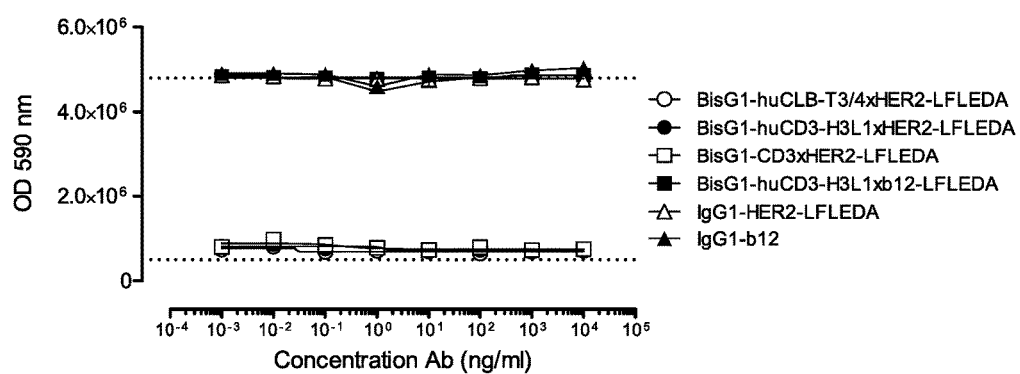
Figure 15B:
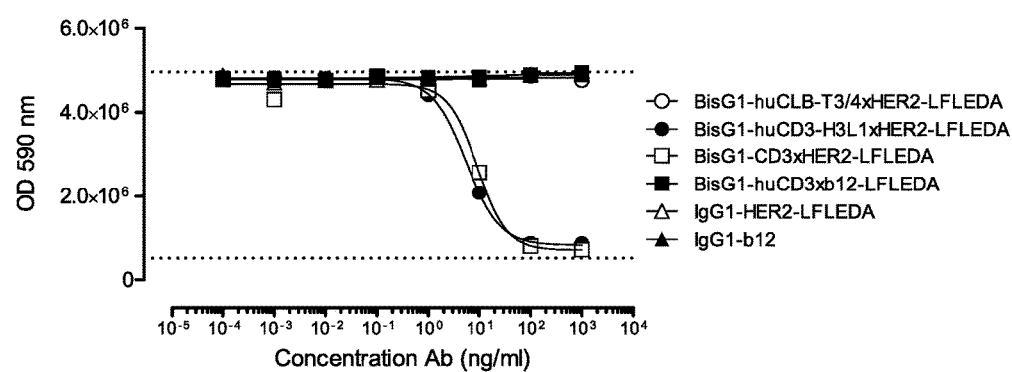

FIGS. 15A and 15B: Induction of human (FIG. 15A) and cynomolgus (FIG. 15B) T-cell-mediated cytotoxicity by humanized CD3 (huCD3) antibody variants with non-activating LFLEDA mutations were determined as explained in Example 13. Representative results from two independent experiments performed in duplets are shown.

DETAILED DESCRIPTION OF THE INVENTION

As described herein, specific modifications in amino acid positions in the Fc region of an antibody have proven to be non-activating modifications making the protein inert. Specifically, it has been shown that a particular embodiment has an in vivo plasma clearance rate comparable to the plasma clearance rate of the wild-type antibody.

The term "non-activating" as used herein, is intended to refer to the inhibition or abolishment of the interaction of the protein according to the invention with Fc Receptors (FcRs) present on a wide range of effector cells, such as monocytes, or with C1q to activate the complement pathway.

The term "Fc region" as used herein, is intended to refer to a region comprising, in the direction from the N- to C-terminal, at least a hinge region, a CH2 region and a CH3 region.

The present invention relates in one aspect to a protein comprising a first polypeptide and a second polypeptide, wherein said first and second polypeptide each comprises at least a hinge region, a CH2 region and a CH3 region of an immunoglobulin heavy chain, wherein in at least one of said first and second polypeptide the amino acids in the positions corresponding to positions L234, L235 and D265 in a human IgG1 heavy chain, are not L, L, and D, respectively.

The term "protein" as used herein is intended to refer to large biological molecules comprising one or more chains of amino acids linked to one another by peptide bonds. A single chain of amino acids may also be termed "polypeptide". Thus, a protein in the context of the present invention may consist of one or more polypeptides. The protein according to the invention may be any type of protein, such as an antibody or a variant of a parent antibody.

The term "antibody" as used herein is intended to refer to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The binding region (or binding domain which may be used herein, both having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab A/S); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

When the antibody is a fragment, such as a binding fragment, it is to be understood within the context of the present invention that said fragment is fused to an Fc region as herein described. Thereby, the antibody may be a fusion protein which falls within the scope of the invention. Thus, in one embodiment, the protein is a fusion protein.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Lefranc M P et al, Dev Comp Immunol January: 27(1):55-77 (2003)).

The term "full-length antibody" as used herein, refers to an antibody (e.g., a parent or variant antibody) which contains all heavy and light chain constant and variable domains corresponding to those that are normally found in a wild-type antibody of that isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "first polypeptide" and "second polypeptide" as used herein refers to a set of polypeptides which may be identical or different in amino acid sequence. Unless otherwise stated or indicated in case of a wild-type protein, the first and second polypeptides have identical amino acid sequences.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f)) that is encoded by heavy chain constant region genes. Thus, in one embodiment, the protein comprises a heavy chain of an immunoglobulin of the IgG1 class or any allotype thereof. Further, each heavy chain isotype can be combined with either a kappa (κ) or lambda (λ) light chain, or any allotypes thereof.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat (described in Kabat, E. A. et al., Sequences of proteins of immunological interest. 5th Edition—US Department of Health and Human Services, NIH publication No. 91-3242, pp 662,680,689 (1991)).

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering system. However, the CH2 region may also be any of the other subtypes as described herein.

The term "CH3 region" or "CH3 domain" as used herein refers to the CH3 region of an immunoglobulin heavy chain. Thus, for example the CH3 region of a human IgG1 antibody corresponds to amino acids 341-447 according to the Eu numbering system. However, the CH3 region may also be any of the other subtypes as described herein.

The term "amino acid corresponding to positions" as used herein refers to an amino acid position number in a human IgG1 heavy chain. Unless otherwise stated or contradicted by context, the amino acids of the constant region sequences are herein numbered according to the Eu-index of numbering (described in Kabat, E. A. et al., Sequences of proteins of immunological interest. 5th Edition—US Department of Health and Human Services, NIH publication No. 91-3242, pp 662,680,689 (1991)). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

In the context of the present invention, the amino acid may be defined by a conservative or non-conservative class. Thus, classes of amino acids may be reflected in one or more of the following tables:

| Amino acid residue of conservative class | |
| --- | --- |
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| Alternative Physical and Functional Classifications of Amino Acid Residues | |
| --- | --- |
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present invention, a substitution in a protein is indicated as:

Original amino acid-position-substituted amino acid;

Referring to the well-recognized nomenclature for amino acids, the three letter code, or one letter code, is used, including the codes Xaa and X to indicate any amino acid residue. Accordingly, the notation "L234F" or "Leu234Phe" means, that the protein comprises a substitution of Leucine with Phenylalanine in the protein amino acid position corresponding to the amino acid in position 234 in the wild-type protein.

Substitution of an amino acid at a given position to any other amino acid is referred to as:

Original amino acid-position; or e.g. "L234".

For a modification where the original amino acid(s) and/or substituted amino acid(s) may comprise more than one, but not all amino acid(s), the more than one amino acid may be separated by "," or "/". E.g. the substitution of Leucine for Phenylalanine, Arginine, Lysine or Tryptophan in position 234 is:

"Leu234Phe, Arg, Lys, Trp" or "L234F, R, K, W" or "L234F/R/K/W" or "L234 to F, R, K or W"

Such designation may be used interchangeably in the context of the invention but have the same meaning and purpose.

Furthermore, the term "a substitution" embraces a substitution into any one of the other nineteen natural amino acids, or into other amino acids, such as non-natural amino acids. For example, a substitution of amino acid L in position 234 includes each of the following substitutions: 234A, 234C, 234D, 234E, 234F, 234G, 234H, 234I, 234K, 234M, 234N, 234Q, 234R, 234S, 234T, 234V, 234W, 234P, and 234Y. This is, by the way, equivalent to the designation 234X, wherein the X designates any amino acid other than the original amino acid. These substitutions can also be designated L234A, L234C, etc., or L234A,C, etc., or L234A/C/etc. The same applies by analogy to each and every position mentioned herein, to specifically include herein any one of such substitutions. It is well-known in the art when an amino acid sequence comprises an "X" or "Xaa", said X or Xaa represents any amino acid. Thus, X or Xaa may typically represent any of the 20 naturally occurring amino acids. The term "naturally occurring" as used herein, refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine.

The terms "amino acid" and "amino acid residue" may be used interchangeably.

In one embodiment, in at least one of said first and second polypeptides the amino acid in the positions corresponding to positions L234, L235 and D265 in a human IgG1 heavy chain, are not L, L, and D, respectively, and wherein the amino acids in the positions corresponding to positions N297 and P331 in a human IgG1 heavy chain are not Q and S, respectively.

In one embodiment, in at least one of said first and second polypeptides the amino acid in the positions corresponding to positions L234, L235 and D265 in a human IgG1 heavy chain, is not L, L, and D, respectively, and wherein the amino acids in the positions corresponding to positions N297 and P331 in a human IgG1 heavy chain have not been substituted. In this context, the term "have not been substituted" refers to the amino acids in the amino acid positions N297 and P331 in a human IgG1 heavy chain which have not been substituted with another naturally or non-naturally occurring amino acid. Thus, a "have not been substituted" amino acid in a position corresponding to the position in a human IgG1 heavy chain means the amino acid at the particular position is the same as the naturally occurring amino acid in a human IgG1 heavy chain.

Fc-mediated effector functions form a part of the biological activity of human immunoglobulin G (IgG) molecules. Examples of such effector functions include e.g. antibody-dependent cell-mediated cytotoxicity (ADCC) and complement-dependent cytotoxicity (CDC) which are triggered by the binding of various effector molecules to the Fc region. In the context of the present invention, "Fc binding", "Fc Receptor binding", "FcR binding", and "binding of an antibody Fc region to FcR" refers to the binding of the Fc region to an Fc Receptor (FcR) or an effector molecule. The terms "FcγR binding" and "FcγRI binding" refers to binding to or with an Fc region to the Fc gamma Receptor and Fc gamma Receptor I, respectively. In some cases, when a CD3 antibody binds T-cells the Fc region of the CD3 antibody binds to FcRs present on other cells, e.g. monocytes, which leads to activation of the T-cell. Such non-targeted activation of T-cells may be undesired. However, targeted T-cell activation may be highly desirable for the treatment of a range of indications, such as cancer. Targeting of T-cells to specific cells, e.g. tumor cells, may be facilitated by use of a bispecific antibody, wherein one of the binding regions binds CD3 present on the T-cell and the other binding region binds a target specific antigen, e.g. on a tumor cell. Undesired targeted T-cell activation via Fc-mediated cross-linking should be avoided and may be disabled by making the Fc region inert for such activity. Thereby, interaction between said inert Fc region with Fc Receptors present is prevented. An antibody of the present invention has been proven to be completely inert when tested in several different assays, i.e. see Examples 3 to 9 and 11 to 13. The CD3 antibody comprising the amino acid substitutions L234F, L235E, and D265A, as described in the Examples, showed abrogation of Fc-mediated T-cell proliferation, Fc-mediated CD69 expression on T-cells, unspecific killing and cytokine release in a cytotoxicity assay, as well as in vitro C1q binding. Similarly, the antibody comprising the amino acid substitutions L234F, L235E, and N297Q showed comparable results. Thus, a protein, such as an antibody, of the present invention clearly shows superior results in several assays when compared to a wild-type protein.

The term "inertness", "inert" or "non-activating" as used herein, refers to an Fc region which is at least not able to bind any Fcγ Receptors, induce Fc-mediated cross-linking of FcRs, or induce FcR-mediated cross-linking of target antigens via two Fc regions of individual proteins, such as antibodies, or is not able to bind C1q.

The term "cross-linking" as used herein, refers to the bridging of two proteins, which may be surface proteins, by the bivalent interaction of an antibody or the bridging of two proteins that are bound by antibodies through interaction of the antibody Fc-regions with an FcR-bearing cell or the bridging of Fc Receptors to which antibodies are bound through interaction of the antibody with their target antigen on target antigen-bearing cells.

The term "unspecific killing" as used herein, refers to the killing of cells by the cytotoxic function of T-cells or other effector cells, through tumor target antigen-independent activation of said cells.

The term "proliferation" as used herein, refers to cell growth in the contexts of cell development and cell division.

Thus, the present invention relates to a protein which does not enable Fc-mediated T-cell activation, does not induce the complement system, does not bind Fcγ Receptors, but at the same time have a plasma clearance rate which is comparable to the plasma clearance rate of a wild-type protein. Such a protein may also be used in a bispecific format.

Thus, in one embodiment, the protein has a plasma clearance rate which deviates from a wild-type protein by no more than 10%, such as no more than 8%, no more than 7%, no more than 5%, no more than 3%, no more than 1%, and no more than 0%.

In a particular embodiment, the protein has a plasma clearance rate (mL/day/kg) which deviates from a wild-type protein by no more than 10%, such as no more than 8%, no more than 7%, no more than 5%, no more than 3%, no more than 1%, and no more than 0% wherein the plasma clearance rate is calculated by the dose (μg/kg) administered to a subject divided by the area under the curve (AUC), wherein the AUC value is determined from concentration-time curves.

In a particular embodiment, the protein has a plasma clearance rate which deviates from a wild-type protein by no more than 10%, such as no more than 8%, no more than 7%, no more than 5%, no more than 3%, no more than 1%, and no more than 0% when the plasma clearance rate (mL/day/kg) is calculated based on absorbance at 405 nm measured in a quantitative ELISA assay wherein the test samples are blood samples, such as blood serum.

The term "quantitative ELISA" as used herein, refers to an ELISA which allows evaluating whether a certain protein is present or absent within a sample and at the same time provides a concentration value for the protein within the sample. In order to carry out quantitative ELISA, an accurate standard curve must be generated to determine protein concentrations in the samples. A standard curve is typically a serial dilution of a known-concentration solution of the target molecule. Thus, in quantitative ELISA, the optical density (OD) of the sample is compared to the standard curve.

In a particular embodiment, the protein has a plasma clearance rate which deviates from a wild-type protein by no more than 10%, such as no more than 8%, no more than 7%, no more than 5%, no more than 3%, no more than 1%, and no more than 0% when the plasma clearance rate (mL/day/kg) is calculated based on absorbance at 405 nm measured in a quantitative ELISA assay comprising the steps of (i) a capture antibody, such as anti-human IgG-kappa antibody, (ii) a detecting antibody recognizing the protein, such as anti-human IgG-HRP antibody.

The term "capture antibody" as used herein refers to an unlabeled antibody which is coated to the ELISA plate. The capture antibody is used to detect/capture the protein of interest from a sample to be measured.

The term "detecting antibody" as used herein refers to a labeled antibody which is used to detect the protein of interest, which is bound to the capture antibody. The label consists of an enzyme that can catalyze the conversion of a chromogenic substrate into colored products. The colored product can be quantified by measuring at a specific OD, typically around 405 nm depending on the chromogenic substrate.

In a particular embodiment, the protein has a plasma clearance rate which deviates from a wild-type protein by no more than 10%, such as no more than 8%, no more than 7%, no more than 5%, no more than 3%, no more than 1%, and no more than 0% when the plasma clearance rate (mL/day/kg) is calculated based on absorbance at 405 nm measured in an ELISA assay comprising the steps of (i) coating an ELISA plate with mouse-anti-human IgG-kappa antibody, (II) blocking with 0.2% BSA/PBS, (iii) incubating with dilutions of blood samples, (iv) washing the plates, (v) incubating with goat-anti-human IgG-HRP antibody, (vi) developing the plates with 1 mg/mL 2,2'-azino-bis (3-ethylbenzothiazoline-6-sulfonic acid), and (vii) adding 100 µL 2% oxalic acid to stop the reaction.

The term "plasma clearance rate" as used herein, refers to a quantitative measure of the rate at which a protein is removed from the blood upon administration to a living organism. Evaluation of the plasma clearance of the antibodies may be evaluated in SCID mice, as described in Example 9. Thus, in one embodiment, the plasma clearance rate is measured by an assay comprising the steps of injecting 7-10 weeks old C.B-17 SCID mice (CB17/Icr-Prkdcscid/IcrIcoCrl, Charles-River) with a single i.v. dose of 100 µg (5 mg/kg) of antibody, taking blood samples with regular time intervals, collecting blood into heparin containing vials, centrifuging for 5 minutes at 10,000×g, coating 96-well ELISA plates overnight at 4° C. with mouse-anti-human IgG-kappa antibody in PBS, washing plates, blocking with 0.2% BSA/PBS for 1 hr at room temperature, incubating with dilutions (1/50 to 1/2400 in 0.2% BSA/PBST) of the blood samples or a standard curve for 1 hr at room temperature, washing plates with PBST, incubating with a goat-anti-human IgG-HRP antibody for 1 hr at room temperature, developing for about 30 min with 1 mg/mL 2,2'-azino-bis (3-ethylbenzothiazoline-6-sulfonic acid), adding 100 µL 2% oxalic acid thereby stopping the reaction, measuring absorbance at 405 nm in a suitable microplate reader, quantifying the antibody, plotting the antibody plasma concentration (µg/mL) over time (days) in a graph, and calculating plasma clearance rates (mL/day/kg).

The plasma clearance rate (mL/day/kg) may be calculated based on the area under the curve (AUC) according to the following equation;

$$\text{Plasma clearance} = \frac{\text{Dose}(\mu g/kg)}{AUC(\mu g/mL/day)}$$

wherein the AUC value is determined from the concentration-time curves.

The term "deviates" as used herein when referring to the plasma clearance rate, refers to a difference in the quantitative measure of the rate the protein is removed from the blood upon administration to a living organism compared to the plasma clearance rate of a wild-type protein. Thus, the deviation or difference may be given as a percentage difference.

The term "wild-type" as used herein in relation to the comparison of a protein of the present invention, refers to a protein which is identical to the protein of the present invention to which it is being compared with except for the three amino acid positions according to the present invention. The wild-type protein comprises the naturally occurring amino acids of the polypeptide chains at the amino acid positions of the three modifications of the present invention, i.e. a protein that does not comprise the amino acid modifications according to the invention. Specifically, a wild-type antibody in relation to the invention comprises a Leucine at positions 234 and 235, and Aspartic acid at position 265 when the antibody is an IgG1 antibody. Thus, a wild-type protein, such as an antibody, will remain an activating protein, which is able to bind e.g. Fcγ Receptors. A wild-type protein and a protein according to the invention may comprise other amino acid modifications than those of the invention, e.g., in order to make the protein bispecific, or the like. Thus, "wild-type" specifically refers to the amino acids in positions corresponding to positions 234, 235 and 265 in a human IgG1 heavy chain, wherein the amino acids have not been substituted to any other amino acid than naturally occurring amino acids in said positions.

The term "ELISA" as used herein refers to enzyme-linked immunosorbent assay which is a test that uses antibodies and color change to identify a substance. A first specific antibody is attached to the plate surface. Thereby the protein from a sample is added wherein binding to said first specific antibody is tested. A second antibody binding the protein from the sample is added. The second antibody is linked to an enzyme, and, in the final step, a substance containing the enzyme's substrate is added. The subsequent reaction produces a detectable signal, most commonly a color change in the substrate. The concept of the ELISA method is well-known within the art and various ways of performing an ELISA are contemplated to be part of a method to evaluate the protein according to the invention may be evaluated with. Thus, this interpretation is not to be understood as limiting as various forms of ELISAs may be performed such as described in Examples 4 or 5.

As used herein, the term "subject" is typically a human which respond to the protein of the invention.

As can be seen in Example 9, the antibody comprising an amino acid substitution in the amino acid positions corresponding to L234, L235, and D265, respectively, in a human IgG1 heavy chain, showed a comparable plasma clearance rate to the wild-type antibody which was not expected. Another tested antibody comprising the amino acid substitutions L234F, L235E, and N297Q, which showed comparable results when testing T-cell activation, T-cell proliferation, unspecific killing, cytokine release and C1q, did not have comparable plasma clearance rate to the wild-type antibody. The same was observed for an antibody comprising only the amino acid substitution L234F and L235E, an antibody comprising the amino acid substitutions L234F, L235E, D265A, N297Q, and P331S, and an antibody comprising the amino acid substitutions D265A and N297Q.

In one embodiment, the first and second polypeptide is a first and a second heavy chain of an immunoglobulin, respectively.

In the embodiments, wherein the protein is an antibody, the first and second polypeptides will have the same purpose and meaning as a first and a second immunoglobulin heavy chain of an antibody. Thus, in such embodiments, the first polypeptide and second polypeptide are to be understood as the first heavy chain and the second heavy chain, respectively, of the antibody.

In one embodiment, the first and second polypeptide further comprises a first and a second binding region, respectively.

The term "binding region" as used herein, refers to a region of a protein which is capable of binding to any molecule, such as a polypeptide, e.g. present on a cell, bacterium, or virion. The binding region may be a polypeptide sequence, such as a protein, protein ligand, receptor, an antigen-binding region, or a ligand-binding region capable of binding to a cell, bacterium, or virion. Specifically, the binding region is an antigen-binding region. If the binding region is e.g. a receptor the protein may have been prepared as a fusion protein of an Fc-domain of an immunoglobulin and said receptor. If the binding region is an antigen-binding region the protein may be an antibody, like a chimeric, humanized, or human antibody or a heavy chain only antibody or a ScFv-Fc-fusion.

The term "binding" as used herein refers to the binding of a protein to a predetermined antigen or target, such as a receptor, to which binding typically is with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the protein as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the protein, so that when the $K_D$ of the protein is very low (that is, the protein is highly specific), then the amount with which the affinity for the antigen is lower than the affinity for a non-specific antigen may be at least 10,000 fold. The term "$K_D$" (M), as used herein, refers to the dissociation equilibrium constant of a particular antibody-antigen interaction.

The term "$K_D$" (M) as used herein, refers to the dissociation equilibrium constant of a particular antibody-antigen interaction.

The term "$K_A$" ($M^{-1}$) as used herein, refers to the association equilibrium constant of a particular antibody-antigen interaction and is obtained by dividing the $k_a$ by the $k_d$.

The term "$k_d$" ($sec^{-1}$) as used herein, refers to the dissociation rate constant of a particular antibody-antigen interaction. Said value is also referred to as the $k_{off}$ value.

The term "$k_a$" ($M^{-1} \times sec^{-1}$) as used herein, refers to the association rate constant of a particular antibody-antigen interaction.

In one embodiment, the protein further comprises a first and a second light chain of an immunoglobulin, wherein said first light chain is connected with said first heavy chain via disulfide bridges and said second light chain is connected with said second heavy chain via disulfide bridges, thereby forming a first binding region and a second binding region, respectively.

The term "disulfide bridges" as used herein refers to the covalent bond between two Cysteine residues, i.e. said interaction may also be designated a Cys-Cys interaction.

The protein according to the present invention may be monospecific, which in the context of the present invention refers to a protein which binds to the same epitope with its binding regions. However, the invention is not limited to monospecific proteins but also relates to multispecific proteins, such as bispecific proteins. Thus, in one embodiment, at least one of the first and second binding regions bind CD3. In a particular embodiment, said first binding region binds CD3 and said second binding region binds any other target of interest. Such other target may be a tumor-specific target or a cancer-specific target.

The term "human CD3" as used herein, refers to the human Cluster of Differentiation 3 which is part of the T-cell co-receptor protein complex and is composed of four distinct chains. In mammals, the complex contains a CD3γ (gamma) chain (human CD3γ chain 182 amino acids, Swissprot P09693, and cyno CD3γ 181 amino acids, Swissprot Q95LI7), a CD3δ (delta) chain (171 amino acids, human CD3δ Swissprot P04234 SEQ ID NO:14, and cyno CD3δ Swissprot Q95LI8), two CD3ε (epsilon) chains (human CD3ε 207 amino acids, Swissprot P07766, mature human CD3 epsilon SEQ ID NO:13; cyno CD3ε 198 amino acids, Swissprot Q95LI5, mature cyno CD3 epsilon SEQ ID NO:21), and a CD3ζ-chain (zeta) chain (human CD3ζ 164 amino acids, Swissprot P20963, cyno CD3ζ 166 amino acids, Swissprot Q09TK0). These chains associate with a molecule known as the T-cell receptor (TCR) and generate an activation signal in T lymphocytes. The TCR and CD3 molecules together comprise the TCR complex.

In a particular embodiment, at least one of said first and second binding region binds the epsilon chain of CD3, such as the epsilon chain of human CD3 (SEQ ID NO:14). In yet another particular embodiment, at least one of said first and second binding region binds an epitope within amino acids 1-27 of the N-terminal part of mature human CD3ε (epsilon) (amino acid 1-27 of mature human CD3 epsilon as set forth in SEQ ID NO:14). In such a particular embodiment, the protein may even further cross-react with other non-human primate species, such as cynomolgus monkeys (mature cyno CD3 epsilon as set forth in SEQ ID NO:21) and rhesus monkeys.

The term "mature" as used herein, refers to a protein which does not comprise any signal or leader sequence. It is well-known to the skilled person to determine a mature protein, or how to identify the sequence of the mature protein.

In one particular embodiment, the amino acids in positions corresponding to L234, L235, and D265 in a human IgG1 heavy chain of at least said first polypeptide are not L, L, and D, respectively, and wherein said first binding region binds CD3.

In one embodiment, both the first and second binding regions bind CD3.

The inventors of the present invention have evaluated Fcγ receptor binding, Fc binding of complement and further additional factors which are relevant for assessing the inertness of a protein, such as an antibody. In the case of anti-CD3 antibodies, one of such additional factors is the expression level of the T-cell activation marker CD69 which is the earliest inducible cell surface glycoprotein required during lymphoid activation.

Thus, in one embodiment, the protein of the invention, when present as a monospecific antibody binding CD3, mediates reduced Fc-mediated T-cell activation compared to a wild-type protein by at least 50%, such as at least 60%, at least 70%, at least 80%, at least 90%, at least 99% and 100%, when the T-cell activation is determined by CD69 expression. The term "when present as a monospecific antibody binding CD3" refer to such characteristics of the protein which are observed when the protein is tested in said assay as a monospecific antibody. However, it should not be understood as limiting the protein of the present invention to a monospecific antibody binding CD3, as a protein of the present invention comprising such characteristics may be used in other formats as described herein, such as in a bispecific or multispecific antibody.

In a particular embodiment, the protein, when present as a monospecific antibody binding CD3, mediates reduced Fc-mediated CD69 expression by at least 50%, such as at least 60%, at least 70%, at least 80%, at least 90%, at least 99%, and 100% when compared to a wild-type protein, when the CD69 expression is determined in a peripheral blood mononuclear cell (PBMC)-based functional assay.

In another embodiment, the protein, when present as a monospecific antibody binding CD3, mediates reduced Fc-mediated T-cell activation compared to a wild-type protein by at least 50%, such as at least 60%, at least 70%, at least 80%, at least 90%, at least 99% and 100%, when the T-cell activation is determined by CD69 expression in a peripheral blood mononuclear cells (PBMC)-based functional assay.

In a particular embodiment, the protein, when present as a monospecific antibody binding CD3, mediates reduced CD69 expression when compared to a wild-type protein by at least 50%, such as at least 60%, at least 70%, at least 80%, at least 90%, at least 99%, and 100%, when the CD69 expression is measured in a peripheral blood mononuclear cell (PBMC)-based functional assay comprising the steps of (i) incubating PBMCs with an antibody at 37° C. in a 5% (vol/vol) $CO_2$ humidified incubator for about 16-24 hrs., (ii) washing the cells, (iii) staining the cells at 4° C. with a mouse anti-human CD28-PE and mouse-anti-human CD69-APC antibody, and (iv) determining the CD69 expression on CD28 positive cells by flow cytometry.

The term "reduced" as used herein when referring to expression level of the T-cell activation marker CD69, refers to a reduction in expression level of CD69 when compared to expression level of CD69 when the T-cell is bound by a wild-type protein provided that both the binding regions of the protein binds CD3. A protein's ability to reduce expression of CD69 may be evaluated by a PBMC-based functional assay, as described in Example 3. Thus, in one embodiment, expression of CD69 is measured by a method comprising the steps of incubating PBMCs with an antibody in the range of 1-1000 ng/mL at 37° C. in a 5% (vol/vol) $CO_2$ humidified incubator for 16-24 hrs., washing the cells, staining the cells at 4° C. with a mouse anti-human CD28-PE and mouse-anti-human CD69-APC antibody, and determining CD69-expression on CD28 positive cells by flow cytometry.

The term "CD69" as used herein, refers to Cluster of Differentiation 69 which is a human transmembrane C-Type lectin protein encoded by the CD69 gene. Activation of T lymphocytes and natural killer (NK) cells, both in vivo and in vitro, induces expression of CD69. CD69 function as a signal transmitting receptor involved in cellular activation events including proliferation, functions as a signal-transmitting receptor in lymphocytes, including natural killer cells and platelets, and the induction of specific genes.

The term "peripheral blood mononuclear cell (PBMC)-based functional assay" as used herein refers to an assay used for evaluating a functional feature of the protein of the present invention, such as the ability of said protein to affect T-cell proliferation or CD69 expression, wherein the only cells present are peripheral blood mononuclear cells. A PBMC-based functional assay as described in Example 3 comprises the steps of (i) incubating PBMCs with an antibody at 37° C. in a 5% (vol/vol) $CO_2$ humidified incubator for about 16-24 hrs., (ii) washing the cells, (iii) staining the cells at 4° C. with a mouse anti-human CD28-PE and mouse-anti-human CD69-APC antibody, and (iv) determining the CD69 expression on CD28 positive cells by flow cytometry, when CD69 expression is evaluated.

The ability of anti-CD3 antibodies to induce T cell activation, or potentially agonistic antibodies that can activate T-cells after binding and cross-linking, is dependent on their FcR binding abilities. The present invention provides a protein, which does not result in CD69 expression on T-cells indicating that the protein according to the invention does not enable Fcγ Receptor binding. The term "Fcγ Receptor" as used herein, refers to a group of Fc Receptors belonging to the immunoglobulin superfamily and is the most important Fc receptors for inducing phagocytosis of opsonized (coated) microbes. This family includes several members, FcγRI (CD64), FcγRIIA (CD32a), FcγRIIB (CD32b), FcγRIIIA (CD16a), FcγRIIIB (CD16b), which differ in their antibody affinities due to their different molecular structure.

The inventors of the present invention have shown that no or low expression of CD69 is observed when a monospecific antibody comprising the amino acid substitutions L234F, L235E, and D265A binds to the T-cell (see Example 3 and 11). Thus, in a specific embodiment, the expression level of the T-cell activation marker CD69 is completely reduced.

The term "Fc-mediated T-cell activation" as used herein, refers to any activation of the T-cells which are mediated by binding of an antibody Fc region to FcR on FcR-bearing cells. The Fc region refers to a region of the protein comprising, in the direction from the N- to C-terminal, at least a hinge region, a CH2 domain and a CH3 domain. An Fc region of an IgG1 antibody can, for example, be generated by digestion of an IgG1 antibody with papain.

The term "hrs." as used herein, refers to the abbreviation of "hours".

In another embodiment, the protein, when present as a monospecific antibody binding CD3, mediates reduced Fc-mediated T-cell proliferation compared to a wild-type protein by at least 50%, such as at least 60%, at least 70%, at least 80%, at least 90%, at least 99%, and 100%, when the T-cell proliferation is measured in a PBMC-based functional assay.

In one embodiment, the protein, when present as a monospecific antibody binding CD3, mediates reduced Fc-mediated T-cell proliferation by at least 50%, such as at least 60%, at least 70%, at least 80%, at least 90%, at least 99%, and 100%, when the T-cell proliferation is measured in a PBMC-based functional assay comprising the steps of (i) incubating PBMCs with an antibody at 37° C. in a 5% (vol/vol) $CO_2$ humidified incubator for three days, (ii) adding an agent capable of incorporation into the cell DNA, (iii) incubating for 3 to 8 hrs., (iv) pelleting cells, (v) coating cells to an ELISA plate, (vi) incubating with an anti-DNA incorporated agent for 60 to 120 min at room temperature.

In a particular embodiment, the protein, when present as a monospecific antibody binding CD3, mediates reduced Fc-mediated T-cell proliferation by at least 50%, such as at least 60%, at least 70%, at least 80%, at least 90%, at least 99%, and 100%, when the T-cell proliferation is measured in a PBMC-based functional assay comprising the steps of (i) incubating PBMCs with an antibody at 37° C. in a 5% (vol/vol) $CO_2$ humidified incubator for three days, (ii) adding BrdU, (iii) incubating for five hrs., (iv) pelleting cells, (v) coating cells to an ELISA plate, (vi) incubating with anti-BrdU-peroxidase for 90 min at room temperature, (vii) developing the plate for about 30 min with 1 mg/mL 2,2'-azino-bis (3-ethylbenzothiazoline-6-sulfonic acid), (viii) adding 100 μL 2% oxalic acid to stop the reaction, and (xi) measuring absorbance at 405 nm.

The term "reduced" as used herein when referring to T-cell proliferation, refers to a reduction in the ability of the protein according to the invention to induce proliferation of T-cells when compared to the induction of proliferation of T-cells bound by a wild-type protein provided that both the binding regions of the protein binds CD3. The reduction in ability of a protein to induce T-cell proliferation may be evaluated by a PBMC-based functional assay, as described in Example 4. Thus, in one embodiment, T-cell proliferation is measured by a method comprising the steps of incubating PBMCs with antibody in the range of 1-1000 ng/mL at 37° C. in a 5% (vol/vol) $CO_2$ humidified incubator for three days, adding a chemical compound, such as BrdU, which is incorporated into the DNA of proliferating cells, incubating for five hrs., pelleting cells, drying cells, optionally storing the cells at 4° C., coating cells to ELISA plates, incubating with anti-BrdU-peroxidase for 90 min at room temperature, developing for about 30 min with 1 mg/mL 2,2'-azino-bis (3-ethylbenzothiazoline-6-sulfonic acid), adding 100 μL 2% oxalic acid to stop the reaction, and measuring absorbance at 405 nm in a suitable microplate reader.

The term "BrdU" as used herein, refers to 5-bromo-2'-deoxyuridine, which is a homologue to thymidine. When BrdU is added to cell culture for a limited period of time (e.g. 4 hours) it will be incorporated into the DNA of proliferating cells. After fixing the cells, detection of incorporated BrdU may be performed in an ELISA using anti-BrdU-peroxidase. BrdU incorporation is therefore a measure for proliferation.

In a specific embodiment, the T-cell proliferation is completely reduced. Thus, no proliferation of T-cells may be observed, or the level of proliferation may be equal to the proliferation of T-cells which has not been treated with a protein according to the invention or has been treated with a wild-type protein. The invention provides an antibody comprising the amino acid substitutions L234F, L235E, and D265A, which results in absolutely no proliferation of T-cells, indicating that the protein according to the invention does not enable Fcγ Receptor binding, as described in Example 4 and 12.

Furthermore, an antibody according to the invention, i.e. an antibody comprising the amino acid substitutions L234F, L235E, and D265A, has been shown to retain its ability to kill tumor cells. As can be seen in Example 5, the amino acid substitutions according to the present invention have little effect on efficacy of the antibodies. Testing a protein according to the present invention for cytotoxicity efficacy, may be performed in a cytotoxicity assay comprising the steps of (i) putting tumor cells in a cell plate, (ii) adding samples, such as antibody dilutions, in a dose response series, (iii) incubating the cell plate for about 3 hrs., (iv) adding isolated PBCMs from whole blood, (v) incubating plates for three days, (vi) washing plates, (vii) incubating plates with culture medium containing 10% Alamar Blue for four hrs., and (viii) measuring cell viability.

A monospecific antibody fulfilling the assay conditions herein described may form the basis of a bispecific antibody, i.e. in a bispecific antibody wherein one of the binding regions binds CD3 may originate from any monospecific CD3 antibody tested for the ability of mediating reduced CD69 expression and/or Fc-mediated T-cell proliferation in the functional assays, and fulfilling the requirements, described herein.

The inventors of the present invention have shown, that a bispecific antibody comprising the amino acid substitutions L234F, L235E, and D265A, and which first binding region binds CD3 and which second binding region binds a cancer-specific antigen (HER2), that besides the ability of inducing dose-dependent killing of AU365 cells with at least comparable efficacy compared to the wild-type bispecific antibody without the non-activating mutation (as described in Example 5 and 13), the bispecific antibody according to the invention also showed cytokine release caused by unspecific killing is inhibited, as described in Example 6. It was shown, that incubation of target and effector cells in the presence of a bispecific antibody according to the invention, did not lead to any cytokine production caused by unspecific killing (as described in Example 5), whereas the wild-type antibody showed a higher cytokine production which is believed to be due to the unspecific activation of T-cells via cross-linking with other effector cells. Thus, in one embodiment, in the first and second polypeptides the amino acids in positions corresponding to position L234, L235, and D265, in a human IgG1 heavy chain are not L, L, and D, said first binding region binds CD3, and said second binding region binds a tumor-specific target.

The term "cytokine release" as used herein is intended to refer to the release of cytokines, such as interleukins and interferons, upon activation of e.g. T-cells. Cytokines are involved in a broad array of biological activities including innate immunity, adaptive immunity, and inflammation. Cytokines may activate the cell types from which they have been released and thus, stimulating to produce more cytokines.

The ability of a protein according to the invention to induce cytokine release may be determined in an assay comprising the steps of (i) incubating supernatant from a cytotoxicity assay as described above for about 1 to 2 hrs. at room temperature in a plate, (ii) incubating further 1 to 2 hrs. with added solution comprising antibodies against the cytokines to be tested, such solution may be a Detection Antibody Solution to the plate, (iii) washing the plate, (iv) adding a conductor to enhance the signal to be read, such as a Read Buffer T, and (v) measuring chemiluminescence.

As described above, complement activation is an effector function which some antibodies are able to induce. The first step in the complement cascade is Fc binding of C1q and therefore serves as an indicator for CDC capacity of antibodies. As the present invention relates to inertness of antibodies, complement activation is not wanted and therefore, deposition of C1q to antibodies was determined in by ELISA as described in Example 7. As determined in said Example, an antibody according to the present invention abrogates C1q binding which suggests that the antibodies of the present invention are not capable of inducing CDC.

The term "C1q binding" as used herein is intended to refer to the binding of C1q to an antibody, when said antibody is bound to its antigen. The term "bound to its antigen" as used herein refers both to binding of an antibody to its antigen in vivo and in vitro.

Thus, the ability of a protein according to the present invention of C1q binding may be determined by ELISA comprising the steps of adding an anti-human C1q and adding an anti-rabbit IgG-Fc-HRP antibody.

Specifically, the ability of a protein according to the present invention of C1q binding may be determined by ELISA comprising the steps of (i) coating an ELISA plate with a dilution series of an protein, (ii) blocking the plate, (iii) adding 3% serum, (iv) incubating the plate for 1 hr at 37° C., (v) washing the plate, (vi) adding an anti-human C1q, (vi) incubating the plate for 1 hr at room temperature, (vii) washing the plate, (viii) adding an anti-rabbit IgG-Fc-HRP antibody, (ix) incubating the plate for 1 hr at room temperature, (x) washing the plate, (xi) developing the plate, and (xii) measuring OD$_{405}$ nm.

Further analysis of a protein according to the present invention may include determining FcγRI binding as described in Example 8. As described above, Fcγ Receptors is a group of Fc Receptors, which comprise of five different variants of Fcγ Receptors. FcγRI is a high affinity Fc receptor, which means that the binding between an FcγRI and an Fc region of a protein is strong. If binding to the FcγRI can be inhibited or even abrogated, it is a good indicator of the inertness of a protein. Thus, evaluating the Fc binding of a protein to FcγRI, is another way of determining the inertness of said protein. In one embodiment the protein according to the present invention has completely abrogated Fc binding to FcγRI. FcγRI binding ability of a protein according to the present invention may be evaluated by flow cytometry comprising the steps of (i) incubating FcγRI positive cells for approx. 30 min at 4° C. with an antibody to be tested; (ii) washing the cells, (iii) staining the cells for approx. 30 min at 4° C. with an anti-human IgG-PE F(ab')$_2$ antibody, (iv) washing the cells, and (v) measuring the mean fluorescence of the cells.

The term "approx." as used herein refers to an abbreviation of the term "approximately".

As described herein an antibody according to the invention, wherein said first and second polypeptides of said antibody comprise the amino acid substitutions L234F, L235E, and D265A, and the first binding region binds CD3, has proven to completely reduce expression of CD69 and thereby abrogating T-cell activation (Example 3), completely reduce T-cell proliferation (Example 4), completely reduce unspecific killing (Example 5), completely reduce cytokine release when present as a monospecific antibody binding CD3, i.e. the two binding regions of the antibody binds the same target (Example 6), abrogate C1q binding (Example 7) as well as completely reduce FcγRI binding (Example 8) when compared to a wild-type antibody. Therefore, it is believed that the amino acid positions corresponding to positions L234, L235 and D265 in a human IgG1 heavy chain are crucial positions in an antibody in order to provide an antibody that has the before-mentioned features.

Thus, in one embodiment, in at least one of said first and second polypeptides the amino acids corresponding to positions L234 and L235 in a human IgG1 heavy chain is selected from the group consisting of; A, C, D, E, F, G, H, I, K, M, N, P, Q, R, S, T, Y, V, and W, and the amino acid corresponding to position D265 is selected from the group consisting of; A, C, E, F, G, H, I, K, L, M, N, P, Q, R, S, T, Y, V, and W.

In one embodiment, in at least one of said first and second polypeptides the amino acids in the positions corresponding to positions L234, L235 and D265 in a human IgG1 heavy chain are hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second polypeptides the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

The term "polar" as used herein in relation to amino acid residues, refers to any amino acid residue selected from the group consisting of; C, D, E, H, K, N, Q, R, S, and T. Thus, in one embodiment, in at least one of said first and second polypeptides the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in at least one of said first and second polypeptides the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In one embodiment, in both said first and second polypeptides the amino acids in the positions corresponding to L234, L235, and D265 in a human IgG1 heavy chain are hydrophobic or polar amino acids.

In one embodiment, in both said first and second polypeptides the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

In one embodiment, in both said first and second polypeptides the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in both said first and second polypeptides the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In another embodiment, in at least one of said first and second polypeptides the amino acids in the positions corresponding to positions L234, L235 and D265 in a human IgG1 heavy chain are aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in at least one of said first and second polypeptides the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

The term "aromatic" as used herein in relation to amino acid residues, refers to any amino acid residue selected from the group consisting of: F, T, and W. Thus, in one embodiment, in at least one of said first and second polypeptides the amino acids in the positions corresponding to positions L234, L235 and D265 in a human IgG1 heavy chain are each selected from the group consisting of; F, T, and W.

The term "acidic" as used herein in relation to amino acid residues, refers to any amino acid residue chosen from the group consisting of: D and E. Thus, in one embodiment, in at least one of said first and second polypeptides the amino acids in the positions corresponding to positions L234, L235, and D265 in a human IgG1 heavy chain are each selected from the group consisting of; D and E.

In a particular embodiment, in at least one of said first and second polypeptides the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in both said first and second polypeptides the amino acids in the positions corresponding to L234, L235, and D265 in a human IgG1 heavy chain are aliphatic uncharged, aromatic or acidic amino acids.

In one embodiment, in both said first and second polypeptides the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

In one embodiment, in both said first and second polypeptides the amino acids in the positions corresponding to positions L234, L235, and D265 in a human IgG1 heavy chain are each selected from the group consisting of; D and E.

In a particular embodiment, in both said first and second polypeptides the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In a further embodiment, in at least one of said first and second polypeptides, the amino acids corresponding to positions L234, L235 and D265 in a human IgG1 heavy chain are F, E, and A; or A, A, and A, respectively.

In one embodiment, in both said first and second polypeptides the amino acids in the positions corresponding to position L234, L235, and D265 in a human IgG1 heavy chain are F, E, and A; or A, A, and A, respectively.

In a particular embodiment, in at least one of said first and second polypeptides the amino acids corresponding to positions L234, L235 and D265 in a human IgG1 heavy chain are F, E, and A, respectively.

In one embodiment, in both said first and second polypeptides the amino acids in the positions corresponding to position L234, L235, and D265 in a human IgG1 heavy chain are F, E, and A, respectively.

In one embodiment, in at least one of said first and second polypeptides the amino acids corresponding to positions L234, L235, and D265 in a human IgG1 heavy chain are A, A, and A, respectively.

In one embodiment, in both said first and second polypeptides the amino acids in the positions corresponding to positions L234, L235, and D265 in a human IgG1 heavy chain are A, A, and A, respectively.

The term "isotype" as used herein refers to the immunoglobulin class (for instance IgG1, IgG2, IgG3, and IgG4) or any allotypes thereof such as IgG1m(za) and IgG1m(f)) that is encoded by heavy chain constant region genes. Further, each heavy chain isotype can be combined with either a kappa (K) or lambda (2) light chain or any allotypes thereof.

Thus, in one embodiment, the isotype of the immunoglobulin heavy chains is selected from the group consisting of IgG1, IgG2, IgG3, and IgG4. The immunoglobulin heavy chain may be any allotype within each of the immunoglobulin classes, such as IgG1m(f) (SEQ ID NO:13). Thus, in one particular embodiment, the isotype of the immunoglobulin heavy chains are an IgG1, or any allotype thereof, such as IgG1m(f).

In another embodiment, at least said first binding region is selected from the group consisting of;
a. a binding region comprising heavy chain variable region sequence as set out in SEQ ID NO:6 and light chain variable region sequence as set out in SEQ ID NO:12;
b. a binding region comprising heavy chain variable region sequence as set out in SEQ ID NO:8 and light chain variable region sequence as set out in SEQ ID NO:12; and
c. a binding region comprising heavy chain variable region sequence as set out in SEQ ID NO:9 and light chain variable region sequence as set out in SEQ ID NO:10.

In one embodiment, both said first and second polypeptides are according to any of the embodiments described above.

In one embodiment, the second binding region binds a different target than said first binding region. Thus, the protein is a bispecific protein, such as a bispecific antibody. The term "bispecific protein" or "bispecific antibody" refers to a protein or antibody having specificities for two different, typically non-overlapping, epitopes, and comprises two different binding regions. Such epitopes may be on the same or different targets. If the epitopes are on different targets, such targets may be on the same cell or different cells or cell types.

The term "target" as used herein refers to a molecule to which the binding region of the protein according to the invention binds. When used in the context of the binding of an antibody includes any antigen towards which the raised antibody is directed.

Thus, in one embodiment, the protein is a bispecific antibody.

There is a range of applications, such as receptor inhibition or T-cell recruitment by bispecific antibodies, in which the Fc binding of the Fc region of therapeutic antibodies to effector cells or complement is not required or even is undesired as it may contribute to unwanted cytotoxicity. Thus, a bispecific antibody which binds with one binding region to human CD3 will be able to recruit cytotoxic T-cells. CD3 bispecific antibodies with an activating IgG Fc region can induce unwanted agonism in the absence of tumor cells through crosslinking by FcγR-expressing cells, inappropriate activation of FcγR-expressing cells and subsequent cytokine storm and associated toxic effects, or platelet aggregation. Thus, CD3 bispecific antibodies with a non-activating Fc region are advantageous to prevent potential unwanted cell activation.

A bispecific antibody according to the present invention is not limited to any particular bispecific format or method of producing it.

Examples of bispecific antibody molecules which may be used in the present invention comprise (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')$_2$ fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab arm exchange (such as described in WO 11/131746) as those described in the present invention.

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule fused to heavy-chain constant-domains, Fc-regions or parts thereof.

Examples of IgG-like molecules with complementary CH3 domains molecules include but are not limited to the Triomab/Quadroma (Trion Pharma/Fresenius Biotech; Roche, WO2011069104), the Knobs-into-Holes (Genentech, WO9850431), CrossMAbs (Roche, WO2011117329) and the electrostatically-matched (Amgen, EP1870459 and WO2009089004; Chugai, US201000155133; Oncomed, WO2010129304), the LUZ-Y (Genentech), DIG-body and PIG-body (Pharmabcine), the Strand Exchange Engineered Domain body (SEEDbody)(EMD Serono, WO2007110205), the Biclonics (Merus), FcΔAdp (Regeneron, WO201015792), bispecific IgG1 and IgG2 (Pfizer/Rinat, WO11143545), Azymetric scaffold (Zymeworks/Merck, WO2012058768), mAb-Fv (Xencor, WO2011028952), bivalent bispecific antibodies (Roche) and the DuoBody (Genmab A/S, WO2011131746).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), mAb$^2$ (F-Star, WO2008003116), Zybodies (Zyngenia), approaches with common light chain (Crucell/Merus, U.S. Pat. No. 7,262,028), κλBodies (NovImmune) and CovX-body (CovX/Pfizer).

Examples of IgG fusion molecules include but are not limited to Dual Variable Domain (DVD)-Ig (Abbott, U.S. Pat. No. 7,612,181), Dual domain double head antibodies (Unilever; Sanofi Aventis, WO20100226923), IgG-like Bispecific (ImClone/Eli Lilly), Ts2Ab (MedImmune/AZ) and BsAb (Zymogenetics), HERCULES (Biogen Idec, US007951918), scFv fusion (Novartis), scFv fusion (Changzhou Adam Biotech Inc, CN 102250246) and TvAb (Roche, WO2012025525, WO2012025530).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART) (MacroGenics, WO2008157379, WO2010/080538) and Dual (ScFv)$_2$-Fab (National Research Center for Antibody Medicine—China).

Examples of Fab fusion bispecific antibodies include but are not limited to F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

It is further contemplated that any monospecific antibody fulfilling the assay conditions herein described may form the basis of a bispecific antibody, i.e. in a bispecific antibody wherein one of the binding regions binds CD3 may originate from any monospecific CD3 antibody tested in the functional assays and fulfilling the requirements stated herein. Such bispecific antibody may be provided by the methods described in WO 2011/131746, which is hereby incorporated by reference.

Thus, in a particular embodiment, in said first polypeptide at least one of the amino acids in the positions corresponding to a position selected from the group consisting of T366, L368, K370, D399, F405, Y407, and K409 in a human IgG1 heavy chain has been substituted, and in said second polypeptide at least one of the amino acids in the positions corresponding to a position selected from the group consisting of; T366, L368, K370, D399, F405, Y407, and K409 in a human IgG1 heavy chain has been substituted, and wherein said substitutions of said first and said second polypeptides are not in the same positions. In this context the term "substituted", refers to the amino acid in a specific amino acid position which has been substituted with another naturally or non-naturally occurring amino acid. Thus, a "substituted" amino acid in a position corresponding to the position in a human IgG1 heavy chain means the amino acid at the particular positions is different from the naturally occurring amino acid in an IgG1 heavy chain.

In one embodiment, in said first polypeptide the amino acid in the position corresponding to K409 in a human IgG1 heavy chain is not K, L or M, and the amino acid in the position corresponding to F405 in a human IgG1 heavy chain is F, and in said second polypeptide at least one of the amino acids in the positions corresponding to a position selected from the group consisting of; T366, L368, K370, D399, F405, and Y407 in a human IgG1 heavy chain has been substituted.

In one embodiment, in said first polypeptide the amino acid in the position corresponding to K409 in a human IgG1 heavy chain is not K, L or M, and the amino acid in the position corresponding to F405 in a human IgG1 heavy chain is F, and in said second polypeptide the amino acid in the position corresponding to F405 in a human IgG1 heavy chain is not F and the amino acid in the position corresponding to K409 in a human IgG1 heavy chain is K.

In one embodiment, in said first polypeptide, the amino acid in the position corresponding to F405 in a human IgG1 heavy chain is not F, R, and G, and the amino acid in the position corresponding to K409 in a human IgG1 heavy chain is K, and in said second polypeptide the amino acids in the positions corresponding to a position selected form the group consisting of; T366, L368, K370, D399, Y407, and K409 in a human IgG1 heavy chain has been substituted.

In one embodiment, in said first polypeptide, the amino acid in the position corresponding to K409 in a human IgG1 heavy chain is not K, L or M, and the amino acid in the position corresponding to F405 in a human IgG1 heavy chain is F, and the amino acid in position corresponding to F405 in a human IgG1 heavy chain is not F, and the amino acid in the position corresponding to K409 in a human IgG1 heavy chain is K.

In a further embodiment, the amino acid in the position corresponding to F405 in a human IgG1 heavy chain is L in said first polypeptide, and the amino acid in the position corresponding to K409 in a human IgG1 heavy chain is R in said second polypeptide, or vice versa.

In one embodiment, the targets are present on different cells. In a particular embodiment, the first binding region binds CD3 present on a T-cell and the second binding region binds a tumor-specific target present on a cancer cell. Thereby, the bispecific protein, such as a bispecific antibody, binds two different cell types. When both cell types are engaged, activation of the T-cells, particularly the cytotoxic T-cells (CD8+ T-cells), will be triggered by the specific interaction between the T-cells and the cancer/tumor cells. Thus, the protein according to the present invention provides an attractive way of activating T-cells and killing cancer cells.

Thus, in a particular embodiment, the protein is a bispecific antibody, both said first and second polypeptide the amino acids in the positions corresponding to L234, L235 and D265 in a human IgG1 heavy chain are F, E, and A, respectively, said first binding region binds CD3, and said second binding region binds a cancer-specific target.

In one embodiment, the protein according to any aspects or embodiments herein described is an antibody. In one embodiment, the protein is a bispecific antibody. In one embodiment, the antibody is a full-length antibody or a human antibody. In one embodiment, the antibody is a human IgG1 antibody.

Furthermore, it is contemplated that a wild-type protein according to any aspect or embodiment herein described may also be a parent protein. Thus, the present invention also relates to a variant of such a parent protein. Therefore, it is contemplated that any protein according to the invention may also be regarded as a variant of a parent protein obtained by modifying the parent protein.

The protein according to the invention may be prepared by a method comprising introducing into the first and/or second polypeptides of a wild-type protein, amino acid substitutions in the positions corresponding to L234, L235 and D265 in a human IgG1 heavy chain.

A variant according to the invention may be prepared by a method comprising introducing into the first and/or second polypeptides of a parent protein, amino acid substitutions in the positions corresponding to L234, L235, and D265 in a human IgG1 heavy chain.

Methods of preparing an antibody are well-known to the skilled person. However, a non-limiting example of preparing an antibody according to the invention may be by a method comprising immunizing a non-human animal, e.g. a mouse, obtaining the antibodies from the non-human animal, introducing amino acid mutations in the Fc region according to the invention by recombinant techniques, expressing the nucleic acids obtained by the recombinant techniques in a suitable expression system, and purifying the expressed antibodies.

As described herein, the present invention relates in one embodiment to an antibody wherein in least one of the two heavy chains of an immunoglobulin the amino acids in the positions corresponding to positions L234, L235, and D265 in a human IGG1 heavy chain, are not L, L, and D, respectively. Thus, the protein of the present invention may be prepared by introducing mutations into said positions of an antibody. An antibody into which said mutations are introduced may be regarded as a "parent antibody". The "parent" antibodies, which may be wild-type antibodies, to be used as starting material of the present invention before modification may e.g. be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624 628 (1991) and Marks et al., J. Mol. Biol. 222, 581 597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rabbits, rats, dogs, primates, etc.

The parent antibodies may be e.g. chimeric or humanized antibodies. In another embodiment, the antibody is a human antibody. Human monoclonal antibodies may be generated using transgenic or transchromosomal mice, e.g. HuMAb mice, carrying parts of the human immune system rather than the mouse system. The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., Nature 368, 856 859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49 101 (1994), Lonberg, N. and Huszar, D., Intern. Rev. Immunol. Vol. 13 65 93 (1995) and Harding, F. and Lonberg, N. Ann. N.Y. Acad. Sci 764 536 546 (1995)). The preparation of HuMAb mice is described in detail in Taylor, L. et al., Nucleic Acids Research 20, 6287 6295 (1992), Chen, J. et al., International Immunology 5, 647 656 (1993), Tuaillon et al., J. Immunol. 152, 2912 2920 (1994), Taylor, L. et al., International Immunology 6, 579 591 (1994), Fishwild, D. et al., Nature Biotechnology 14, 845 851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat.

No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187. Splenocytes from these transgenic mice may be used to generate hybridomas that secrete human monoclonal antibodies according to well-known techniques.

Further, human antibodies of the present invention or antibodies of the present invention from other species may be identified through display-type technologies, including, without limitation, phage display, retroviral display, ribosomal display, mammalian display, yeast display and other techniques known in the art, and the resulting molecules may be subjected to additional maturation, such as affinity maturation, as such techniques are well known in the art.

The parent antibody is not limited to antibodies which have a natural, e.g. a human Fc region but it may also be an antibody having other mutations than those of the present invention, such as e.g. mutations that affect glycosylation or enables the antibody to be a bispecific antibody. By the term "natural antibody" is meant any antibody which does not comprise any genetically introduced mutations. An antibody which comprises naturally occurred modifications, e.g. different allotypes, is thus to be understood as a "natural antibody" in the sense of the present invention, and can thereby be understood as a parent antibody. Such antibodies may serve as a template for the one or more mutations according to the present invention, and thereby providing the variant antibodies of the invention. An example of a parent antibody comprising other mutations than those of the present invention is the bispecific antibody as described in WO2011/131746 (Genmab) or other mutations related to any bispecific antibody described herein.

The parent antibody may bind any target.

Monoclonal antibodies for use in the present invention, may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody is a human antibody. Human monoclonal antibodies directed against any antigen may be generated using transgenic or transchromosomal mice carrying parts of the human immune system rather than the mouse system. Such transgenic and transchromosomic mice include mice referred to herein as HuMAb® mice and KM mice, respectively, and are collectively referred to herein as "transgenic mice".

The HuMAb® mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb® mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5[J/K](Balb) as described in WO/2009/097006.

Splenocytes from these transgenic mice may be used to generate hybridomas that secrete human monoclonal antibodies according to well-known techniques.

Further, any antigen-binding regions may be obtained from human antibodies or antibodies from other species identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382

(1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

Systems for expression of the protein and variant according to the invention are well-known in the art for the skilled person and include but are not limited to those described herein.

In one aspect, the invention provides a composition comprising the protein or variant according to any aspects and embodiments herein described.

Nucleic Acids and Expression Constructs

In a further aspect, the present invention relates to a nucleic acid encoding a first or second polypeptide according to the present invention, wherein the amino acids in the position corresponding to L234, L235 and D265 in a human IgG1 heavy chain, are not L, L, and D. It is further contemplated that the nucleic acid encoding a first or second polypeptide according to the invention comprises the amino acid substitutions in the specific amino acid positions herein described. Thus, in one embodiment, the nucleic acid encodes a first or second polypeptide having the sequence according to SEQ ID NO:20. In the amino acid sequence as set out in SEQ ID NO:20 the specific three amino acid substitutions L234F, L235E and D265A have been indicated by bold and underlined letters.

In another aspect, the invention relates to nucleic acids encoding a sequence of a human, humanized or chimeric CD3 antibody for use in the invention, to expression vectors encoding the sequences of such an antibody, to host cells comprising such expression vectors, to hybridomas which produce such antibodies, and to methods of producing such an antibody by culturing such host cells or hybridomas under appropriate conditions whereby the antibody is produced and, optionally, retrieved. Humanized CD3 antibodies may also be denoted as "huCD3".

In one embodiment, the invention provides an expression vector comprising a nucleotide sequence encoding the amino acid sequence according to SEQ ID NOs:21 or 28.

In one embodiment, the invention provides an expression vector comprising a nucleotide sequence encoding one or more amino acid sequences selected from the group consisting of SEQ ID NOs: 6, 7, 8, 9, 10, 11, and 12, or any combination thereof. In another embodiment, the expression vector comprises a nucleotide sequence encoding any one or more of the VH CDR3 amino acid sequences selected from SEQ ID NOs: 3 and 15. In another embodiment, the expression vector comprises a nucleotide sequence encoding a VH amino acid sequence selected from SEQ ID NOs: 6, 7, 8, and 9. In another embodiment, the expression vector comprises a nucleotide sequence encoding a VL amino acid sequence selected from SEQ ID NOs: 10, 11, and 12. In another embodiment, the expression vector comprises a nucleotide sequence encoding the constant region of a human antibody light chain, of a human antibody heavy chain, or both. In another embodiment, the expression vector comprising a nucleotide sequence encoding the constant region of a human antibody heavy chain of SEQ ID NOs:13.

In a particular embodiment, the expression vector comprises a nucleotide sequence encoding a variant of one or more of the above amino acid sequences, said variant having at most 25 amino acid modifications, such as at most 20, such as at most 15, 14, 13, 12, or 11 amino acid modifications, such as 10, 9, 8, 7, 6, 5, 4, 3, 2, or 1 amino acid modifications, such as deletions or insertions, preferably substitutions, such as conservative substitutions, or at least 80% identity to any of said sequences, such as at least 85% identity or 90% identity or 95% identity, such as 96% identity or 97% identity or 98% identity or 99% identity to any of the afore-mentioned amino acid sequences.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a humanized CD3 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $CaPO_4^-$-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the humanized CD3 antibody, the first and the second polypeptides in a bacterial cell. Examples of such vectors include expression vectors such as BlueScript (Stratagene), pIN vectors (Van Heeke & Schuster, J Biol Chem 264, 5503-5509 (1989)), pET vectors (Novagen, Madison Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, CD3 antibody-encoding nucleic acids and the first and the second polypeptides nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E.

*coli*, an antibiotic resistance gene as selectable marker, and/or a convenient cloning site (e.g., a polylinker). Nucleic acids may also comprise an inducible promoter as opposed to a constitutive such as CMV IE (the skilled artisan will recognize that such terms are actually descriptors of a degree of gene expression under certain conditions).

In one embodiment, the CD3 antibody-encoding expression vector and the first and the second polypeptides expression vector is positioned in and/or delivered to the host cell or host animal via a viral vector.

Such expression vectors may be used for recombinant production of CD3 antibodies and the first and the second polypeptides.

In one aspect, the CD3 antibodies and the first and the second polypeptides of any aspect or embodiment described herein are provided by use of recombinant eukaryotic or prokaryotic host cell which produces the antibody. Accordingly, the invention provides a recombinant eukaryotic or prokaryotic host cell, such as a transfectoma, which produces a CD3 antibody, the first and the second polypeptides, or immunoglobulin as defined herein. Examples of host cells include yeast, bacterial and mammalian cells, such as CHO or HEK-293 cells. For example, in one embodiment, the host cell comprises a nucleic acid stably integrated into the cellular genome that comprises a sequence coding for expression of a CD3 antibody described herein. In one embodiment, the host cell comprises a nucleic acid stably integrated into the cellular genome that comprise a sequence coding for expression of a first or a second polypeptide described herein. In another embodiment, the host cell comprises a non-integrated nucleic acid, such as a plasmid, cosmid, phagemid, or linear expression element, which comprises a sequence coding for expression of a CD3 antibody, a first or a second polypeptide described herein.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6, NS0 cells, HEK-293 cells, plant cells, or fungi, including yeast cells.

In a further aspect, the invention relates to a method for producing an antibody of the invention, said method comprising the steps of a) culturing a hybridoma or a host cell of the invention as described herein above, and b) retrieving and/or purifying the antibody of the invention from the culture media.

In a further aspect, the nucleotide sequence encoding a sequence of an antibody further encodes a second moiety, such as a therapeutic polypeptide. Exemplary therapeutic polypeptides are described elsewhere herein. In one embodiment, the invention relates to a method for producing an antibody fusion protein, said method comprising the steps of a) culturing a host cell comprising an expression vector comprising such a nucleotide sequence, and b) retrieving and/or purifying the antibody fusion protein from the culture media.

Pharmaceutical Compositions

In one aspect, the invention provides a pharmaceutical composition comprising a protein, such as an antibody, as defined in any of the aspects and embodiments herein described, and a pharmaceutically acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the protein, variant or antibody of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a protein, variant or antibody of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intra-arterial, intrathecal, intracapsular, intraorbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption-delaying agents, and the like that are physiologically compatible with a protein, variant or antibody of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. When referring to the "active compound" it is contemplated to also refer to the protein, the antibody, the variant of a parent protein or patent antibody according to the present invention.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The protein, variant and antibody of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-orthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the proteins, antibodies, or variants of a parent protein or parent antibody of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Therapeutic Applications

In another aspect, the present invention relates to a protein, e.g. antibody, or pharmaceutical composition of the invention as defined in any aspect or embodiment herein described, for use as a medicament.

In another aspect, the present invention relates to a protein, variant, antibody, or pharmaceutical composition of the invention as defined in any aspect or embodiment herein described, for use in the treatment of a disease.

The protein, variant, antibody, or pharmaceutical composition of the invention can be used as in a treatment wherein the effector mechanisms of cytotoxic T-cells are desired. For example, the protein, variant, or antibody may be administered to cells in culture, e.g., in vitro or ex vivo, or to human subjects, e.g. in vivo, to treat or prevent disorders such as cancer, inflammatory or autoimmune disorders. As used herein, the term "subject" is typically a human which respond to the protein, variant, antibody, or pharmaceutical composition. Subjects may for instance include human patients having disorders that may be corrected or ameliorated by modulating a target function or by leading to killing of the cell, directly or indirectly.

In another aspect, the present invention provides methods for treating or preventing a disorder, such as cancer, wherein recruitment of T-cells would contribute to the treatment or prevention, which method comprises administration of a therapeutically effective amount of a protein, variant, antibody, or pharmaceutical composition of the present invention to a subject in need thereof. The method typically involves administering to a subject a protein, variant, or antibody in an amount effective to treat or prevent the disorder.

In one particular aspect, the present invention relates to a method of treatment of cancer comprising administering the protein, variant, antibody, or pharmaceutical composition of the invention as defined in any aspect and embodiments herein described.

In another aspect, the present invention relates to the use or the method of the invention as defined in any aspect and embodiments herein described wherein the disease is cancer, inflammatory or autoimmune diseases.

Cells overexpressing tumor-specific targets are particularly good targets for the protein, variant or antibody of the invention, since recruitment of T-cells by one of the two binding regions of the protein, variant, or antibody will trigger a cytotoxic activity of the T-cells. This mechanism is normally difficult to obtain, as the triggering of a cytotoxic activity does not work properly in elimination of cancer cells.

The efficient dosages and dosage regimens for the protein, variant, or antibody depend on the disease or condition to be treated and may be determined by the persons skilled in the art.

A physician having ordinary skill in the art may readily determine and prescribe the effective amount of the pharmaceutical composition required. For example, the physician could start doses of the protein, variant, or antibody employed in the pharmaceutical composition at levels lower than that required in order to achieve the desired therapeutic effect and gradually increase the dosage until the desired effect is achieved. In general, a suitable dose of a composition of the present invention will be that amount of the protein, variant, or antibody which is the lowest dose effective to produce a therapeutic effect according to a particular dosage regimen. Such an effective dose will generally depend upon the factors described above.

For example, an "effective amount" for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the protein, variant, or antibody to inhibit cell growth or to induce cytotoxicity by in vitro assays known to the skilled practitioner. A therapeutically effective amount of a therapeutic compound, i.e. a therapeutic protein, variant, antibody, or pharmaceutical composition according to the invention, may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An exemplary, non-limiting range for a therapeutically effective amount of a protein, variant or antibody of the invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

Administration may e.g. be intravenous, intramuscular, intraperitoneal, or subcutaneous, and for instance administered proximal to the site of the target.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In one embodiment, the efficacy of the treatment is monitored during the therapy, e.g. at predefined points in time.

If desired, an effective daily dose of a pharmaceutical composition may be administered as two, three, four, five, six or more sub-doses administered separately at appropriate intervals throughout the day, optionally, in unit dosage forms. In another embodiment, the protein, variant, antibody, or pharmaceutical composition is administered by slow continuous infusion over a long period, such as more than 24 hours, in order to minimize any unwanted side effects.

While it is possible for a protein, variant, or antibody of the present invention to be administered alone, it is preferable to administer the protein, variant, or antibody as a pharmaceutical composition as described above.

An effective dose of a protein, variant, or antibody of the invention may also be administered using a weekly, biweekly or triweekly dosing period. The dosing period may be restricted to, e.g., 8 weeks, 12 weeks or until clinical progression has been established.

In one embodiment, the protein, antibody or variant may be administered by infusion in a weekly dosage of calculated by mg/m$^2$. Such dosages can, for example, be based on the mg/kg dosages provided above according to the following: dose (mg/kg)×70:1.8. Such administration may be repeated, e.g., 1 to 8 times, such as 3 to 5 times. The administration may be performed by continuous infusion over a period of from 2 to 24 hours, such as of from 2 to 12 hours. In one embodiment, the protein, antibody or variant may be administered by slow continuous infusion over a long period, such as more than 24 hours, in order to reduce toxic side effects.

In one embodiment, the protein, antibody or variant may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of protein, antibody or variant of the present invention in the blood upon administration by for instance taking out a biological sample and using anti-idiotypic antibodies which target the binding region of the proteins, antibodies or variants of the present invention.

In one embodiment, the protein, antibody or variant may be administered by maintenance therapy, such as, e.g., once a week for a period of 6 months or more.

A protein, antibody or variant may also be administered prophylactically in order to reduce the risk of developing cancer, delay the onset of the occurrence of an event in cancer progression, and/or reduce the risk of recurrence when a cancer is in remission.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

A protein, variant, antibody, or antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Diagnostic Applications

The non-activating protein of the invention may also be used for diagnostic purposes, using a composition comprising a protein as described herein. Accordingly, the invention provides diagnostic methods and compositions using the proteins described herein. Such methods and compositions can be used for purely diagnostic purposes, such as detecting or identifying a disease, as well as for monitoring of the progress of therapeutic treatments, monitoring disease progression, assessing status after treatment, monitoring for recurrence of disease, evaluating risk of developing a disease, and the like.

In one aspect, the protein of the present invention are used ex vivo, such as in diagnosing a disease in which cells expressing a specific target of interest and to which the protein binds, are indicative of disease or involved in the pathogenesis, by detecting levels of the target or levels of cells which express the target of interest on their cell surface in a sample taken from a patient. This may be achieved, for example, by contacting the sample to be tested, optionally along with a control sample, with the protein according to the invention under conditions that allow for binding of the protein to the target. Complex formation can then be detected (e.g., using an ELISA). When using a control sample along with the test sample, the level of protein or protein-target complex is analyzed in both samples and a statistically significant higher level of protein or protein-target complex in the test sample indicates a higher level of the target in the test sample compared with the control sample.

Examples of conventional immunoassays in which proteins of the present invention can be used include, without limitation, ELISA, RIA, FACS assays, plasmon resonance assays, chromatographic assays, tissue immunohistochemistry, Western blot, and/or immunoprecipitation.

In one embodiment, the invention relates to a method for detecting the presence of a target, or a cell expressing the target, in a sample comprising:

contacting the sample with a protein of the invention under conditions that allow for binding of the protein to the target in the sample; and analyzing whether a complex has been formed. Typically, the sample is a biological sample.

In one embodiment, the sample is a tissue sample known or suspected of containing a specific target and/or cells expressing the target. For example, in situ detection of the target expression may be accomplished by removing a histological specimen from a patient, and providing the protein of the present invention to such a specimen. The protein may be provided by applying or by overlaying the protein to the specimen, which is then detected using suitable means. It is then possible to determine not only the presence of the target or target-expressing cells, but also the distribution of the target or target-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the protein can be labeled with a detectable substance to allow bound protein to be detected. Alternatively, bound (primary) specific protein may be detected by an antibody which is labeled with a detectable substance and which binds to the primary specific protein.

The level of target in a sample can also be estimated by a competition immunoassay utilizing target standards labeled with a detectable substance and an unlabeled target-specific protein. In this type of assay, the biological sample, the labeled target standard(s) and the target-specific protein are combined, and the amount of labeled target standard bound to the unlabeled target-specific protein is determined. The amount of target in the biological sample is inversely proportional to the amount of labeled target standard bound to the target-specific protein.

Suitable labels for the target-specific protein, secondary antibody and/or target standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I, $^{131}$I, $^{35}$S, and $^3$H.

In one aspect, the target-specific proteins of the invention are used in the in vivo imaging of target-expressing tissues such as tumors. For in vivo methods, antibody fragments such as, e.g., (Fab')$_2$, Fab and Fab' fragments, are particularly advantageous because of their rapid distribution kinetics.

In vivo imaging can be performed by any suitable technique. For example, a target-specific protein (such as, e.g., an antibody or a fragment) labeled with $^{99}$Tc, $^{131}$I, $^{111}$In or other gamma-ray emitting isotope may be used to image target-specific protein accumulation or distribution in target-expressing tissues such as tumors with a gamma scintillation camera (e.g., an Elscint Apex 409ECT device), typically using low-energy, high resolution collimator or a low-energy all-purpose collimator. Alternatively, labeling with $^{89}$Zr, $^{76}$Br, $^{18}$F or other positron-emitting radionuclide may be used to image target-specific protein, antibody, or antibody fragment distribution in tumors using positron emission tomography (PET). The images obtained by the use of such techniques may be used to assess biodistribution of target in a patient, mammal, or tissue, for example in the context of using target as a biomarker for the presence of cancer/tumor cells. Variations on this technique may include the use of magnetic resonance imaging (MRI) to improve imaging over gamma camera techniques. Conventional immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Moreover, such images may also, or alternatively, serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer).

In one embodiment, the present invention provides an in vivo imaging method wherein a target-specific protein of the present invention is conjugated to a detection-promoting radio-opaque agent, the conjugated protein is administered to a host, such as by injection into the bloodstream, and the presence and location of the labeled protein in the host is assayed. Through this technique and any other diagnostic method provided herein, the present invention provides a method for screening for the presence of disease-related cells in a human patient or a biological sample taken from a human patient and/or for assessing the distribution of target-specific protein prior to target-specific ADC therapy.

For diagnostic imaging, radioisotopes may be bound to a target-specific protein either directly or indirectly by using an intermediary functional group. Useful intermediary functional groups include chelators, such as ethylenediaminetetraacetic acid and diethylenetriaminepentaacetic acid (see for instance U.S. Pat. No. 5,057,313).

In addition to radioisotopes and radio-opaque agents, diagnostic methods may be performed using target-specific proteins that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of proteins conjugated to a MRI enhancing agent). Such diagnostic/detection agents may be selected from agents for use in MRI, and fluorescent compounds. In order to load a target-specific protein with radioactive metals or paramagnetic ions, it may be necessary to react it with a reagent having a long tail to which a multiplicity of chelating groups are attached for binding the ions. Such a tail may be a polymer such as a polylysine, polysaccharide, or another derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to target-specific proteins using standard chemistries.

Thus, the present invention provides a diagnostic target-specific protein, wherein the target-specific protein is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In a further aspect, the invention relates to a kit for detecting the presence of target antigen or a cell expressing the target, in a sample, comprising:

a target-specific antibody of the invention; and
instructions for use of the kit.

In one embodiment, the present invention provides a kit for diagnosis of cancer comprising a container comprising a target-specific protein, and one or more reagents for detecting binding of the target-specific protein to the target. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more target-specific proteins of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with a target-specific protein, such as a labeled target-specific protein, for the detection of the presence of the target in a tissue sample or host. In such diagnostic kits, as well as in kits for therapeutic uses described elsewhere herein, a target-specific protein typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the target-specific protein, which typically is present in a separate container, is also included. The second antibody is typically conjugated to a label and formulated in a manner similar to the target-specific protein of the present invention. Using the methods described above and elsewhere herein, target-specific proteins may be used to define subsets of cancer/tumor cells and characterize such cells and related tumor tissues.

Sequences

| SEQ ID NO: | Clone name | Sequence |
|---|---|---|
| SEQ ID NO: 1 | huCD3 VH CDR1 | GFTFNTYA |
| SEQ ID NO: 2 | huCD3 VH CDR2 | IRSKYNNYAT |
| SEQ ID NO: 3 | huCD3 VH CDR3 | VRHGNFGNSYVSWFAY |
| SEQ ID NO: 4 | huCD3 VL CDR1 | TGAVTTSNY |
|  | huCD3 VL CDR2 | GTN |

| SEQ ID NO: | Clone name | Sequence |
| --- | --- | --- |
| SEQ ID NO: 5 | huCD3 VL CDR3 | ALWYSNLWV |
| SEQ ID NO: 6 | huCD3 VH1 | EVKLVESGGGLVQPGGSLRLSCAASGFTFNTYAMNWVRQAP<br>GKGLEWVARIRSKYNNYATYYADSVKDRFTISRDDSKSSLYL<br>QMNNLKTEDTAMYYCVRHGNFGNSYVSWFAYWGQGTLVTV<br>SS |
| SEQ ID NO: 7 | huCD3 VH2 | EVKLVESGGGLVKPGRSLRLSCAASGFTFNTYAMNWVRQAP<br>GKGLEWVARIRSKYNNYATYYADSVKDRFTISRDDSKSILYL<br>QMNNLKTEDTAMYYCVRHGNFGNSYVSWFAYWGQGTLVTV<br>SS |
| SEQ ID NO: 8 | huCD3 VH3 | EVKLVESGGGLVKPGRSLRLSCAASGFTFNTYAMNWVRQAP<br>GKGLEWVARIRSKYNNYATYYADSVKDRFTISRDDSKSILYL<br>QMNSLKTEDTAMYYCVRHGNFGNSYVSWFAYWGQGTLVTV<br>SS |
| SEQ ID NO: 9 | huCD3 VH4 | EVKLVESGGGLVKPGRSLRLSCAASGFTFNTYAMNWVRQAP<br>GKGLEWVARIRSKYNNYATYYADSVKDRFTISRDDSKSILYL<br>QMNSLKTEDTAMYYCVRHGNFGNSYVSWFAYWGQGTMVTV<br>SS |
| SEQ ID NO: 10 | huCD3 VL1 | QAVVTQEPSFSVSPGGTVTLTCRSSTGAVTTSNYANWVQQT<br>PGQAFRGLIGGTNKRAPGVPARFSGSLIGDKAALTITGAQAD<br>DESIYFCALWYSNLWVFGGGTKLTVL |
| SEQ ID NO: 11 | huCD3 VL2 | QAVVTQEPSFSVSPGGTVTLTCRSSTGAVTTSNYANWVQQT<br>PGQAFRGLIGGTNKRAPGVPARFSGSILGNKAALTITGAQAD<br>DESIYFCALWYSNLWVFGGGTKLTVL |
| SEQ ID NO: 12 | huCD3 VL3 | QAVVTQEPSFSVSPGGTVTLTCRSSTGAVTTSNYANWVQQT<br>PGQAFRGLIGGTNKRAPGVPARFSGSILGNKAALTITGAQAD<br>DESDYYCALWYSNLWVFGGGTKLTVL |
| SEQ ID NO: 13 | IgG1m(f) heavy chain constant region | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKRVEPKSCDKTHTCPPCPAPELLGGPSVFLFPP<br>KPKDTLMISRTPEVTCVVVDVSHEDPEVKFNWYVDGVEVHN<br>AKTKPREEQYNSTYRVVSVLTVLHQDWLNGKEYKCKVSNKAL<br>PAPIEKTISKAKGQPREPQVYTLPPSREEMTKNQVSLTCLVKG<br>FYPSDIAVEWESNGQPENNYKTTPPVLDSDGSFFLYSKLTVD<br>KSRWQQGNVFSCSVMHEALHNHYTQKSLSLSPGK |
| SEQ ID NO: 14 | Mature human CD3ε (epsilon) | QDGNEEMGGITQTPYKVSISGTTVILTCPQYPGSEILWQHND<br>KNIGGDEDDKNIGSDEDHLSLKEFSELEQSGYYVCYPRGSKP<br>EDANFYLYLRARVCENCMEMDVMSVATIVIVDICITGGLLLLV<br>YYWSKNRKAKAKPVTRGAGAGGRQRGQNKERPPPVPNPDYE<br>PIRKGQRDLYSGLNQRRI |
| SEQ ID NO: 15 | Human CD3δ (delta) | MEHSTFLSGLVLATLLSQVSPFKIPIEELEDRVFVNCNTSITWV<br>EGTVGTLLSDITRLDLGKRILDPRGIYRCNGTDIYKDKESTVQ<br>VHYRMCQSCVELDPATVAGIIVTDVIATLLLALGVFCFAGHET<br>GRLSGAADTQALLRNDQVYQPLRDRDDAQYSHLGGNWARN<br>K |
| SEQ ID NO: 16 | VH huCLB-T3/4 | EVQLVESGGGLVKPGGSLRLSCAASGFTFSSYGMFWVRQAP<br>GKGLEWVATISRYSRYIYYPDSVKGRFTISRDNAKNSLYLQM<br>NSLRAEDTAVYYCARRPLYGSSPDYWGQGTLVTVSS |
| SEQ ID NO: 17 | VL huCLB-T3/4 | EIVLTQSPATLSLSPGERATLSCSASSSVTYVHWYQQKPGQA<br>PRLLIYDTSKLASGIPARFSGSGSGTDFTLTISSLEPEDFAVYY<br>CFQGSGYPLTFGSGTKLEMR |
| SEQ ID NO: 18 | VH HER2 169 | QVQLVQSGAEVKKPGASVKVSCKASGYTFTNYGISWVRQAP<br>GQGLEWMGWLSAYSGNTIYAQKLQGRVTMTTDTSTTTAYME<br>LRSLRSDDTAVYYCARDRIVVRPDYFDYWGQGTLVTVSS |
| SEQ ID NO: 19 | VL HER2 169 | EIVLTQSPATLSLSPGERATLSCRASQSVSSYLAWYQQKPGQ<br>APRLLIYDASNRATGIPARFSGSGSGTDFTLTISSLEPEDFAVY<br>YCQQRSNWPRTFGQGTKVEIK |
| SEQ ID NO: 20 | IgG1m(f)-LFLEDA heavy chain constant region | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKRVEPKSCDKTHTCPPCPAPEFEGGPSVFLFP<br>PKPKDTLMISRTPEVTCVVVAVSHEDPEVKFNWYVDGVEVHN |

| SEQ ID NO: | Clone name | Sequence |
|---|---|---|
| | | AKTKPREEQYNSTYRVVSVLTVLHQDWLNGKEYKCKVSNKAL<br>PAPIEKTISKAKGQPREPQVYTLPPSREEMTKNQVSLTCLVKG<br>FYPSDIAVEWESNGQPENNYKTTPPVLDSDGSFFLYSKLTVD<br>KSRWQQGNVFSCSVMHEALHNHYTQKSLSLSPGK |
| SEQ ID NO: 21 | Mature cyno<br>CD3ε (epsilon) | QDGNEEMGSITQTPYQVSISGTTVILTCSQHLGSEAQWQHN<br>GKNKEDSGDRLFLPEFSEMEQSGYYVCYPRGSNPEDASHHLY<br>LKARVCENCMEMDVMAVATIVIVDICITLGLLLLVYYWSKNRK<br>AKAKPVTRGAGAGGRQRGQNKERPPPVPNPDYEPIRKGQQD<br>LYSGLNQRRI |

EXAMPLES

Example 1—Generation of Non-Activating Antibodies

Non-Activating Mutations

Several antibody variants were generated with one or more amino acid substitutions in the Fc region. A non-activating Fc region prevents the antibody from interacting with Fc-receptors present on blood cells, such as monocytes, or with C1q to activate the classical complement pathway. Reduction of the Fc activity was tested in antibody variants that contain different combinations of amino acid substitutions in the Fc region. Maximally five amino acid substitutions were introduced, which include the mutations N297Q, L234A, L235A, L234F, L235E, D265A, and P331S. Substitutions in one or more of these five amino acid positions were introduced in the K409R and F405L IgG1 backbone. The following Fc-domain variants were generated: NQ (refers to the N297Q substitution), LFLE (refers to the L234F/L235E substitutions), LALA (refers to the L234A/L235A substitutions), LFLENQ (refers to the L234F/L235E/N297Q substitutions), LFLEDA (refers to the L234F/L235E/D265A substitutions), DA (refers to the D265A substitution), DAPS (refers to the D265A/P331S substitutions), DANQ (refers to the D265A/N297Q substitutions), LFLEPS (refers to the L234F/L235E/P331S substitutions), and LFLEDANQPS (refers to the L234F/L235E/D265A/N297Q/P331S substitutions).

CD3 Antibodies

Various CD3 antibodies were used in monospecific and bispecific format.

In some examples the heavy and light chain variable region sequences of huCLB-T3/4 (SEQ ID NOs: 16 and 17, respectively) were used, which is a humanized version of the murine antibody CLB-T3/4. Both sequences were cloned into the relevant expression vectors and expressed by co-transfection in HEK293F cells.

In some examples humanized variant (VH according to SEQ ID NO:8 and VL according to SEQ ID NO:10) of a murine CD3 antibody (described as "huCD3") as described in U.S. Pat. No. 8,236,308 were used. Humanization of this CD3 antibody was performed by Antitope (Cambridge, UK) using their improved version of the germline humanization (CDR-grafting) technology, as described in EP 0 629 240. Using this technology, 4 different VH chains (SEQ ID NOs:6, 7, 8, and 9) and 3 different VL chains (SEQ ID NOs:10, 11, and 12) were designed.

HER2 Antibody

In some of the examples an antibody against HER2 was used. The VH and VL sequences for this HER2-specific antibody (VH HER2 169 and VL Her2 160 SEQ ID NOs:18 and 19, respectively) as described in WO2012143524 [Genmab]; and Labrijn et al., PNAS 2013, 110: 5145-50.

b12 Antibody

In some of the examples the antibody b12, a gp120 specific antibody (Barbas, C F. J Mol Biol. 1993 Apr. 5; 230(3):812-23.) was used as a negative control.

Expression

Antibodies were expressed as IgG1,κ or IgG1,λ with or without the non-activating mutations described above and being additionally modified in their Fc regions as follows: IgG1-HER2-K409R, IgG1-b12-K409R, IgG1-CD3-F405L. Plasmid DNA mixtures encoding both heavy and light chain of antibodies were transiently transfected to Freestyle HEK293F cells (Invitrogen, US) using 293fectin (Invitrogen, US) essentially as described by the manufacturer.

Purification of Antibodies

Culture supernatant was filtered over 0.2 µm dead-end filters, loaded on 5 mL MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B.Braun). Alternatively, subsequent to purification, the eluate was loaded on a HiPrep Desalting column and the antibody was exchanged into 12.6 mM NaH2PO4, 140 mM NaCl, pH 7.4 (B.Braun) buffer. After dialysis or exchange of buffer, samples were sterile filtered over 0.2 µm dead-end filters. Purity was determined by SDS-PAGE and concentration was measured by absorbance at 280 nm. Purified antibodies were stored at 4° C.

Generation of Bispecific Antibodies

Bispecific antibodies were generated in vitro according to the DuoBody® technology platform, i.e. 2-MEA-induced Fab-arm exchange as described in WO 2011/147986 and Labrijn et al. (Labrijn et al., PNAS 2013, 110: 5145-50; Gramer et al., MAbs 2013, 5: 962-973). The basis for this method is the use of complementary CH3 regions, which promote the formation of heterodimers under specific assay conditions. To enable the production of bispecific antibodies by this method, IgG1 molecules carrying certain mutations in the CH3 region were generated: in one of the parental IgG1 antibody the F405L mutation, in the other parental IgG1 antibody the K409R mutation. To generate bispecific antibodies, these two parental antibodies, each antibody at a final concentration of 0.5 mg/mL, were incubated with 25 or 75 mM 2-mercaptoethylamine-HCl (2-MEA) in a total volume of 500 µL TE at 31° C. for 5 hours. The reduction reaction was stopped when the reducing agent 2-MEA is removed by using PD-10 columns (GE-healthcare, product #17-0851-01), equilibrated with 25 mL PBS. Prior to desalting, 2 mL PBS (B.Braun, product #3623140) was added to the samples to adjust the volume to 2.5 mL. Elution was done in 3.5 mL PBS. Samples were collected in Amicon Ultra centrifugal units (30 kD MWCO, Millipore, product

UFC803096) and concentrated by centrifuging 8 min at 3000×g. Volumes were adjusted to 500 µL (when needed) with PBS and samples were sterile-filtered over a 0.2 µm filter (Millex-GV, product #SLGV004SL). The bispecific products were stored at 2-8° C.

Example 2—Binding of Antibody Mutants to Jurkat or AU565 Cells

Binding of purified variants of antibodies IgG1-CD3 (huCLB-T3/4, containing the F405L mutation), IgG1-HER2 (HER2-169, containing the K409R mutation), and bispecific (bs)IgG-CD3×HER2 molecules with additional mutations in the Fc-domain (see Example 1) to CD3-positive Jurkat cells or HER2-positive AU565 cells was analyzed by FACS analysis. Cells (1×105 cells/well) were incubated in polystyrene 96-well round-bottom plates (Greiner bio-one 650101) with serial dilutions of antibody preparations (range 2 to 10000 ng/mL in 4-fold dilutions for Jurkat cells and range 1 to 3000 ng/mL in 4-fold dilutions for on AU565 cells) in 100 µL PBS/0.1% BSA/0.02% azide at 4° C. for 30 min.

After washing twice in PBS/0.1% BSA/0.02% azide, cells were incubated in 100 µL with secondary antibody at 4° C. for 30 min. As a secondary antibody, R-Phycoerythrin (PE)-conjugated goat-anti-human IgG F(ab')$_2$ (109-116-098, Jackson ImmunoResearch Laboratories, Inc., West Grove, Pa.) diluted 1/100 in PBS/0.1% BSA/0.02% azide, was used for all experiments. Next, cells were washed twice in PBS/0.1% BSA/0.02% azide, resuspended in 150 µL PBS/0.1% BSA/0.02% azide and analyzed on a FACS CantoII (BD Biosciences). Binding curves were analyzed using non-linear regression (sigmoidal dose-response with variable slope) using GraphPad Prism V5.04 software (GraphPad Software, San Diego, Calif., USA).

Binding of IgG1-CD3 and bsIgG1-CD3×HER2 antibody variants to Jurkat cells was not affected by the introduction of the indicated mutations in the Fc-domain and was identical for all tested mutants and wild type antibody (FIGS. 1A and 1B and FIGS. 2A and 2B).

Similarly, binding of IgG1-HER2 and bsIgG1-CD3×HER2 antibody variants to AU565 cells was not affected by the introduction of the indicated mutations in the Fc-domain and was identical for all tested mutants and wild type antibody (FIGS. 1C and 1D and FIGS. 2C and 2D).

Example 3—CD69 Expression on T-Cells in PBMC Culture

CD69 expression on T-cells was evaluated by FACS analysis to determine early activation of T-cells after incubation with IgG1-CD3 antibodies with mutations in the Fc-domain (see Example 1).

PBMCs were isolated from whole blood or buffy coat by density gradient separation using Leucosep tubes (#227290; Greiner Bio-one, Alphen a/d Rijn, The Netherlands), washed with PBS and resuspended in culture medium.

A dose response series of IgG1-CD3 antibody variants, a negative control (IgG1-CD3 Fab) and positive control (IgE-CD3) were prepared in culture medium (ranging from 1 to 1000 ng/mL in 3-fold dilutions) and added to the wells of a 96-well round bottom plate containing the PBMCs. After 16-24 hours incubation, cells were pelleted by centrifugation and supernatant (containing cytokines) collected and stored at −20° C. Cells were then washed with PBS/0.1% BSA/0.02% azide and stained for 30 minutes at 4° C. with a mouse-anti-human CD28-PE (854.222.010; Sanquin, Amsterdam, The Netherlands; T-cell marker) and mouse-anti-human CD69-APC antibody (340560; BD Biosciences, Franklin Lakes, N.J.). Unbound antibodies were removed by washing twice with PBS/0.1% BSA/0.02% azide. Cells were resuspended in 150 µL/well and CD69-expression on CD28 positive cells was measured on FACS Canto II (BD Biosciences).

FIG. 3 shows that CD69 expression was high on cells which were incubated with IgG1-CD3, IgG1-CD3-DA and IgG1-CD3-DAPS. Incubation with IgG1-CD3-N297Q and IgG1-CD3-LALA induced somewhat lower expression levels of CD69 compared to wild type IgG1-CD3, and incubation with IgG1-CD3-LFLE and IgG1-CD3-LFLEPS induced CD69 to a lesser extent. Incubation of PBMCs with IgG1-CD3 Fab, IgG1-b12, IgG1-CD3-LFLEDA, IgG1-CD3-LFLENQ, IgG1-CD3-DANQ and IgG1-CD3-LFLE-DANQPS antibodies did not induce any expression of CD69 on T-cells.

Example 4—CD3 Antibody-Induced T-Cell Proliferation

The effect of CD3 antibody variants (described in Example 1) on the proliferation of T-cells was evaluated by the Cell proliferation ELISA kit from Roche Applied Science (Cell Proliferation ELISA, BrdU kit, #11647229001; Roche Applied Science, Mannheim, Germany), which was performed according to the manufacturer's instructions.

PBMCs, isolated from whole blood or buffy coat, were incubated in 96-well culture plates with dilution series (ranging from 0.1 to 1000 ng/mL) of IgG1-CD3 variants. IgE-CD3 and IgG1-CD3 were included as positive controls and IgG1-b12 (with K409R mutation for generation of bispecific antibodies) as a negative control. After 3 days of incubation with the antibodies, BrdU (Roche Applied Science, Mannheim, Germany) was added to the medium and plates were incubated for 5 hours. Cells were then pelleted by centrifugation and supernatant collected and stored at −20° C. Plates were dried and stored at 4° C. until ELISA was performed.

BrdU incorporation in the DNA was determined by ELISA according to the manufacturer's instructions (Cell Proliferation ELISA, BrdU kit, #11647229001; Roche Applied Science). Cells were fixed to the plates, where after the plates were incubated for 90 minutes at room temperature (RT) with an anti-BrdU antibody conjugated with peroxidase. Plates were washed with PBST and binding was detected using ABTS buffer (instead of the TMB solution provided with the kit). Color development was stopped after 30 min by adding 2% oxalic acid to the wells. OD405 nm was then measured on an EL808 ELISA-reader.

FIG. 4 shows that incubation of PBMCs with IgG1-CD3, IgG1-CD3-DA and IgG1-CD3-DAPS induced strong proliferation of T-cells, even at very low concentrations of antibody. Incubation with IgG1-CD3-N297Q or IgG1-CD3-LALA induced dose-dependent proliferation, which was comparable to the IgE-CD3 positive control. Incubation of PBMCs with IgG1-CD3 Fab, IgG1-b12, IgG1-CD3-LFLE, IgG1-CD3-LFLEDA, IgG1-CD3-LFLENQ, IgG1-CD3-LFLEPS, IgG1-CD3-DANQ and IgG1-CD3-LFLEDANQPS antibodies did not induce proliferation of T-cells.

Based on the results from Example 3 and 4, a subset of mutants that were considered least activating, was subjected to further analysis.

Example 5—In Vitro T-Cell-Mediated Cytotoxicity Induced by Non-Activating Antibody Variants AU565 (human breast carcinoma) cells were cultured in RPMI 1640 supplemented with 10% (vol/vol) heat inactivated CCS, 1.5 g/L sodium bicarbonate (Lonza), 1 mM sodium pyruvate, 4.5 g/L glucose (Sigma), 50 IU/mL penicillin, and 50 µg/mL streptomycin. The cell line was maintained at 37° C. in a 5% (vol/vol) $CO_2$ humidified incubator. AU565 cells were cultured to near confluency. Cells were trypsinized, re-suspended in culture medium and passed through a cell strainer to obtain a single cell suspension. $5 \times 10^4$ cells were seeded in each well of a 96-well culture plate, and cells were incubated at least 3 hrs. at 37° C., 5% CO2 to allow adherence to the plate.

Peripheral blood mononuclear cells (PBMC) were isolated from blood from healthy volunteers using Leucosep 30 mL tubes, according to the manufacturer's protocol (Greiner Bio-one). Isolated PBMCs were washed with PBS, re-suspended in culture medium and added in a 1:1 ratio to the AU565 tumor cells in the 96-well plates. The percentage of T-cells present in PBMCs was measured by FACS-analysis, using a mouse anti-human CD3-PerCP (BD, #345766) antibody (for staining T-cells). The T-cell content in the population of used PBMCs was typically 50 to 60%.

Dilution series (final concentrations ranging from 0.004 to 1000 ng/mL) of IgG1-b12, IgG1-CD3, IgG1-HER2, and bispecific CD3×b12 and CD3×HER2 antibodies expressed as different Fc-variants, wild type, N297Q, LFLE, LALA, LFLENQ, LFLEDA, DANQ, and LFLEDANQPS, were prepared in culture medium and added to the plates. Plates were incubated for 3 days at 37° C., 5% $CO_2$. Incubation of cells with 1 µM staurosporin (#S6942-200, Sigma) was used as reference for 100% tumor cell kill. After incubation, supernatants were removed and stored at −20° C. for later analysis of cytokine release (see Example 6). Plates were washed twice with PBS, and 150 µL culture medium containing 10% Alamar blue was added to each well. Plates were incubated for 4 hours at 37° C., 5% $CO_2$. Absorbance at 590 nm was measured (Envision, Perkin Elmer, Waltham, Mass.).

Two experiments were performed using PBMCs from different donors. In the first experiment Fc-variants N297Q, LFLE, LFLENQ, LFLEDA, DANQ, and LFLEDANQPS were tested (FIGS. 5A-G). In the second experiment Fc-variants LFLEDA and LALA were tested (FIG. 6A-C). Antibodies with wild-type Fc-domains were included in both experiments as reference. Incubation with wild-type monospecific IgG1-CD3 or bispecific CD3×b12 antibodies induced unspecific killing of target cells (FIGS. 5A-G and 6A-C). The monospecific IgG1-CD3 and bsIgG1-CD3×b12 variants N297Q (FIGS. 5A-G) and LALA (FIGS. 6A-C) still induced some unspecific target cell killing, albeit to a lesser extent than the wild-type antibody tested in the same experiment. Unspecific killing was not induced by any of the other tested IgG1-CD3 or bsIgG1-CD3×b12 antibodies with non-activating mutations (FIGS. 5A-G and 6A-C).

All bispecific CD3×HER2 antibodies induced dose-dependent killing of AU565 cells with at least comparable efficacy compared to the wild type bispecific CD3×HER2 antibody without non-activating mutations (FIGS. 4A-G and 6A-C). Maximum killing occurred at very low concentrations.

No cytotoxicity was induced by wild-type or non-activating variants of the monospecific b12 or HER2 antibodies (FIGS. 4A-G and 6A-C).

Example 6—Cytokine Release Induced by Non-Activating Antibody Variants

Cytokines present in supernatant samples from cytotoxicity assays as performed in Example 5 were quantified using the Pro-inflammatory kit (MSD, # K15007B-1).

In short, supernatant and calibrator samples were added to the multiplex plates and incubated for 1-2 hours at room temperature. Subsequently, 1x Detection Antibody Solution, which was provided with the kit, was added to the wells and incubated for another 1-2 hrs. The plates were washed 3 times with PBST, Read Buffer T was added to the wells and chemiluminescence was measured on an imager. Cytokine concentrations were calculated using the standard curves obtained from the calibrator samples.

The results of the production of 9 cytokines (IFNγ, TNFα, GM-CSF, IL-1β, IL-2, IL-6, IL-8, IL-10, IL-12) are shown in FIG. 7A-I. Wild-type IgG1-CD3 induced production of all 9 tested cytokines in various amounts. Incubation of target and effector cells with monospecific IgG1-CD3 antibody variants LFLENQ, LFLEDA, DANQ, and LFLEDANQPS did not lead to substantial production of IFNγ, TNFα, GM-CSF, IL-1β, IL-2, IL-6, and IL-10, and production of small amounts of IL-8 and IL-12. Incubation of target and effector cells with monospecific IgG1-CD3-LALA variant induced production high amounts of IL-8, production of low amounts of 7 cytokines (IFNγ, TNFα, GM-CSF, IL-1β, IL-6, IL-10, IL-12), and no substantial amounts of IL-2.

Bispecific IgG1-CD3×HER2 antibodies, both wild-type and non-activating variants, induced production of all 9 cytokines (FIG. 7A-I). Cytokine production induced by bispecific IgG1-CD3×HER2 antibodies was somewhat higher compared to the cytokine production induced by the wild-type monospecific IgG1-CD3 control, with the exception of production of IL-1β and IL-2.

Example 7—Evaluation of Binding of C1q to Non-Activating Antibody Variants

Interaction of C1q with antibodies bound to a target cell is the first step in the classical pathway of complement activation. Since wild-type IgG1 harbors the interaction site for C1q, the interaction of C1q to these non-activating IgG1 variants by an ELISA was evaluated.

Dilution series (range 7-30000 ng/mL in 4-fold dilutions) of IgG1-CD3, bsIgG1-CD3×HER2 and IgG1-CD20 (positive control) and non-activating antibody variants as described above in Example 1 thereof were coated on 96-well Microlon ELISA plates (Greiner, Germany) overnight at 4° C. Plates were washed and blocked with PBS supplemented with 0.025% Tween 20 and 0.1% gelatine. With washings in between incubations, plates were sequentially incubated with 3% pooled human serum (Sanquin, product# M0008) for 1 h at 37° C., with 100 µL/well rabbit anti-human C1q (DAKO, product# A0136, 1/4.000) for 1 h at RT, and with 100 µL/well swine anti-rabbit IgG-HRP (DAKO, P0399, 1:10.000) as detecting antibody for 1 h at RT. Detection was performed by addition of 1 mg/mL 2,2'-azino-bis (3-ethylbenzothiazoline-6-sulfonic acid) (ABTS; Roche, Mannheim, Germany) for about 30 min. The reaction was stopped by the addition of 100 µL 2% oxalic acid. Absorbance was measured at 405 nm in a microplate reader (Biotek, Winooski, Vt.). Log transformed data were analyzed by fitting sigmoidal dose-response curves with variable slope using GraphPad Prism software.

C1q showed binding to the antibodies with wild-type IgG1 Fc regions, IgG1-CD20, IgG1-CD3 and bsIgG1 CD3× HER2 (FIG. 8). No binding of C1q was detected on all evaluated antibody variants with non-activating mutations (N297Q, LFLE, LFLENQ, LFLEDA, DA, DAPS, DANQ, LFLEPS, LFLEDANQPS, LALA) (FIG. 8).

Example 8—Binding of Non-Activating Antibody Variants to FcγRI

Binding of IgG1-CD3 antibody variants N297Q, LFLE, LFLEDA, LFLENQ, DANQ, LFLEDANQPS and LALA to the high affinity FcγRI expressed by IIa1.6 FcγRI cells was evaluated by FACS analysis.

IIa1.6 FcγRI cells (Van Vugt et al. Blood 1999, 94: 808-817) were cultured in RPMI medium supplemented with 10% Cosmic calf serum, 25 mg/ml (55 mM) Methotrexate, 50 IU/mL penicillin, and 50 µg/mL streptomycin. The cell line was maintained at 37° C. in a 5% (vol/vol) $CO_2$ humidified incubator.

IIa1.6 FcγRI cells ($1 \times 10^5$ cells/well) were incubated with serial dilutions of antibody preparations (range 10 to 10000 ng/mL in 4-fold dilutions) for 30 min at 4° C. in polystyrene 96-well round-bottom plates (Greiner bio-one, #650101). Cells were washed with PBS/0.1% BSA/0.02% azide and stained for 30 minutes at 4° C. with R-Phycoerythrin (PE)-conjugated goat-anti-human IgG F(ab')2 (109-116-098, Jackson ImmunoResearch Laboratories) diluted 1/100 in PBS/0.1% BSA/0.02% azide. Then, cells were washed with PBS/0.1% BSA/0.02% azide, resuspended in 150 µL PBS/0.1% BSA/0.02% azide and analyzed on a FACS CantoII (BD Biosciences). Binding curves were analyzed using non-linear regression (sigmoidal dose-response with variable slope) using GraphPad Prism V5.04 software (GraphPad Software, San Diego, Calif., USA).

Wild-type IgG1-CD3 antibody showed strong binding to FcγRI (FIG. 9). IgG1-CD3 antibody variants N297Q and LALA showed weak binding to FcγRI on IIa1.6 FcγRI cells when tested at higher concentrations (>1000 ng/mL; FIG. 9). No substantial binding to IIa1.6 FcγRI cells was observed for antibody variants LFLE, LFLEDA, LFLENQ, DANQ and LFLEDANQPS (FIG. 9).

Example 9—Pharmacokinetic (PK) Analysis of Non-Activating Antibody Variants

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee. 7-10 Weeks old C.B-17 SCID mice (C.B-17/Icr-Prkdc<Scid>/IcrIcoCrl, Charles-River) were injected intravenously with 100 µg wild-type antibody (IgG1-CD3, IgG1-HER2, or bsIgG CD3×HER2) or non-activating variants thereof (LALA, LFLEDA, LFLENQ, DANQ or LFLEDANQPS) using 3 mice per group. 50 µL blood samples were collected from the saphenous vein at 10 minutes, 4 hours, 1 day, 2 days, 7 days, 14 days and 21 days after antibody administration. Blood was collected into heparin containing vials and centrifuged for 5 minutes at 10,000×g. Plasma was stored at −20° C. until determination of antibody concentrations.

Human IgG concentrations were determined using a total hIgG sandwich ELISA. For this assay, mouse mAb anti-human IgG-kappa clone MH16 (#M1268, CLB Sanquin, The Netherlands), coated to 96-well Microlon ELISA plates (Greiner, Germany) at a concentration of 2 µg/mL was used as capturing antibody. After blocking plates with PBS supplemented with 0.2% bovine serum albumin, samples were added, serially diluted with ELISA buffer (PBS supplemented with 0.05% Tween 20 and 0.2% bovine serum albumin), and incubated on a plate shaker for 1 h at room temperature (RT). Plates were subsequently incubated with goat anti-human IgG immunoglobulin (#109-035-098, Jackson, West Grace, Pa.) and developed with 2,2'-azino-bis (3-ethylbenzthiazoline-6-sulfonic acid) (ABTS; Roche, Mannheim, Germany). The reaction was stopped after 30 min by adding 2% oxalic acid to the wells. Absorbance was measured in a microplate reader (Biotek, Winooski, Vt.) at 405 nm.

Plasma clearance rates (mL/day/kg) were calculated based on the area under the curve (AUC), according to the following equation:

$$\text{Plasma clearance} = \frac{\text{Dose}(\mu g/kg)}{AUC(\mu g/mL/day)}$$

Data analysis was performed using Graphpad prism software.

FIG. 10A shows that the plasma human IgG concentrations were lower for antibody variants N297Q, DANQ, LFLENQ, and LFLEDANQPS when compared to wild-type antibodies. The human IgG concentrations in plasma for antibody variants LFLEDA and LALA were similar to those of wild-type antibodies.

FIG. 10B shows that the plasma clearance rates of antibody variants N297Q, DANQ and LFLENQ were 2 to 3-fold higher than that of wild-type antibody. The clearance rate of antibody variant LFLEDANQPS was 3-5 times higher than that of wild-type antibody. Plasma clearance rates of antibody variants LFLEDA and LALA were similar to that of wild-type antibody.

Example 10—Binding of Humanized CD3 Antibodies and Non-Activating Variants Thereof to Human and Cynomolgous T-Cell Lines Binding of purified variants of humanized CD3 (huCD3) antibodies and bispecific (bs)IgG1-huCD3×HER2 molecules with or without LFLEDA mutations in the Fc-domain (see Example 1) to the human T-cell line Jurkat or the cynomolgous T-cell line HSC-F was analyzed by FACS analysis. In addition to the non-activating mutations, LFLEDA antibody variants comprise F405L or K409R mutations as described in Example 1.

Cells ($1 \times 10^5$ cells/well) were incubated in polystyrene 96-well round-bottom plates (Greiner bio-one 650101) with serial dilutions of antibody preparations (range 5 to 10,000 ng/mL in 3-fold dilutions) in 100 µL PBS/0.1% BSA/0.02% azide at 4° C. for 30 min.

After washing twice in PBS/0.1% BSA/0.02% azide, cells were incubated in 100 µL with secondary antibody at 4° C. for 30 min. As a secondary antibody, R-Phycoerythrin (PE)-conjugated goat-anti-human IgG F(ab')2 (109-116-098, Jackson ImmunoResearch Laboratories, Inc., West Grove, Pa.) diluted 1/100 in PBS/0.1% BSA/0.02% azide, was used for all experiments. Next, cells were washed twice in PBS/0.1% BSA/0.02% azide, resuspended in 150 µL PBS/0.1% BSA/0.02% azide and analyzed on a FACS CantoII (BD Biosciences). Binding curves were analyzed using non-linear regression (sigmoidal dose-response with variable slope) using GraphPad Prism V5.04 software (GraphPad Software, San Diego, Calif., USA).

FIG. 11A shows that binding to Jurkat cells of the IgG1-huCD3 variants H1L1 (SEQ ID NOs:6 and 10, respectively), H1L2 (SEQ ID NOs:6 and 11, respectively), H1L3 (SEQ ID NOs:6 and 12), H3L3 (SEQ ID NOs: 8 and 12, respectively), and H4L1 (SEQ ID NOs:9 and 10, respectively) with wild type Fc region and parental IgG1-CD3 and IgG1-huCD3-H3L1 with LFLEDA mutations was similar. Binding of IgG1-huCLB-3/4, included as positive control, was strong to Jurkat cells in comparison with the IgG1-huCD3 variants. No binding was observed for the negative control antibody IgG1-b12. H1 refers to the variable heavy chain region VH1, V1 refers to the variable light chain region VL1, and so forth.

FIG. 11B shows that bispecific antibody variants bsIgG1 CD3×HER2, bsIgG1 CD3×b12-LFLEDA, and bsIgG1 huCD3-H3L1×HER2-LFLEDA also bind to Jurkat cells. The maximal binding values for these bispecific antibodies is higher than the maximal binding values of the monospecific antibodies. The EC50 concentrations of the bispecific antibodies were 6 to 10-fold higher. Again, no binding was observed for the negative control antibody IgG1-b12.

FIG. 12A shows that binding of the IgG1-huCD3 variants H1L1, H1L2, H1L3, H3L3, and H4L1 (as described above) with wild-type Fc region and parental IgG1-CD3 and IgG1-huCD3-H3L1 with LFLEDA mutations to the cynomolgous T-cell line HSC-F was similar. No binding was observed for huCLB-3/4, which does not cross-react with cynomolgous CD3, and the negative control antibody IgG1-b12.

FIG. 12B shows that bispecific antibody variants bsIgG1 CD3×HER2 and bsIgG1 huCD3-H3L1×HER2-LFLEDA also bind to HSC-F cells. The maximal binding values for these bispecific antibodies is higher than the maximal binding values of the monospecific anti-CD3 variants. The EC50 concentrations of the bispecific antibodies were 10 to 12-fold higher than that of the monospecific anti-CD3 antibodies. Again, no binding was observed for the negative control antibody IgG1-b12.

Example 11—T-Cell Activation by Humanized CD3 Antibody Variants

CD69 expression on T-cells was evaluated by FACS analysis to determine early activation of T-cells after incubation with humanized CD3 (huCD3) antibody variants with and without LFLEDA mutations in the Fc region. In addition to the non-activating mutations, LFLEDA antibody variants comprise F405L or K409R mutations as described in Example 10.

PBMCs were isolated from whole blood or buffy coat by density gradient separation using Leucosep tubes (#227290; Greiner Bio-one, Alphen a/d Rijn, The Netherlands), washed with PBS and re-suspended in culture medium.

A dose response series of huCD3 antibody variants, a negative control (IgG1-b12) and positive controls (IgE-huCD3 and parental IgG1-CD3) were prepared in culture medium (ranging from 0.1 to 1,000 ng/mL in 10-fold dilutions) and added to the wells of a 96-well round bottom plate containing human or cynomolgous PBMCs. After 16-24 hours incubation, cells were pelleted by centrifugation and supernatant (containing cytokines) collected and stored at −20° C. Cells were then washed with PBS/0.1% BSA/0.02% azide and stained for 30 minutes at 4° C. with a mouse-anti-human CD28-PE (854.222.010; Sanquin, Amsterdam, The Netherlands; T-cell marker) and mouse-anti-human CD69-APC antibody (340560; BD Biosciences, Franklin Lakes, N.J.). Unbound antibodies were removed by washing twice with PBS/0.1% BSA/0.02% azide. Cells were re-suspended in 150 µL/well and CD69-expression on CD28 positive cells was measured on FACS Canto II (BD Biosciences).

FIG. 13 shows that parental IgG1-CD3 and humanized IgG1-huCD3 variants with wild type Fc region induced similar levels of CD69 expression on T-cells from human (FIG. 13A) and cynomolgous (FIG. 13B) origin. Non-activating (LFLEDA) parental IgG1-CD3 and IgG1-huCD3-H3L1 variants induced low levels of CD69 expression in human T-cells. No expression of CD69 was induced by the non-activating IgG1-huCD3 variants in cynomolgous T-cells. The control antibody IgG1-b12 also did not induce expression of CD69 in human or cynomolgous T-cells.

Example 12—T-Cell Proliferation Induced by Humanized CD3 Antibody Variants

The effect of humanized CD3 (huCD3) antibody variants (described in Examples 1 and 10) on the proliferation of human and cynomolgous T-cells was evaluated by the Cell proliferation ELISA kit from Roche Applied Science (Cell Proliferation ELISA, BrdU kit, #11647229001; Roche Applied Science, Mannheim, Germany), which was performed according to the manufacturer's instructions.

Human or cynomolgous PBMCs, isolated from whole blood or buffy coat, were incubated in 96-well culture plates with dilution series (ranging from 0.1 to 1,000 ng/mL in 10-fold dilutions) of huCD3 antibody variants. IgE-CD3 and IgG1-huCLB-T3/4 were included as positive controls and IgG1-b12 as negative control. After 3 days of incubation with the antibodies, BrdU (Roche Applied Science, Mannheim, Germany) was added to the medium and plates were incubated for 5 hours. Cells were then pelleted by centrifugation and supernatant collected and stored at −20° C. Plates were dried and stored at 4° C. until ELISA was performed.

BrdU incorporation in the DNA was determined by ELISA according to the manufacturer's instructions (Roche Applied Science, see cat. number specified above). Cells were fixed to the plates, where after the plates were incubated for 90 minutes at RT with an anti-BrdU antibody conjugated with peroxidase. Plates were washed with PBST and binding was detected using ABTS buffer (instead of the TMB solution provided with the kit). Color development was stopped after 30 min by adding 2% oxalic acid to the wells. OD405 nm was then measured on an EL808 ELISA-reader.

FIG. 14 shows that incubation of PBMCs with parental IgG1-CD3 and humanized IgG1-huCD3 variants with wild-type Fc region induced strong proliferation of human (FIG. 14A) and cynomolgous (FIG. 14B) T-cells, even at very low concentrations of antibody. Incubation with non-activating LFLEDA variants of the IgG1-huCD3 antibodies did not induce proliferation of human or cynomolgous T-cells. Thus, although the non-activating variants of the IgG1-huCD3 antibodies induced low levels of CD69 expression in human T-cells (as shown in Example 11), no proliferation of human T-cells was induced by these non-activating IgG1-huCD3 variants.

Example 13—In Vitro T-Cell-Mediated Cytotoxicity Induced by Humanized CD3 Antibody Variants AU565 (human breast carcinoma) cells were cultured in RPMI 1640 supplemented with 10% (vol/vol) heat inactivated CCS, 1.5 g/L sodium bicarbonate (Lonza), 1 mM sodium pyruvate, 4.5 g/L glucose (Sigma), 50 IU/mL penicillin, and 50 µg/mL streptomycin. The cell line was maintained at 37° C. in a 5% (vol/vol) $CO_2$ humidified incubator. AU565 cells were cultured to near confluency, after which cells were trypsinized, re-suspended in culture medium and passed through a cell strainer to obtain a single cell suspension. $5 \times 10^4$ cells were seeded in each well of a 96-well culture plate, and cells were incubated at least 3 hrs. at 37° C., 5% CO2 to allow adherence to the plate.

Human or cynomolgous PBMCs were isolated from whole blood or buffy coat. Isolated PBMCs were washed with PBS, re-suspended in culture medium and added in a 1:1 ratio to the AU565 tumor cells in the 96-well plates. The percentage of T-cells present in PBMCs was measured by FACS-analysis, using a mouse anti-human CD3-PerCP (BD, #345766) antibody (for staining T-cells). The T-cell content in the population of used PBMCs was typically 50 to 60%.

Dilution series (final concentrations ranging from 0.001 to 1,000 ng/mL) of bispecific antibody variants bsIgG1 CD3×HER2, bsIgG1 CD3×b12-LFLEDA, and bsIgG1 huCD3-H3L1×HER2-LFLEDA were prepared in culture medium and added to the plates. IgG1-HER2-LFLEDA and IgG1-b12 were included as controls. In addition to the non-activating mutations, LFLEDA antibody variants comprise F405L or K409R mutations for preparation in bispecific format (see Example 10). Plates were incubated for 3 days at 37° C., 5% $CO_2$. Incubation of cells with 1 μM staurosporin (#S6942-200, Sigma) was used as reference for 100% tumor cell kill. Plates were washed twice with PBS, and 150 μL culture medium containing 10% Alamar blue was added to each well. Plates were incubated for 4 hours at 37° C., 5% $CO_2$. Absorbance at 590 nm was measured (Envision, Perkin Elmer, Waltham, Mass.). Bispecific CD3×HER2-LFLEDA antibody variants (parental and humanized H3L1 variant) induced killing of AU565 cells at low concentrations using human or cynomolgous effector cells (FIG. 15). The CD3 bispecific antibody huCLB-T3/4×HER2-LFLEDA, which shows no cross reactivity with cynomolgous CD3, only induced killing of AU565 cells when human PBMCs were used (FIG. 15A). Thus, no killing of target cells was observed when cynomolgous effector cells were used in the assay (FIG. 15B). Incubation with monospecific IgG1-b12 or IgG1-HER2-LFLEDA or bispecific CD3×b12-LFLEDA antibodies did not induce unspecific killing of target cells (FIG. 15).

The invention claimed is:

1. A protein comprising a first polypeptide and a second polypeptide, wherein said first and second polypeptide each comprises at least a hinge region, a CH2 region and a CH3 region of an immunoglobulin heavy chain, wherein in at least one of said first and second polypeptide the amino acids in the positions corresponding to positions L234, L235, D265, N297, and P331 in a human IgG1 heavy chain are F, E, A, N, and P, respectively, and wherein the amino acids are numbered according to the EU Index.

2. The protein according to claim 1, wherein said protein has a plasma clearance rate (mL/day/kg) which deviates from a wild-type protein by no more than 10%, wherein the plasma clearance rate is calculated by the dose (μg/kg) administered to a subject divided by the area under the curve (AUC), wherein the AUC value is determined from concentration-time curves.

3. The protein according to claim 1, wherein said first and second polypeptide is a first and a second heavy chain of an immunoglobulin, respectively.

4. The protein according to claim 1, wherein said first and second polypeptide further comprises a first and a second binding region, respectively.

5. The protein according to claim 1, wherein said protein further comprises a first and a second light chain of an immunoglobulin, wherein said first light chain is connected with said first heavy chain via disulfide bridges and said second light chain is connected with said second heavy chain via disulfide bridges, thereby forming a first binding region and a second binding region, respectively.

6. The protein according to claim 1, wherein at least one of said first and second binding regions bind CD3.

7. The protein according to claim 1, wherein both said first and second binding regions bind CD3.

8. The protein according to claim 1, wherein said protein, when present as a monospecific antibody binding CD3, mediates reduced Fc-mediated CD69 expression by at least 50when compared to a wild-type protein, when the CD69 expression is determined in a peripheral blood mononuclear cell (PBMC)-based functional assay.

9. The protein according to claim 1, wherein said protein, when present as a monospecific antibody binding CD3, mediates reduced Fc-mediated T-cell proliferation compared to a wild-type protein by at least 50%, when the T-cell proliferation is measured in a PBMC-based functional assay.

10. The protein according to claim 1, wherein the isotype of the immunoglobulin heavy chain is selected from the group consisting of IgG1, IgG2, IgG3, and IgG4.

11. The protein according to claim 1, wherein at least said first binding region is selected from the group consisting of:
   a. a binding region comprising heavy chain variable region sequence as set out in SEQ ID NO:6 and light chain variable region sequence as set out in SEQ ID NO:12;
   b. a binding region comprising heavy chain variable region sequence as set out in SEQ ID NO:8 and light chain variable region sequence as set out in SEQ ID NO:12; and
   c. a binding region comprising heavy chain variable region sequence as set out in SEQ ID NO:9 and light chain variable region sequence as set out in SEQ ID NO:10.

12. The protein according to claim 1, wherein said first binding region binds a different target than said second binding region.

13. The protein according to claim 12, wherein the targets are present on different cells.

14. The protein according to claim 1, wherein in said first polypeptide at least one of the amino acids in the positions corresponding to a position selected from the group consisting of T366, L368, K370, D399, F405, Y407, and K409 in a human IgG1 heavy chain has been substituted, and in said second polypeptide at least one of the amino acids in the positions corresponding to a position selected from the group consisting of T366, L368, K370, D399, F405, Y407, and K409 in a human IgG1 heavy chain has been substituted, and wherein said substitutions of said first and said second polypeptides are not in the same positions.

15. The protein according to claim 14, wherein the amino acid in the position corresponding to F405 in a human IgG1 heavy chain is L in said first polypeptide, and the amino acid in the position corresponding to K409 in a human IgG1 heavy chain is R in said second polypeptide, or vice versa.

16. The protein according to claim 1, which is an antibody.

17. The protein according to claim 1, wherein the protein is a bispecific antibody.

18. The protein according to claim 17, wherein both said first and second polypeptide the amino acids in the positions corresponding to L234, L235, and D265 in a human IgG1 heavy chain are F, E, and A, respectively, said first binding region binds CD3, and said second binding region binds a cancer-specific target.

19. A composition comprising the protein of claim 1.

20. A pharmaceutical composition comprising the protein of claim 1, and a pharmaceutical acceptable carrier.

* * * * *